US011236178B2

(12) United States Patent
Olsen

(10) Patent No.: US 11,236,178 B2
(45) Date of Patent: Feb. 1, 2022

(54) METHODS OF USING MONOCLONAL ANTIBODIES TARGETING EPITOPES OF ASPH

(71) Applicant: Midwestern University, Downers Grove, IL (US)

(72) Inventor: Mark Jon Olsen, Phoenix, AZ (US)

(73) Assignee: Midwestern University, Downers Grove, IL (US)

( * ) Notice: Subject to any disclaimer, the term of this patent is extended or adjusted under 35 U.S.C. 154(b) by 0 days.

(21) Appl. No.: 17/036,337

(22) Filed: Sep. 29, 2020

(65) Prior Publication Data

US 2021/0009713 A1 Jan. 14, 2021

Related U.S. Application Data

(62) Division of application No. 16/444,617, filed on Jun. 18, 2019, now Pat. No. 10,961,320.

(60) Provisional application No. 62/686,107, filed on Jun. 18, 2018.

(51) Int. Cl.
*C07K 16/00* (2006.01)
*C07K 16/40* (2006.01)
*C07K 16/28* (2006.01)

(52) U.S. Cl.
CPC .......... *C07K 16/40* (2013.01); *C07K 16/2818* (2013.01); *C07K 16/2827* (2013.01); *C07K 2317/24* (2013.01); *C07K 2317/32* (2013.01); *C07K 2317/565* (2013.01); *C07K 2317/73* (2013.01)

(58) Field of Classification Search
None
See application file for complete search history.

(56) References Cited

PUBLICATIONS

1. Aihara, A., C. K. Huang, M. J. Olsen, Q. Lin, W. Chung, Q. Tang, X. Dong and J. R. Wands (2014). "A cell-surface beta-hydroxylase is a biomarker and therapeutic target for hepatocellular carcinoma." Hepatology 60(4): 1302-1313.
2. Borgas, D. L., J. S. Gao, M. Tong and S. M. De La Monte (2015). "Potential Role of Phosphorylation as a Regulator of Aspartyl-(asparaginyl)-beta-hydroxylase: Relevance to Infiltrative Spread of Human Hepatocellular Carcinoma." Liver Cancer 4(3): 139-153.
3. Borgas, D. L., J. S. Gao, M. Tong, N. Roper and S. M. De La Monte (2015). "Regulation of Aspartyl-(Asparaginyl)-beta-Hydroxylase Protein Expression and Function by Phosphorylation in Hepatocellular Carcinoma Cells." J Nat Sci 1(4).
4. Cantarini, M. C., S. M. De La Monte, M. Pang, M. Tong, A. D'errico, F. Trevisani and J. R. Wands (2006). "Aspartyl-asparagyl beta hydroxylase over-expression in human hepatoma is linked to activation of insulin-like growth factor and notch signaling mechanisms." Hepatology 44(2): 446-457.
5. Dinchuk, J. E., R. J. Focht, J. A. Kelley, N. L. Henderson, N. I. Zolotarjova, R. Wynn, N. T. Neff, J. Link, R. M. Huber, T. C. Burn, M. J. Rupar, M. R. Cunningham, B. H. Selling, J. Ma, A. A. Stern, G. F. Hollis, R. B. Stein and P. A. Friedman (2002). "Absence of post-translational aspartyl beta-hydroxylation of epidermal growth factor domains in mice leads to developmental defects and an increased incidence of intestinal neoplasia." J Biol Chem 277(15): 12970-12977.
6. Drakenberg, T., P. Fernlund, P. Roepstorff and J. Stenflo (1983). "beta-Hydroxyaspartic acid in vitamin K-dependent protein C." Proc Natl Acad Sci U S A 80(7): 1802-1806.
7. El Asmar, Z., J. Terrand, M. Jenty, L. Host, M. Mlih, A. Zerr, H. Justiniano, R. L. Matz, C. Boudier, E. Scholler, J. M. Garnier, D. Bertaccini, D. Thierse, C. Schaeffer, A. Van Dorsselaer, J. Herz, V. Bruban and P. Boucher (2016). "Convergent Signaling Pathways Controlled by LRP1 (Receptor-related Protein 1) Cytoplasmic and Extracellular Domains Limit Cellular Cholesterol Accumulation." J Biol Chem 291(10): 5116-5127.
8. Furler, R. L., D. F. Nixon, C. A. Brantner, A. Popratiloff and C. H. Uittenbogaart (2018). "TGF-beta Sustains Tumor Progression through Biochemical and Mechanical Signal Transduction." Cancers (Basel) 10(6).99; https://doi.org/10.3390/cancers10060199.
9. Gundogan, F., G. Elwood, D. Greco, L. P. Rubin, H. Pinar, R. I. Carlson, J. R. Wands and S. M. De La Monte (2007). "Role of aspartyl-(asparaginyl) beta-hydroxylase in placental implantation: Relevance to early pregnancy loss." Hum Pathol 38(1): 50-59.
10. Iwagami, Y., S. Casulli, K. Nagaoka, M. Kim, R. I. Carlson, K. Ogawa, M. S. Lebowitz, S. Fuller, B. Biswas, S. Stewart, X. Dong, H. Ghanbari and J. R. Wands (2017). "Lambda phage-based vaccine induces antitumor immunity in hepatocellular carcinoma." Heliyon 3(9): e00407.
11. Lavaissiere, L., S. Jia, M. Nishiyama, S. De La Monte, A. M. Stern, J. R. Wands and P. A. Friedman (1996). "Overexpression of human aspartyl(asparaginyl)beta-hydroxylase in hepatocellular carcinoma and cholangiocarcinoma." J Clin Invest 98(6): 1313-1323.
12. Noda, T., M. Shimoda, V. Ortiz, A. E. Sirica and J. R. Wands (2012). "Immunization with aspartate-beta-hydroxylase-loaded dendritic cells produces antitumor effects in a rat model of intrahepatic cholangiocarcinoma." Hepatology 55(1): 86-97.
13. Revskaya, E., Z. Jiang, A. Morgenstern, F. Bruchertseifer, M. Sesay, S. Walker, S. Fuller, M. S. Lebowitz, C. Gravekamp, H. A. Ghanbari and E. Dadachova (2017). "A Radiolabeled Fully Human Antibody to Human Aspartyl (Asparaginyl) beta-Hydroxylase Is a Promising Agent for Imaging and Therapy of Metastatic Breast Cancer." Cancer Biother Radiopharm 32(2): 57-65.

(Continued)

*Primary Examiner* — Jennifer E Graser
(74) *Attorney, Agent, or Firm* — The Law Offices of Verne A. Luckow LLC

(57) ABSTRACT

Monoclonal antibodies (MAbs) targeting one or more specific epitopes of aspartyl (asparaginyl) β-hydroxylase (ASPH), including humanized, bi-specific, and other chimeric MAb variants, and fragments thereof (collectively ASPH epitope-specific MAbs, or simply ASPH MAbs), are disclosed. Methods of production, purification, and use of the ASPH epitope-specific MAbs, and compositions comprising them, as agents in therapeutic and diagnostic applications to interact with target molecules in cell-free samples, cell- and tissue-based assays, animal models, and in a subject are also disclosed. Other aspects of the invention relate to use of the molecules disclosed herein to diagnose, ameliorate, or treat cell proliferation disorders and related diseases.

13 Claims, 28 Drawing Sheets

Specification includes a Sequence Listing.

(56) References Cited

PUBLICATIONS

14. Tong, M., J. S. Gao, D. Borgas and S. M. De La Monte (2013). "Phosphorylation Modulates Aspartyl-(Asparaginyl)-beta Hydroxylase Protein Expression, Catalytic Activity and Migration in Human Immature Neuronal Cerebellar Cells." Cell Biol (Henderson, NV) 6(2).
15. Wu, G., Z. Ma, Y. Cheng, W. Hu, C. Deng, S. Jiang, T. Li, F. Chen and Y. Yang (2018). "Targeting Gas6/TAM in cancer cells and tumor microenvironment." Mol Cancer 17(1): 20.
16. Yang, H., K. Song, T. Xue, X. P. Xue, T. Huyan, W. Wang and H. Wang (2010). "The distribution and expression profiles of human Aspartyl/Asparaginyl beta-hydroxylase in tumor cell lines and human tissues." Oncol Rep 24(5): 1257-1264.
17. Yeung, Y. A., A. H. Finney, I. A. Koyrakh, M. S. Lebowitz, H. A. Ghanbari, J. R. Wands and K. D. Wittrup (2007). "Isolation and characterization of human antibodies targeting human aspartyl (asparaginyl) beta-hydroxylase." Hum Antibodies 16(3-4): 163-176.
18. P(PDB ID 5JZZ: McDonough, M.A., Pfeffer, I., and Munzel (2016) Aspartyl/Asparaginyl beta-hydroxylase (AspH) oxygenase and TPR domains in complex with manganese, N-oxalylglycine and cyclic peptide substrate mimic of factor X. DOI: 10.2210/pdb5JZZ/pdb).
19. Dahlen E., Veltonmaki, and Norten, P. (2018) Bispecific antibodies in cancer immunotherapy. Therapeutic Advances in Vaccines and Immunotherapy 6(1): 3-17.

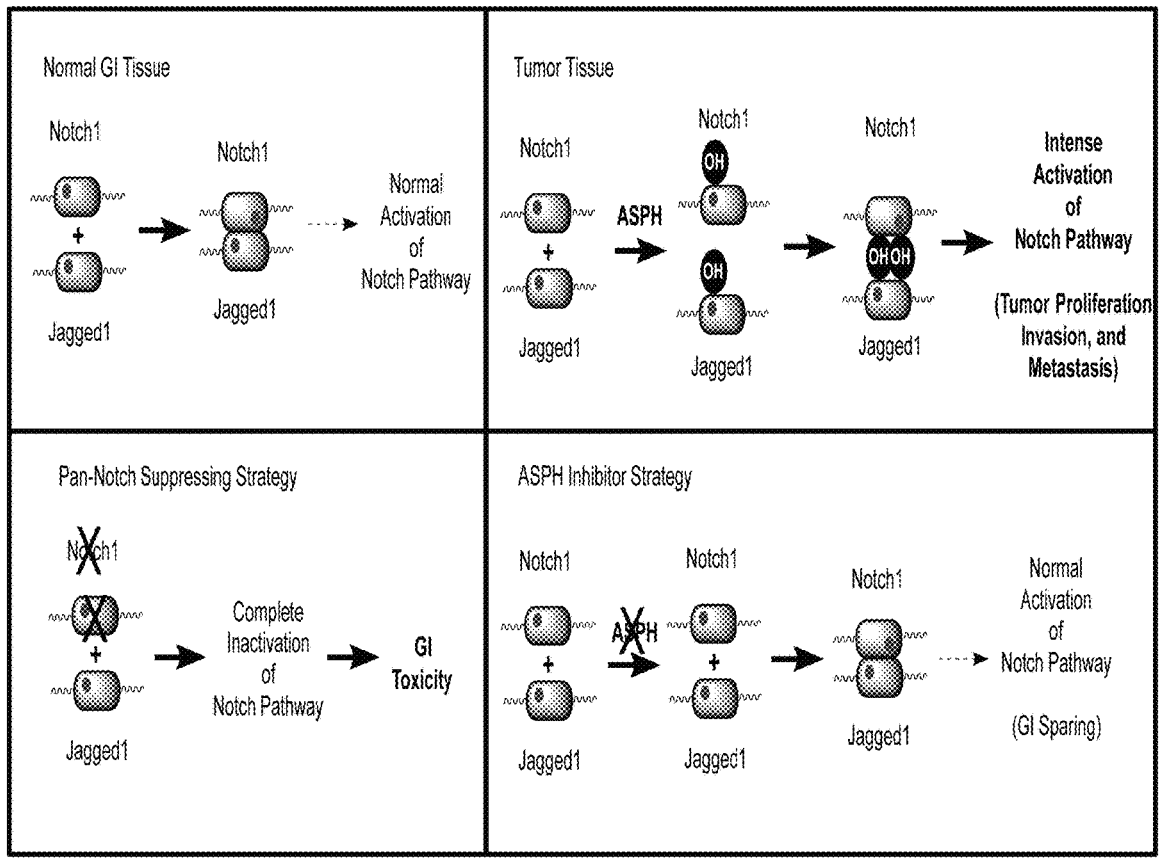

Activation of Notch Signaling Pathway by ASPH

Aspartyl(asparaginyl)-β-hydroxylase (ASPH) is an iron-dependent dioxygenase that catalyzes the hydroxylation of β carbons of aspartic acid and asparagine residues in domains of a variety of proteins, including Notch and Notch ligand homologs.

Intense activation of the Notch pathway by ASPH is observed in tumor tissues.

Inhibition of ASPH allows normal activation of the Notch Pathway.

Figure 1

Locations of Epitopes on Human ASPH (3D Structure)

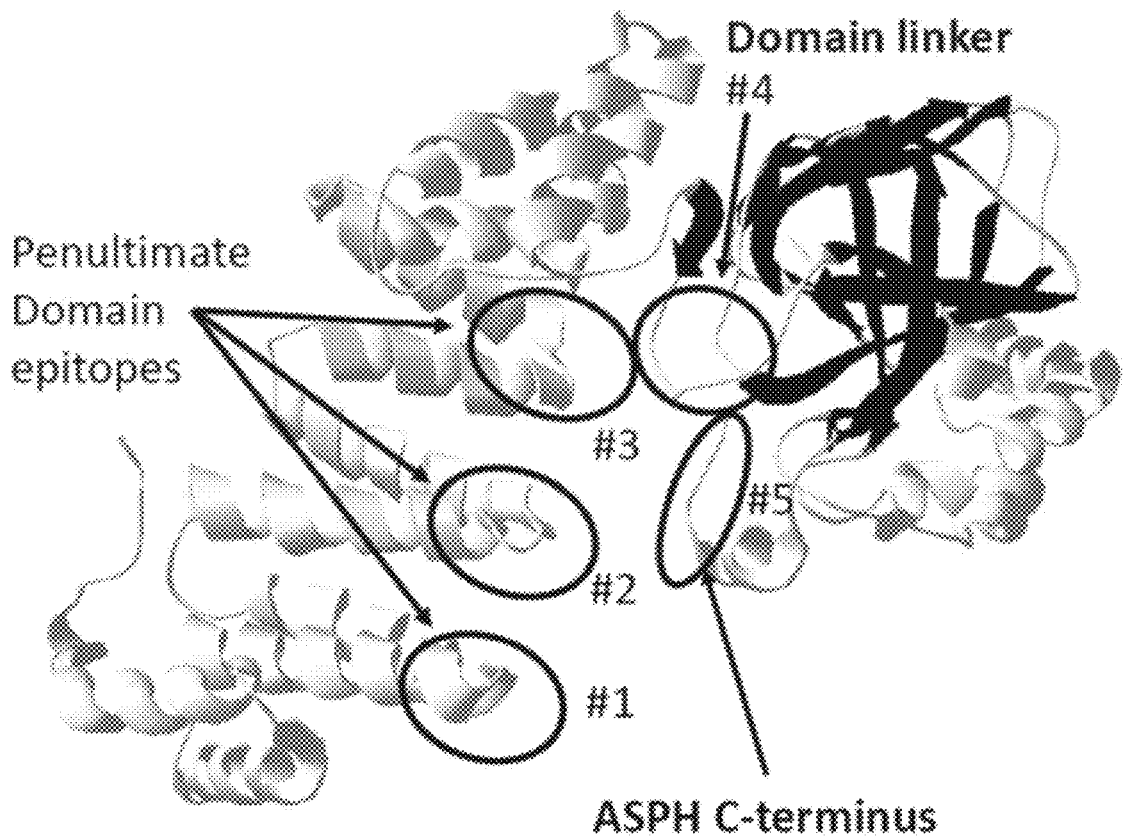

Figure 2A

Peptide Domains:

```
#1 HUMAN/CANINE:   KKRSNEVLR           (SEQ ID NO: 03 / 11 )
#2 HUMAN/CANINE:   DRQQFLGHM           (SEQ ID NO: 04 / 12 )
#3 HUMAN      :    GYLLIGDNDN          (SEQ ID NO: 05      )
         CANINE:   GYLLIGDNNN          (SEQ ID NO:      13 )
                          *
#4 HUMAN      :    562RSLYNVNG569      (SEQ ID NO: 06      )
         CANINE:   RSLYNVHG            (SEQ ID NO:      14 )
                        *
#5 HUMAN      :    749PQQRRSLPAI758    (SEQ ID NO: 07      )
         CANINE:   PQQRHSLPAI          (SEQ ID NO:      15 )
                      *
#6 HUMAN/CANINE:   FLPEDENLRE          (SEQ ID NO: 08 / 16 )
#7 HUMAN/CANINE:   VWPHTGPTNC          (SEQ ID NO: 09 / 17 )
#8 HUMAN      :    LWQQGRRNE           (SEQ ID NO: 10      )
#8       CANINE:   LWQQGRKNE           (SEQ ID NO:      18 )
                        *
```

Locations #6, #8, and #7, respectively, are between #4 and #5.

Figure 2B

Locations of Epitopes of Interest on the Sequence of Human ASPH

```
ID   ASPH_HUMAN               Reviewed;         758 AA.
AC   Q12797; A0A0A0MSK8; A6NDF4; A6NHI2; B4DIC9; B4E2K4; B7ZM95; E5RGP5;
AC   F5H667; Q6NXR7; Q8TB28; Q9H291; Q9H2C4; Q9NRI0; Q9NRI1; Q9Y4J0;
DT   01-NOV-1997, integrated into UniProtKB/Swiss-Prot.
DT   17-APR-2007, sequence version 3.
DT   25-APR-2018, entry version 181.

[. . .Text omitted. . .]

SQ   SEQUENCE   758 AA;  85863 MW;  4AE56D1D8DF0AF0C CRC64;

MAQRKNAKSS GNSSSSGSGS GSTSAGSSSP GARRETKHGG HKNGRKGGLS GTSFFTWFMV  60
     IALLGVWTSV AVVWFDLVDY EEVLGKLGIY DADGDGDFDV DDAKVLLGLK ERSTSEPAVP 120
     PEEAEPHTEP EEQVPVEAEP QNIEDEAKEQ IQSLLHEMVH AEHVEGEDLQ QEDGPTGEPQ 180
     QEDDEFLMAT DVDDRFETLE PEVSHEETEH SYHVEETVSQ DCNQDMEEMM SEQENPDSSE 240
     PVVEDERLHH DTDDVTYQVY EEQAVYEPLE NEGIEITEVT APPEDNPVED SQVIVEEVSI 300
     FPVEEQQEVP PETNRKTDDP EQKAKVKKKK PKLLNKFDKT IKAELDAAEK LRKRGKIEEA 360
                                      Peptide #H1<391.399>
     VNAFKELVRK YPQSPRARYG KAQCEDDLAE KRRSNEVLRG AIETYQEVAS LPDVPADLLK 420
 Peptide #H2<428..436>                Peptide #H3<463...470>
     LSLKRRSDRQ QFLGHMRGSL LTLQRLVQLF PNDTSLKNDL GVGYLLIGDN DNAKKVYEEV 480
     LSVTPNDGFA KVHYGFILKA QNKIAESIPY LKEGIESGDP GTDDGRFYFH LGDAMQRVGN 540
                Peptide #H4<562569>
     KEAYKWYELG HKRGHFASVW QRSLYNVNGL KAQPWWTPKE TGYTELVKSL ERNWKLIRDE 600
      Peptide #H6<612...621>   #H8<630..638>
     GLAVMDKAKG LFLPEDENLR EKGDWSQFTL WQQGRRNENA CKGAPKTCTL LEKFPETTGC 660
            Peptide #H7<676...685>
     RRGQIKYSIM HPGTHVWPHT GPTNCRLRMH LGLVIPKEGC KIRCANETKT WEEGKVLIFD 720
                       Peptide #H5<749...758>
     DSFEHEVWQD ASSFRLIFIV DVWHPELTPQ QRRSLPAI                         758
//
```

Figure 3

Experimentally confirmed and computationally-predicted substrates of ASPH
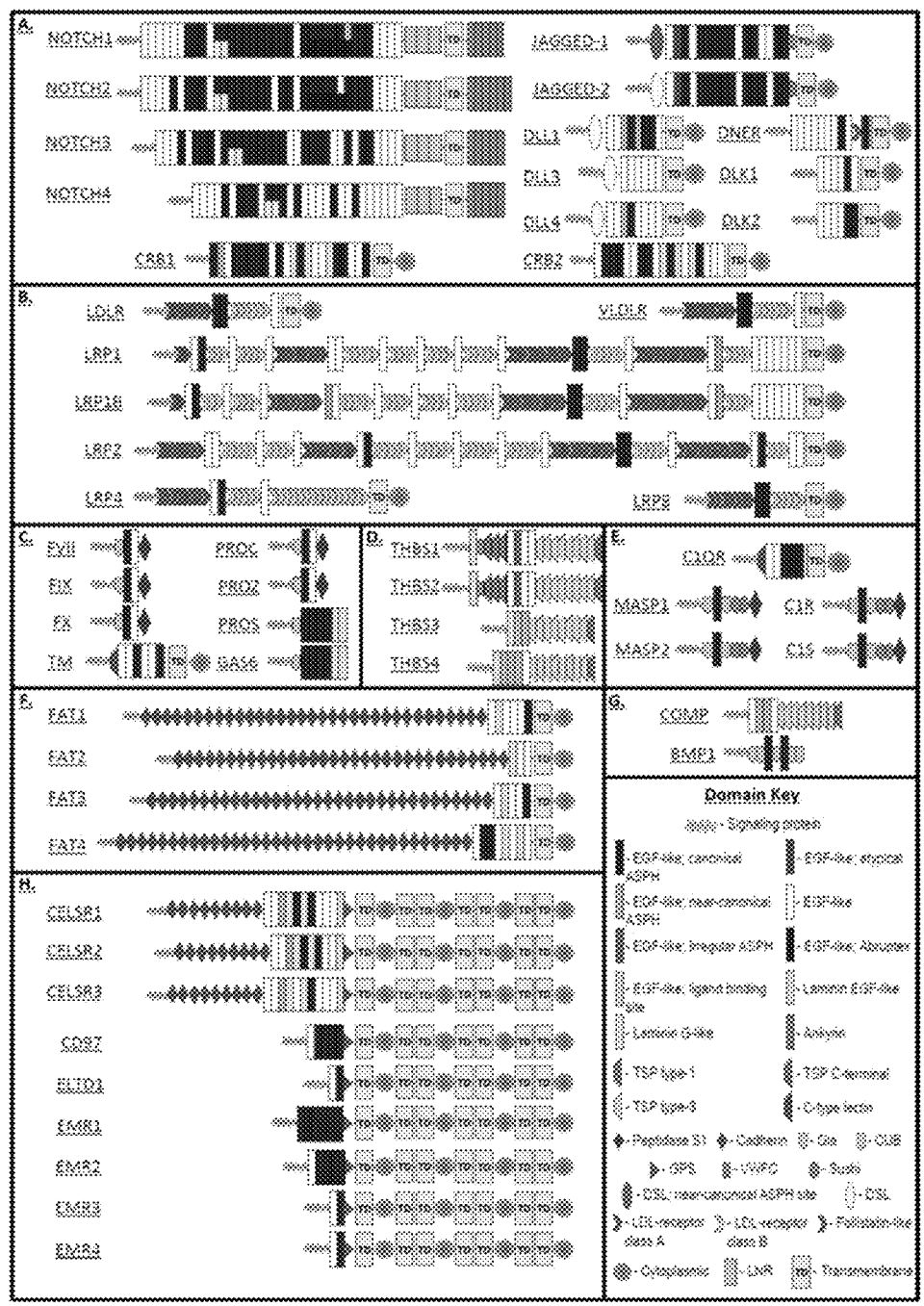
Figure 4 (Panels A-G, plus domain key)

Experimentally confirmed and computationally-predicted substrates of ASPH (continued)
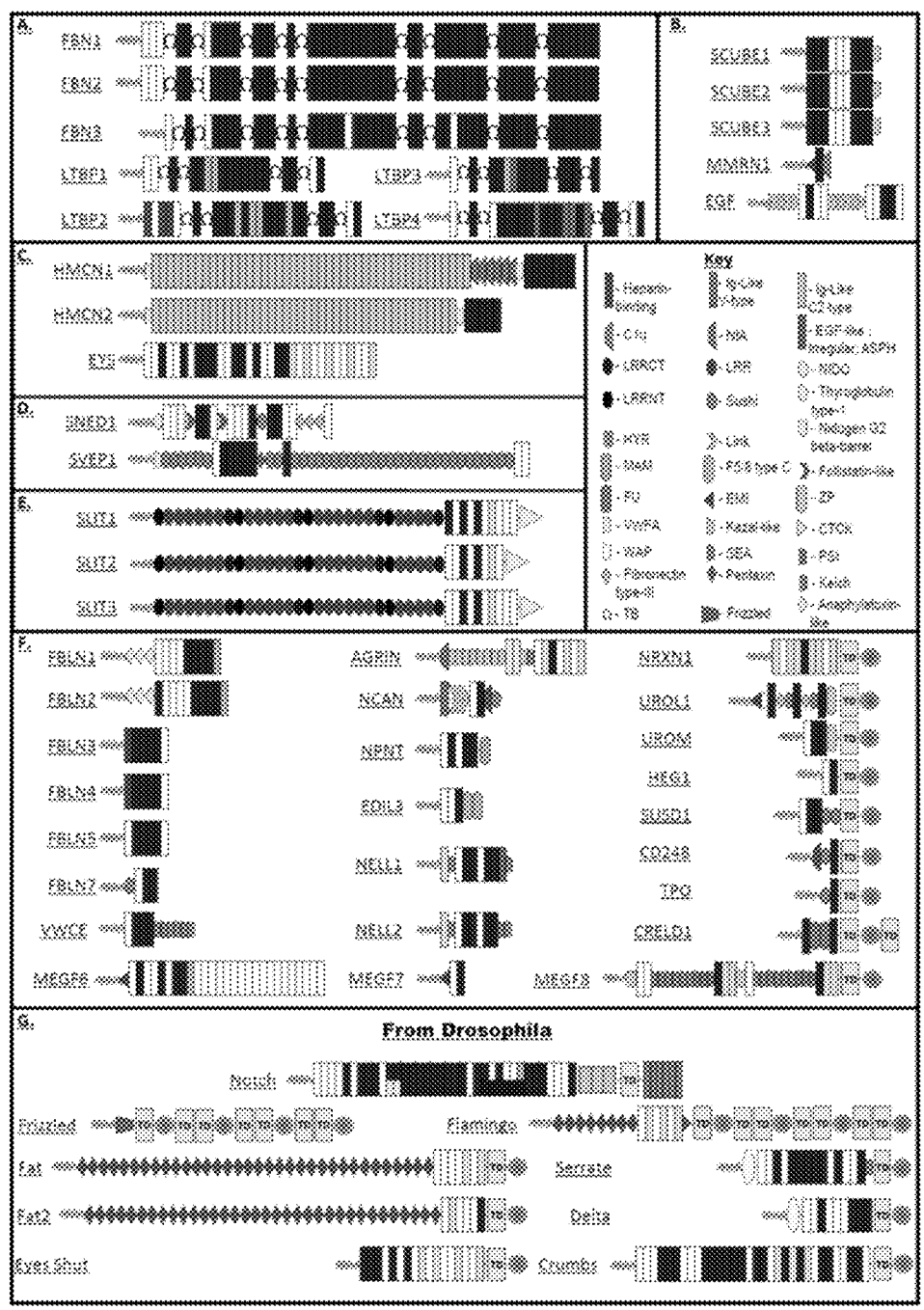
Figure 5 (panels A-G, plus domain key)

Positive 5H4/5K3 staining was visualized with DAB (brown) on Human Hepatocellular Carcinoma at 4 μg/ml, 8 μg/ml, and 10 μg/ml (3 images).

No-primary negative control was performed to identify nonspecific secondary binding (Neg, bottom right image).

The scale bar represents 20 μm.

Immunohistochemistry (IHC) 9H2/9K1 Phase II Optimization

Positive 9H2/9K1 staining was visualized with DAB (brown) on
Human Hepatocellular Carcinoma at 4 µg/ml, 8 µg/ml, and 10 µg/ml (3 images).

No-primary negative control was performed to identify
nonspecific secondary binding (Neg, bottom right image).

The scale bar represents 20 µm.

5H4/5K3 Phase III on TMAs (LV12 Core F4)
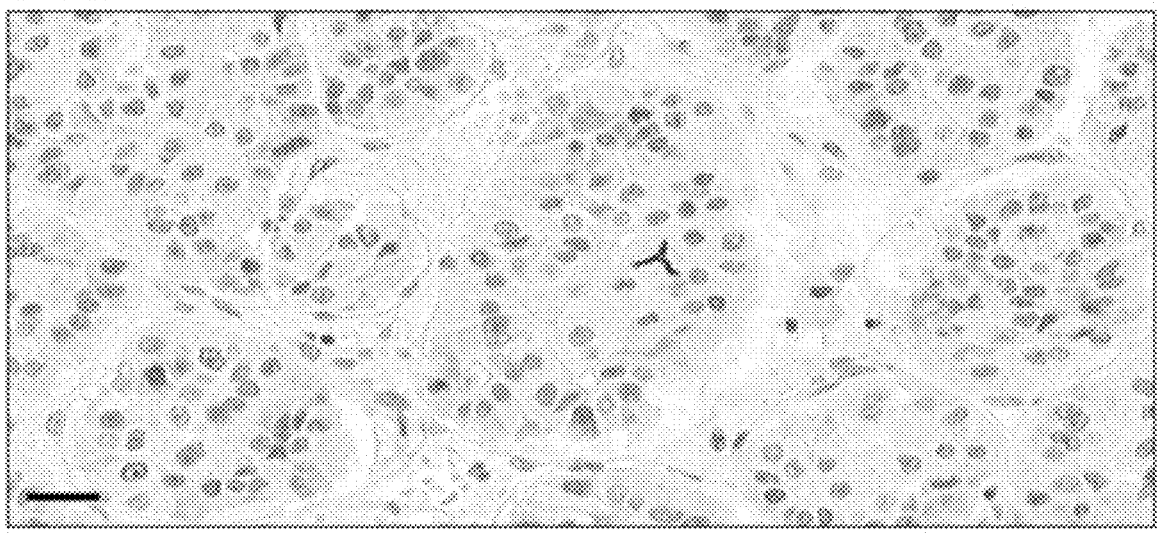
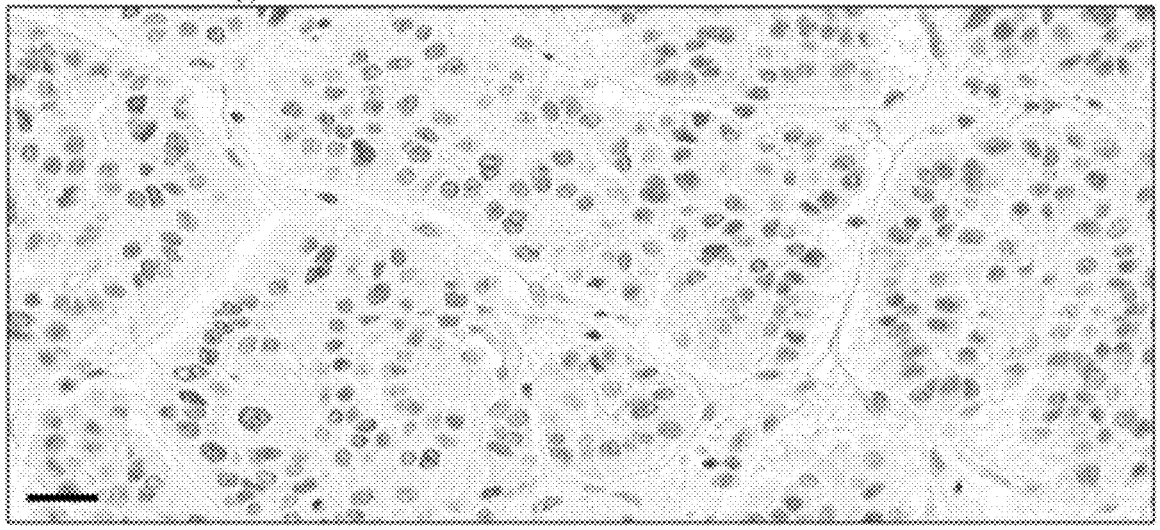
Positive 5H4/5K3 staining was visualized with DAB (brown)
on TMAs (LV12 Core F4, top image).
Isotype negative control was performed with Rabbit IgG (bottom image).
The scale bar represents 20 μm.
Figure 8

5H4/5K3 Phase III on TMAs (PC02 Core A6)
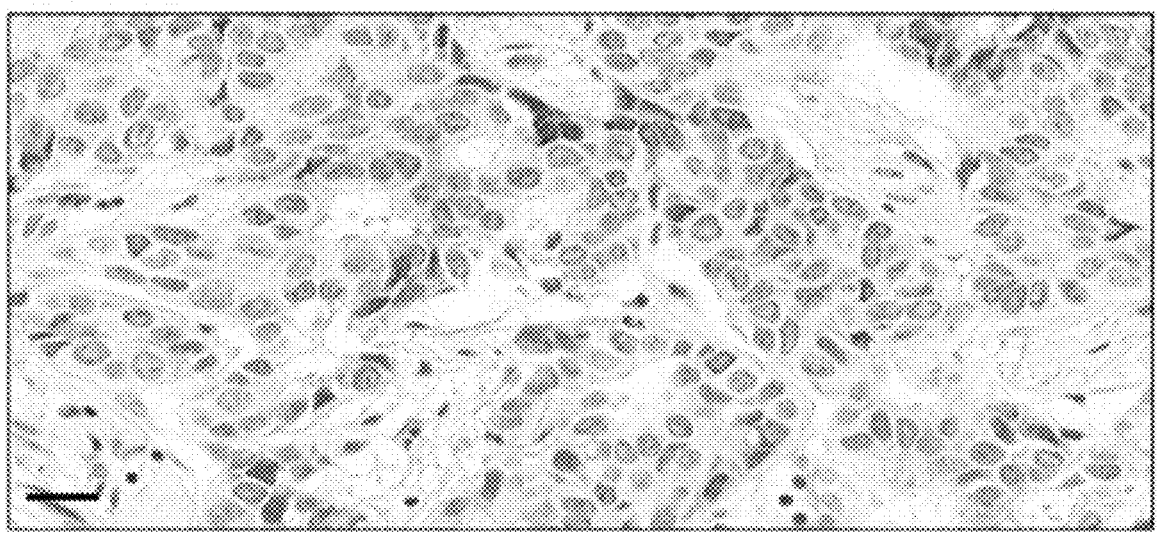
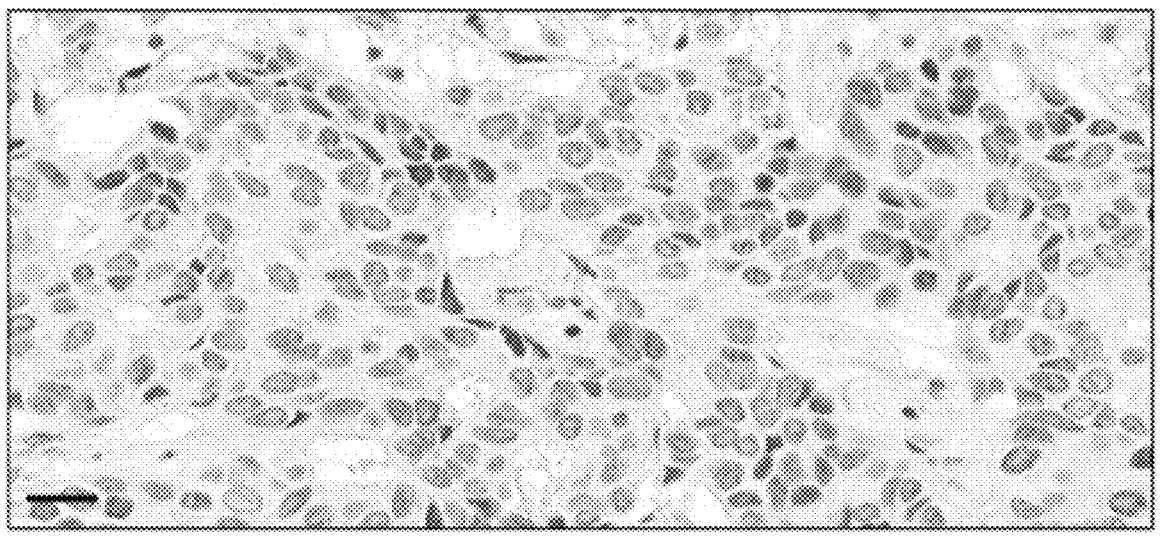
Positive 5H4/5K3 staining was visualized with DAB (brown)
on TMAs (PC02 Core A6, top image)
Isotype negative control was performed with Rabbit IgG (bottom image).
The scale bar represents 20 μm.
Figure 9

5H4/5K3 Phase III on TMAs (OV03 Core C5)
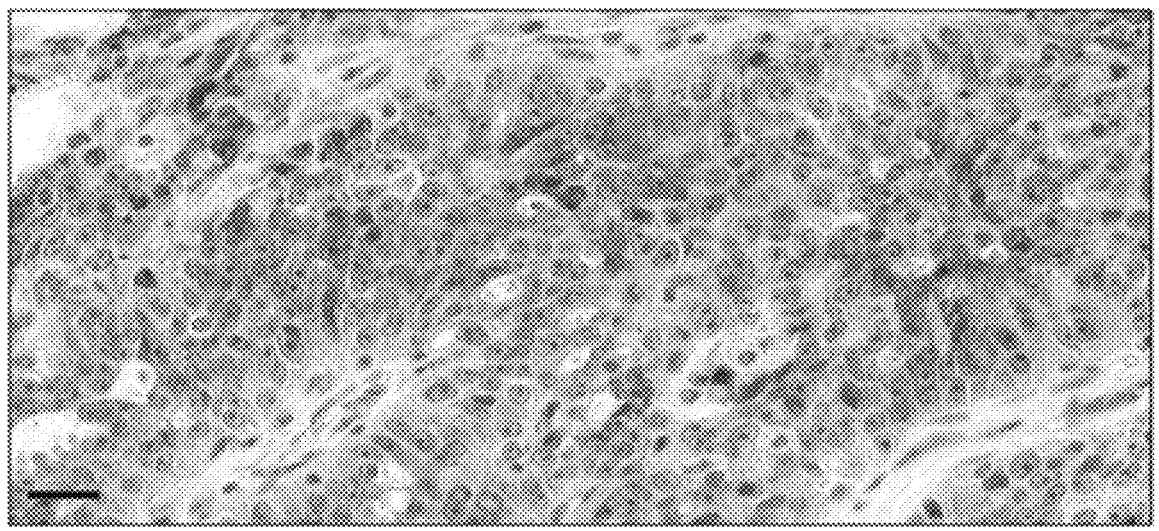
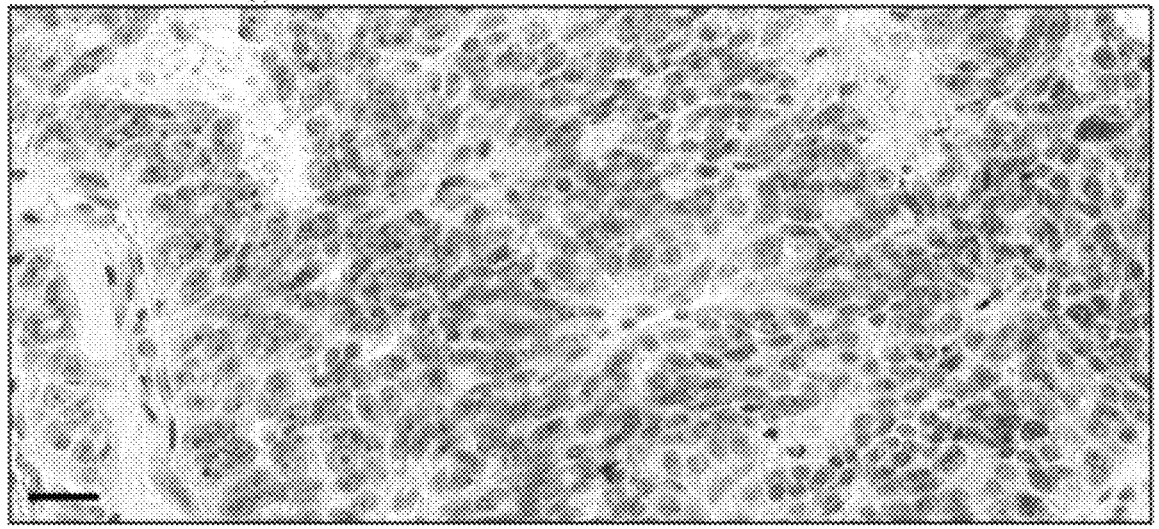
Positive 5H4/5K3 staining was visualized with DAB (brown)
on TMAs (OV03 Core C5, top image)
Isotype negative control was performed with Rabbit IgG (bottom image).
The scale bar represents 20 µm.
Figure 10

5H4/5K3 Phase III on TMAs (OV01 Core D2)
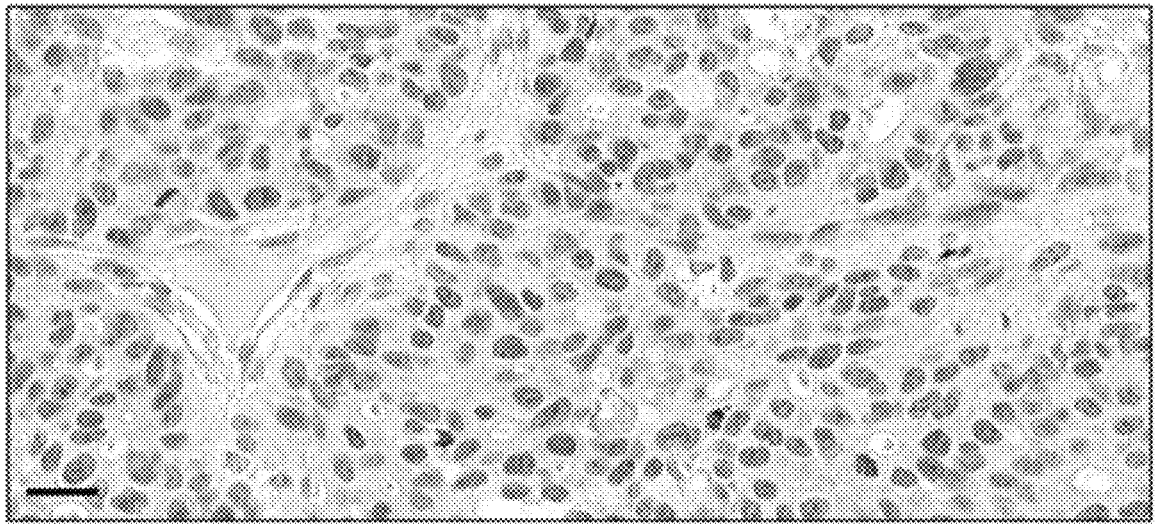
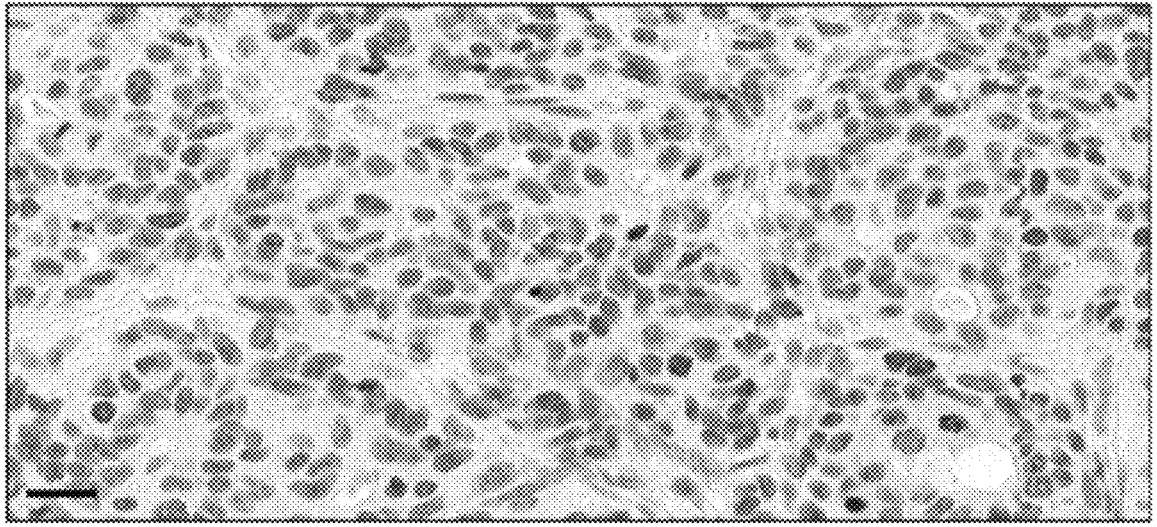
Positive 5H4/5K3 staining was visualized with DAB (brown)
on TMAs (OV01 Core D2, top image)
Isotype negative control was performed with Rabbit IgG (bottom image).
The scale bar represents 20 μm.
Figure 11

Positive 5H4/5K3 staining was visualized with DAB (brown)
Against Granulosa Cell Tumor (top images, A11 and B11)

Isotype negative control was performed with Rabbit IgG
(bottom images, A11 and B11).

Positive 5H4/5K3 staining was visualized with DAB (brown)
Against Serrous Cystadenocarcinoma Stage III (top images, C5 and D5)
Isotype negative control was performed with Rabbit IgG
(bottom images, C5 and D5).

Figure EX-10C-F9: 5H4/5K3 Against Against Serrous Cystadenocarcinoma Stage III (C8 and D8)

Positive 5H4/5K3 staining was visualized with DAB (brown)
Against Serrous Cystadenocarcinoma Stage III (top images, C8 and D8)

Isotype negative control was performed with Rabbit IgG
(bottom images, C8 and D8).

5H4/5K3 Against Endometrioid Adenocarcinoma Stage III (E8 and F8)

Positive 5H4/5K3 staining was visualized with DAB (brown)
Against Endometrioid Adenocarcinoma Stage III (top images, E8 and F8)

Isotype negative control was performed with Rabbit IgG
(bottom images, E8 and F8).

Lack of 5H4/5K3 staining by DAB
Against Normal Ovarian Tissue (top images, A1 and B1)

Isotype negative control was performed with Rabbit IgG
(bottom images, A1 and B1).

Interaction of ASPH with Mock sample

Concentrations are 500 nM (dark red, top line on right portion), 250 nM (light green), 125 nM (blue), 62.5 nM (dark green)

31.2 nM (orange), and 15.6 nM (red).

Interaction of ASPH with 2H4/2K5

Concentrations are 500 nM (dark red, 1st line from top), 250 nM (light green, 2nd and 3rd lines from top), 125 nM (blue, 4th and 5th lines from top), and 62.5 nM (dark green, 6th and 7th lines from top).

Interaction of ASPH with 5H1/5K1

Concentrations are 500 nM (dark red, 1st line from top), 250 nM (light green, 2nd and 3rd lines from top), 125 nM (blue, 4th and 5th lines from top), 62.5 nM (dark green, 6th and 7th lines from top)

31.2 nM (orange, 8th and 9th lines from top), and 15.6 nM (red, 10th and 11th lines from top).

Interaction of ASPH with 5H4/5K3

Concentrations are 500 nM (dark red, 1st and 2nd lines from top), 250 nM (light green, 3rd and 4th lines from top), 125 nM (blue, 5th and 6th lines from top), 62.5 nM (dark green, 7th and 8th lines from top), 31.2 nM (orange, 9th and 10th lines from top), and 15.6 nM (red, 11th and 12th lines from top).

Interaction of ASPH with 9H2/9K1

Concentrations are 500 nM (dark red, 1st and 2nd lines from top), 250 nM (light green, 3rd and 4th lines from top), 125 nM (blue, 5th and 6th lines from top), 62.5 nM (dark green, 7th and 8th lines from top), 31.2 nM (orange, 9th and 10th lines from top), and 15.6 nM (red, 11th and 12th lines from top).

Interaction of ASPH with 9H2/9K3

Concentrations are 500 nM (dark red, 1st line from top), 250 nM (light green, 2nd and 3rd lines from top), 125 nM (blue, 4th and 5th lines from top), 62.5 nM (dark green, 6th line from top), and 31.2 nM (orange, 7th line from top).

Interaction of ASPH with 8H1/8K1

Concentrations are 500 nM (dark red, 1st and 2nd lines from top), 250 nM (light green), 125 nM (blue), 62.5 nM (dark green), 31.2 nM (orange), and 15.6 nM (red).

METHODS OF USING MONOCLONAL ANTIBODIES TARGETING EPITOPES OF ASPH

CROSS REFERENCE TO RELATED APPLICATIONS

This is a divisional application that claims priority to and the benefit of U.S. Non-Provisional application Ser. No. 16/444,617, filed Jun. 18, 2019, and U.S. Provisional Application No. 62/686,107, filed Jun. 18, 2018, the entire contents of which are incorporated by reference in their entirety.

INCORPORATION-BY-REFERENCE OF A SEQUENCE LISTING

The Sequence Listing contained in the files "761_190_033_US_01_Sequence_Listing_ST25.txt", created on 2020 Sep. 1, modified on 2020 Sep. 1, file size 44,370 bytes, containing SEQ ID NOS: 1-52, "761_190_026_US_Sequence_Listing_ST25.txt", created on 2019 May 21, modified on 2019 May 21, file size 35,033 bytes, containing SEQ ID NOS: 1-30, and "761_190_025_US_Sequence_Listing_ST25.txt", created on 2018 Jun. 17, modified on 2018 Jun. 17, file size 34,990 bytes, containing SEQ ID NOS: 1-30, are incorporated by reference in its entirety herein.

FIELD OF THE INVENTION

Monoclonal antibodies (MAbs) targeting one or more specific epitopes of aspartyl (asparaginyl) β-hydroxylase (ASPH), including humanized, bi-specific, and other chimeric MAb variants, and fragments thereof (collectively ASPH epitope-specific MAbs, or simply ASPH MAbs), are disclosed. Methods of production, purification, and use of the ASPH epitope-specific MAbs, and compositions comprising them, as agents in therapeutic and diagnostic applications to interact with target molecules in cell-free samples, cell- and tissue-based assays, animal models, and in a subject are also disclosed. Other aspects of the invention relate to use of the molecules disclosed herein to diagnose, ameliorate, or treat cell proliferation disorders and related diseases.

BACKGROUND OF THE INVENTION

Aspartyl(asparaginyl)-β-hydroxylase (ASPH) is an iron-dependent dioxygenase that catalyzes the hydroxylation of 13 carbons of aspartic acid and asparagine residues in calcium binding Epidermal Growth Factor (cbEGF)-like domains of a variety of proteins, including Notch and Notch ligand homologs (Dinchuk, Focht et al. 2002) extracellular matrix proteins, and low density lipoprotein (LDL) receptors. ASPH was first observed to be involved in the hydroxylation of a specific aspartic acid residue in the blood coagulation cascade proteins (Drakenberg, Fernlund et al. 1983) where the hydroxylated residue is underlined in the consensus sequence CX[D/N]X₄[Y/F]XC. The role of hydroxylated residue is presently unknown, but the sole known crystal structure with a beta-hydroxylated asparagine (PDB ID 5JZZ: McDonough, M. A., Pfeffer, I., and Munzel (2016) Aspartyl/Asparaginyl beta-hydroxylase (AspH)oxygenase and TPR domains in complex with manganese, N-oxalylglycine and cyclic peptide substrate mimic of factor X. DOI: 10.2210/pdb5JZZ/pdb).

ASPH is generally classified as a peptide-aspartate beta-dioxygenase (EC 1.14.11.16), a member of the alpha-keto-glutarate-dependent hydroxylases superfamily, which catalyzes the following chemical reaction, facilitated by iron as a cofactor.

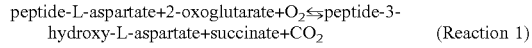
(Reaction 1)

ASPH is not normally expressed in adult cells (Lavaissiere, Jia et al. 1996), but is expressed during invasion of the uterine wall by trophoblasts during development of the placenta (Gundogan, Elwood et al. 2007). ASPH is overexpressed in a variety of tumors, including hepatocellular, cholangiocarcinoma, gastric cancer, pancreatic cancer, non-small cell lung cancer, glioblastoma multiform, osteosarcoma, cervical cancer, ovarian cancer and breast cancer (Yang, Song et al. 2010), and enhances signaling in the Notch pathway (Cantarini, de la Monte et al. 2006).

FIG. 1 sets forth an illustration showing the Activation of Notch Signaling Pathway by ASPH. FIGS. 2 and 3 set forth illustrations showing the Locations of Epitopes of Interest on ASPH.

Known and computationally predicted ASPH substrates are illustrated in FIG. 4 and FIG. 5. Prediction of ASPH substrates is based upon the protein possessing A) a cbEGF domain and B) the consensus sequence CX[D/N]X₄[Y/F]XC. Of particular interest are nearly all of the Notch signaling proteins, not only including the receptors Notch1-4, but many of the known ligands such as Jagged1&2 and DII1&4, but also known Notch pathway modulator human homologues of Crumbs from *Drosophila*. ASPH is known to hydroxylate lipid receptor proteins, including Lrp1. Lrp1 is known to have an interaction with Wnt5a of the canonical Wnt signaling pathway (El Asmar, Terrand et al. 2016). ASPH substrate Gas6 is the ligand of the Tyro3, Axel and Mer (TAM) kinases, which have been implicated in cancer (Wu, Ma et al. 2018). Known ASPH substrates including the fibrillins are involved in the release of TGF-beta, which is implicated in cancer (Furler, Nixon et al. 2018). In addition to cancer, ASPH hydroxylated substrates are found in nearly all of the blood coagulation proteins involved in thrombosis (see panel C in FIG. 4), and many of the proteins involved in lipid uptake including LDLR, VLDLR and Lrp1 (see panel B in FIG. 4) and cholesterol homeostasis. Thus, ASPH expression is expected to have a cascade of effects, but may have particular value in the treatment of cancer, as well as thrombosis and lipid/cholesterol associated cardiovascular diseases.

ASPH is known to contain multiple phosphorylation sites (Tong, Gao et al. 2013), including T748. Phosphorylation of ASPH is known to alter the expression and function of ASPH (Borgas, Gao et al. 2015), and plays a potential role in migration and tissue invasion of hepatocellular carcinoma (Borgas, Gao et al. 2015). Antibodies selective for ASPH phosphorylation state should be useful in the diagnosis of cancer and distinguishing normally expressed ASPH from tumor expressed ASPH.

Previously designed antibodies to ASPH did not result in direct suppression of tumor cell proliferation (Yeung, Finney et al. 2007). Despite the high affinity of these antibodies, the targeted epitope did not sufficiently disrupt catalytic activity of ASPH. Consequently, while the antibodies were internalized into the cancer cells expressing ASPH, there was no direct antibody activity leading to cellular senescence or cytotoxicity. To address this issue, radioisotopes have been conjugated to previously described high affinity ASPH antibodies, leading to modest activity (Revskaya, Jiang et al. 2017). Other previous anti-ASPH strategies include small molecule inhibitors of ASPH (Aihara, Huang et al. 2014), a dendritic cell approach (Noda, Shimoda et al. 2012), and a vaccine approach (Iwagami, Casulli et al. 2017).

This application describes the epitope selection for phospho-selective ASPH antibodies, as well as antibodies for ASPH catalytic activity inhibition, including epitopes on both the catalytic and non-catalytic domains, demonstration of high affinity for ASPH, strong IHC staining of cancerous but not normal tissue, and direct activity against cancer cells.

SUMMARY OF THE INVENTION

The present invention relates to monoclonal antibodies (MAbs) targeting one or more specific epitopes of aspartyl (asparaginyl) β-hydroxylase (ASPH), including chimeric and humanized MAb variants, and fragments thereof (collectively ASPH epitope-specific MAbs, or simply ASPH MAbs), are disclosed. Methods of production, purification, and use of the ASPH epitope-specific MAbs, and compositions comprising them, as agents in therapeutic and diagnostic applications to interact with target molecules in cell-free samples, cell- and tissue-based assays, animal models, and in a subject are also disclosed. Other aspects of the invention relate to use of the molecules disclosed herein to diagnose, ameliorate, or treat cell proliferation disorders and related diseases.

One aspect relates to an isolated monoclonal antibody, or a fragment thereof, which binds to a one or more peptide epitopes of human aspartyl (asparaginyl) β-hydroxylase (ASPH), wherein at least one of said peptide epitopes is located within or adjacent to the catalytic domain of ASPH.

Another aspect relates to a composition comprising any of the antibodies noted above, including compositions comprising at least one antibody that targets ASPH and one or more pharmaceutical excipients.

Another aspect relates to a method of using any of the antibodies noted above, to inhibit the proliferation of isolated tumor cell samples grown in culture.

Another aspect relates to a method of using any of the antibodies noted above, to inhibit the proliferation of tumor cells in tissue samples grown in culture.

Another aspect relates to a method of treating cancer in a mammalian subject, comprising administering to a subject in need thereof an antibody as noted above in an amount sufficient to treat cancer.

Another aspect relates to a kit for diagnosis of cancer in a mammalian subject, wherein said kit comprises an antibody, or a fragment thereof, of any of any of the antibodies noted above.

Another aspect relates to a humanized antibody comprising one or more complementarity determining regions (CDRs) derived from a non-human source targeting one or more peptide epitopes located within or adjacent to the catalytic domain of ASPH of any of the antibodies noted above, and one or more portions of the constant regions of a human antibody, and fragments thereof.

Another aspect relates to a bispecific antibody comprising one or more complementarity determining regions (CDRs) derived from a non-human source targeting one or more peptide epitopes located within or adjacent to the catalytic domain of ASPH of any of the antibodies noted above, and an antibody targeting other epitopes selected from the group consisting of the T-cell redirector class, comprising an antibody targeting one or more ASPH CDRs and an antibody targeting CD3; the NK-cell redirector class, comprising an antibody targeting one or more ASPH CDRs and an antibody targeting CD16A; the tumor targeting immunomodular class, comprising an antibody targeting one or more ASPH CDRs and an antibody targeting CD40 or 4-1BB; and the dual immunomodular class, comprising an antibody targeting one or more ASPH CDRs and an antibody targeting PD-L1, PD-1, CTLA-4, TGF-β, LAG-3, TIM-3, or OX40.

A better understanding of the invention will be obtained from the following detailed descriptions and accompanying drawings, which set forth illustrative embodiments that are indicative of the various ways in which the principals of the invention may be employed.

BRIEF DESCRIPTION OF THE DRAWINGS

Statement Concerning Aspects of the Invention Understood by Reference to the Drawings The foregoing aspects and many of the attendant advantages of this invention will become more readily appreciated as the same become better understood by reference to the following detailed description, when taken in conjunction with the accompanying drawings, wherein:

FIG. 1 sets forth an illustration showing the Activation of Notch Signaling Pathway by ASPH. Aspartyl(asparaginyl)-β-hydroxylase (ASPH) is an iron-dependent dioxygenase that catalyzes the hydroxylation of 13 carbons of aspartic acid and asparagine residues in domains of a variety of proteins, including Notch and Notch ligand homologs. Intense activation of the Notch pathway by ASPH is observed in tumor tissues. Inhibition of ASPH allows normal activation of the Notch Pathway.

FIG. 2A sets forth an illustration showing the Locations of Epitopes of Interest on Human ASPH (3D Structure). FIG. 2B lists peptide domain sequences.

FIG. 3 sets forth an illustration showing the Locations of Epitopes of Interest on the Sequence of ASPH.

FIG. 4 (Panels A-H, plus a polypeptide domain key) sets forth an illustration showing experimentally confirmed and computationally predicted substrates of ASPH, including those found in the following types of proteins: A. Notch signaling pathway, B. Lipid receptors, C. Blood coagulation cascade proteins, D. Thrombospondins, E. Complement cascade proteins, F. FAT cadherin domain proteins, G. Bone associated proteins, and H. 7-transmembrane domain containing proteins.

FIG. 5 (Panels A-G, plus a polypeptide domain key) sets forth an illustration showing experimentally confirmed and computationally predicted substrates of ASPH (continued), including those found in the following types of proteins: A. TGF-b containing proteins, B. Platelet associated proteins, C. Eye/retina associated proteins, D. Mammary cancer metastasis proteins, E. Slit proteins, F. Miscellaneous proteins, and G. *Drosophila* homologues.

FIG. 8 sets forth an illustration demonstrating 5H4/5K3 Phase III on TMAs for samples labeled as LV12 Core F4 (top image), and LV12 Core F4-Isotype (bottom image). Positive 5H4/5K3 staining was visualized with DAB (brown) on TMAs (LV12 Core F4, top image). Isotype negative control was performed with Rabbit IgG (bottom image). The scale bar represents 20 μm.

FIG. 9 sets forth an illustration demonstrating 5H4/5K3 Phase III on TMAs for samples labeled as PCO2 Core A6 (top image), and PCO2 Core A6-Isotype (bottom image). Positive 5H4/5K3 staining was visualized with DAB (brown, top image). Isotype negative control was performed with Rabbit IgG (bottom image). The scale bar represents 20 μm.

FIG. 10 sets forth an illustration demonstrating 5H4/5K3 Phase III on TMAs for samples labeled as OV03 Core C5 (top image), and OV03 Core C5-Isotype (bottom image). Positive 5H4/5K3 staining was visualized with DAB (brown, top image). Isotype negative control was performed with Rabbit IgG (bottom image). The scale bar represents 20 μm.

FIG. 11 sets forth an illustration demonstrating 5H4/5K3 Phase III on TMAs for samples labeled as OV01 Core D2 (top image), and OV01 Core D2-Isotype (bottom image). Positive 5H4/5K3 staining was visualized with DAB (brown, top image). Isotype negative control was performed with Rabbit IgG (bottom image). The scale bar represents 20 μm.

TABLE #T0

Figure 6:
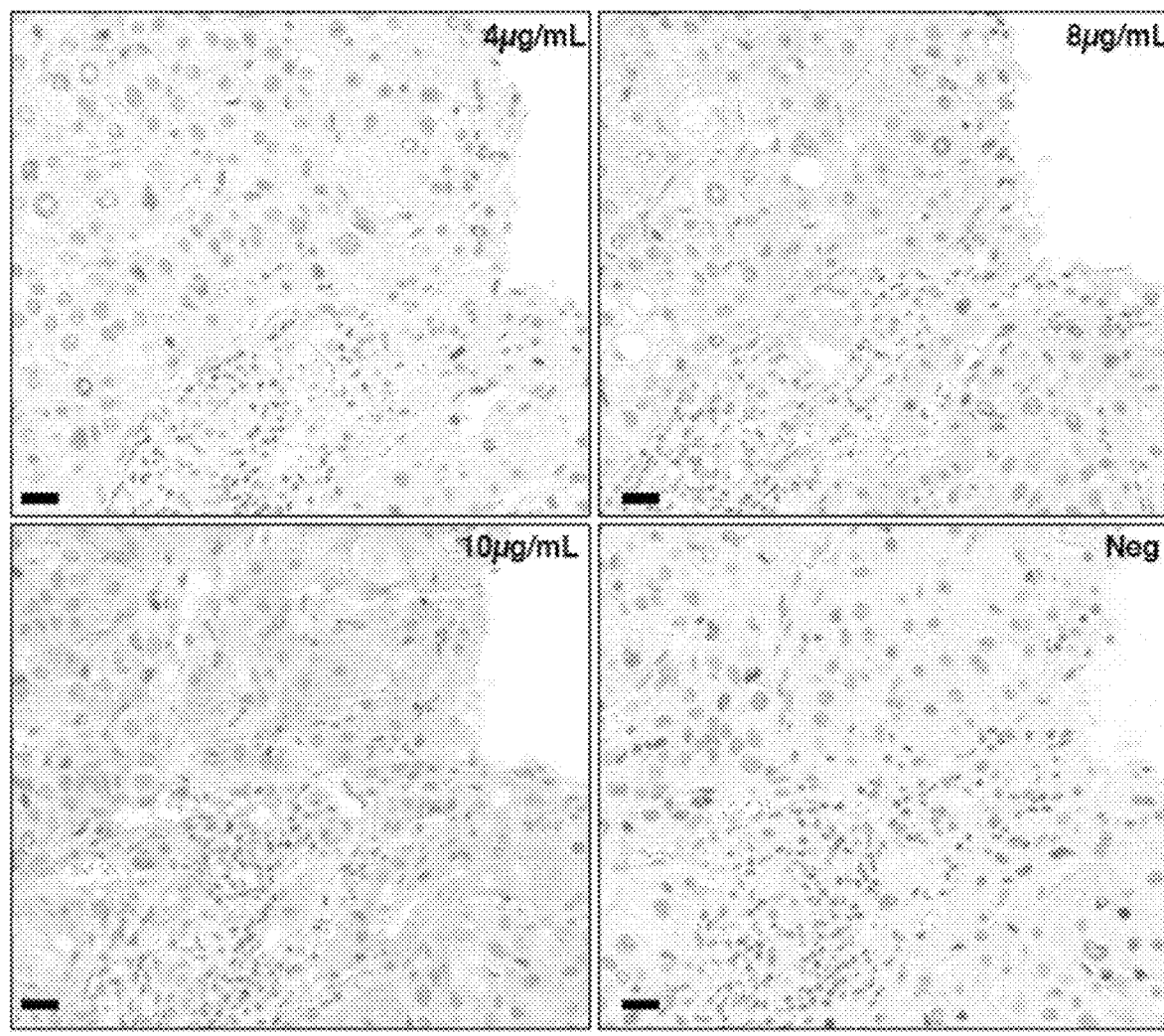
FIG. 6 sets forth an illustration demonstrating positive 5H4/5K3 staining visualized with DAB (brown) on Human Hepatocellular Carcinoma at 4 μg/ml, 8 μg/ml, and 10 μg/ml (3 images). No-primary negative control was performed to identify nonspecific secondary binding (Neg, bottom right image). The scale bar represents 20 μm.

Summary of Staining Patterns in Panels of Photographic Images of Cell Samples (from +++ to −)*

| Figure | Description | Top/Top Left | Top Right | Bottom/Bottom Left | Bottom Right |
|---|---|---|---|---|---|
| 6 | Positive 5H4/5K3 staining visualized with DAB (brown) on Human Hepatocellular Carcinoma at 4 μg/ml, 8 μg/ml, and 10 μg/ml (3 images). | + | ++ | +++ | − |

TABLE #T0-continued

Summary of Staining Patterns in Panels of Photographic Images of Cell Samples (from +++ to −)*

| Figure | Description | Top/Top Left | Top Right | Bottom/Bottom Left | Bottom Right |
|---|---|---|---|---|---|
|  | No-primary negative control was performed to identify nonspecific secondary binding (Neg, bottom right image). |  |  |  |  |
| 7 | Positive 9H2/9K1 staining visualized with DAB (brown) on Human Hepatocellular Carcinoma at 4 μg/ml, 8 μg/ml, and 10 μg/ml (3 images). No-primary negative control was performed to identify nonspecific secondary binding (Neg, bottom right image). | (+) | + | ++ | − |
| 8 | 5H4/5K3 Phase III on TMAs for samples labeled as LV12 Core F4 (top image), and LV12 Core F4 - Isotype (bottom image). | +++ |  | − |  |
| 9 | 5H4/5K3 Phase III on TMAs for samples labeled as PC02 Core A6 (top image), and PC02 Core A6 - Isotype (bottom image). Positive 5H4/5K3 staining was visualized with DAB (brown,, top image). Isotype negative control was performed with Rabbit IgG (bottom image). | +++ |  | − |  |
| 10 | 5H4/5K3 Phase III on TMAs for samples labeled as OV03 Core C5 (top image), and OV03 Core C5 - Isotype (bottom image). Positive 5H4/5K3 staining was visualized with DAB (brown, top image). Isotype negative control was performed with Rabbit IgG (bottom image). | +++ |  | − |  |
| 11 | 5H4/5K3 Phase III on TMAs for samples labeled as OV01 Core D2 (top image), and OV01 Core D2 - Isotype (bottom image). Positive 5H4/5K3 staining was visualized with DAB (brown, top image). Isotype negative control was performed with Rabbit IgG (bottom image). | +++ |  | − |  |
| 12 | Activity of 5H4/5K3 Against Granulosa Cell Tumor Samples (A11 and B11). Positive 5H4/5K3 staining was visualized with DAB (brown) Against Granulosa Cell Tumor (top images, A11 and B11) Isotype negative control was performed with Rabbit IgG (bottom images, A11 and B11). | ++ | ++ | − | − |
| 13 | Activity of 5H4/5K3 Against Serrous Cystadenocarcinoma Stage III Samples (C5 and D5). Positive 5H4/5K3 staining was visualized with DAB (brown) Against Serrous Cystadenocarcinoma Stage III (top images, C5 and D5) Isotype negative control was performed with Rabbit IgG(bottom images, C5 and D5). | +++ | +++ | − | − |
| 14 | Activity of 5H4/5K3 Against Serrous Cystadenocarcinoma Stage III Samples (C8 and D8). Positive 5H4/5K3 staining was visualized with DAB (brown) Against Serrous Cystadenocarcinoma Stage III (top images, C8 and D8) Isotype negative control was performed with Rabbit IgG (bottom images, C8 and D8). | +++ | +++ | − | − |
| 15 | Activity of 5H4/5K3 Against Endometrioid Adenocarcinoma Stage III Samples (E8 and F8). Positive 5H4/5K3 staining was visualized with DAB (brown) Against Endometrioid Adenocarcinoma Stage III (top images, E8 and F8). Isotype negative control was performed with Rabbit IgG (bottom images, E8 and F8). | +++ | +++ | (−) | (−) |

TABLE #T0-continued

Summary of Staining Patterns in Panels of Photographic Images of Cell Samples (from +++ to −)*

| Figure | Description | Top/Top Left | Top Right | Bottom/ Bottom Left | Bottom Right |
|---|---|---|---|---|---|
| 16 | Reaction of 5H4/5K3 Against Normal Ovarian Tissue Samples (A1 and B1). Lack of 5H4/5K3 staining by DAB Against Normal Ovarian Tissue (top images, A1 and B1). Isotype negative control was performed with Rabbit IgG (bottom images, A1 and B1). | − | − | − | − |
| 17 | Reaction of 5H4/5K3 Against Thecoma (Theca Cell) Tumor Tissue (A5 and B5). 5H4/5K3 staining was visualized with DAB (brown, top images) Against Thecoma (Theca Cell) Tumor Tissue (A5 and B5). Isotype negative control was performed with Rabbit IgG (bottom images, A5 and B5). | (+) | (+) | − | − |

*Staining intensities of different panels for each sample were evaluated on a scale from +++, ++, +, (+), (−), and − where reaction with DAB to produce an intense brown color after reaction with cells was designated as +++, to −, where all cells were mostly blue or white.

Terms and Definitions

The following is a list of abbreviations, plus terms and their definitions, used throughout the specification and the claims:

General abbreviations and their corresponding meanings include: aa or AA=amino acid; mg=milligram(s); ml or mL=milliliter(s); mm=millimeter(s); mM=millimolar; nmol=nanomole(s); pmol=picomole(s); ppm=parts per million; RT=room temperature; U=units; μg, μg=micro gram(s); ul, μl=micro liter(s); μM, μM=micromolar.

Specific Abbreviations and their Corresponding Meanings Include

The terms "cell" and "cells", which are meant to be inclusive, refer to one or more cells which can be in an isolated or cultured state, as in a cell line comprising a homogeneous or heterogeneous population of cells, or in a tissue sample, or as part of an organism, such as a transgenic animal.

The term "amino acid" encompasses both naturally occurring and non-naturally occurring amino acids unless otherwise designated.

The term "complementarity-determining regions" or "CDRs" are defined by Wikipedia, as part of the variable chains in immunoglobulins (antibodies) and T cell receptors, generated by B-cells and T-cells respectively, where these molecules bind to their specific antigen. CDRs, which comprise the most variable parts of antibodies, are crucial to the diversity of antigen specificities generated by lymphocytes.

The term "paratope" refers to a set of CDRs.

DETAILED DESCRIPTION OF THE INVENTION

The present invention relates to monoclonal antibodies (MAbs) targeting one or more specific epitopes of aspartyl (asparaginyl) β-hydroxylase (ASPH), including chimeric and humanized MAb variants, and fragments thereof (collectively ASPH epitope-specific MAbs, or simply ASPH MAbs), are disclosed. Methods of production, purification, and use of the ASPH epitope-specific MAbs, and compositions comprising them, as agents in therapeutic and diagnostic applications to interact with target molecules in cell-free samples, cell- and tissue-based assays, animal models, and in a subject are also disclosed. Other aspects of the invention relate to use of the molecules disclosed herein to diagnose, ameliorate, or treat cell proliferation disorders and related diseases.

One aspect relates to an isolated monoclonal antibody, or a fragment thereof, which binds to a one or more peptide epitopes of human aspartyl (asparaginyl) β-hydroxylase (ASPH), wherein at least one of said peptide epitopes is located within or adjacent to the catalytic domain of ASPH.

Another aspect relates to an antibody, or a fragment thereof, as noted above, wherein at least one of said peptide epitopes located within or adjacent to the catalytic domain of ASPH is located within 30 amino acids of the C-terminus of ASPH.

Another aspect relates to an antibody, which binds to one or more synthetic peptides selected from the group consisting of (a) a synthetic peptide comprising 29 amino acids with Cysteine at its amino terminus, plus 28 amino acids corresponding to positions 731-758 at the C-terminal end of human ASPH, with the Threonine at 19 (corresponding to 748 of ASPH) phosphorylated, as CASSFRLIFIVDVWH-PEL-T(PO3H2)-PQQRRSLPAI represented by SEQ ID NO: 19; and (b) a synthetic peptide comprising 29 amino acids with Cysteine at its amino terminus, plus 28 amino acids corresponding to positions 731-758 at the C-terminal end of human ASPH, as CASSFRLI-FIVDVWHPELTPQQRRSLPAI represented by SEQ ID NO: 20.

Related aspects include an antibody, which binds to an epitope comprising at least 4 consecutive amino acid residues located within 30 amino acids from the C-terminal end of human ASPH, including an antibody wherein said epitope comprising at least 4 consecutive amino acid residues located within 30 amino acids from the C-terminal end of human ASPH comprises the consecutive amino acid selected from the group consisting of PELT represented by SEQ ID NO: 42,
ELTP represented by SEQ ID NO: 43,
LTPQ represented by SEQ ID NO: 44,
TPQQ represented by SEQ ID NO: 45,
PQQR represented by SEQ ID NO: 46,
QQRR represented by SEQ ID NO: 47,
QRRS represented by SEQ ID NO: 48, RRSL represented by SEQ ID NO: 49,
RSLP represented by SEQ ID NO: 50,
SLPA represented by SEQ ID NO: 51, and
LPAI represented by SEQ ID NO: 52.

Related aspects also include an antibody, wherein said peptide epitope comprises a phosphorylated threonine, T(PO3H2).

Another aspect relates to an isolated monoclonal antibody, or a fragment thereof, which binds to a one or more peptide epitopes of human aspartyl (asparaginyl) β-hydroxylase (ASPH), wherein said antibody comprises a recombinant heavy chain and a recombinant light chain, wherein said recombinant heavy chain comprises a polypeptide sequence selected from the group consisting of SEQ ID NOS 21-25; and wherein said recombinant light chain comprises a polypeptide sequence selected from the group consisting of SEQ ID NOS 26-30.

Another aspect relates to an antibody selected from the group consisting of 5H4/5K3 and 9H2/9K1, wherein antibody 5H4/5K3 comprises a heavy chain designated 5H4, represented by the sequence SEQ ID NO: 25, and a light chain 5K3 represented by the sequence SEQ ID NO: 27; and wherein antibody 9H2/9K1 comprises a heavy chain designated 9H2, represented by the sequence SEQ ID NO: 29, and a light chain 9K1 represented by the sequence SEQ ID NO: 30.

Another aspect relates to an isolated monoclonal antibody, or a fragment thereof, which binds to a one or more peptide epitopes of human aspartyl (asparaginyl) β-hydroxylase (ASPH), wherein said antibody comprises a recombinant heavy chain comprising:
  a CDR1 comprising a sequence selected from the group consisting of NFMC (SEQ ID NO: 31), corresponding to residues 50-53 of SEQ ID NO: 21, and NAMC (SEQ ID NO: 32), corresponding to residues 50-53 of SEQ ID NOS: 23, 29, 24, and 25;
  a CDR2 comprising a sequence selected from the group consisting of CIYF (SEQ ID NO: 33) corresponding to residues 68-71 of SEQ ID NO: 21 and CIDN (SEQ ID NO: 34) corresponding to residues 68-71 of SEQ ID NO: 23, 29, 24, and 25;
  a CDR3 comprising a sequence selected from the group consisting of DGPGSISWKI (SEQ ID NO: 35) corresponding to residues 117-126 of SEQ ID NO: 21, and NFNI (SEQ ID NO: 36) corresponding to residues 116-119 of SEQ ID NOS: 23, 29, 24, and 25.

Another aspect relates to an isolated monoclonal antibody, or a fragment thereof, which binds to a one or more peptide epitopes of human aspartyl (asparaginyl) β-hydroxylase (ASPH), wherein said antibody comprises a recombinant light chain comprising
  a CDR1 comprising a sequence selected from the group consisting of SVYSKNR (SEQ ID NO: 37) corresponding to residues 50-56 of SEQ ID NO: 22, and SVYDNNR SEQ ID NO: 38) corresponding to residues 50-56 of SEQ ID NOS: 26, 27, 28, and 30,
  a CDR2 comprising the sequence LAS (SEQ ID NO: 39) corresponding to residues 78-80 of SEQ ID NOS: 22, 26, 27, 28, and 30;
  a CDR3 comprising a sequence selected from the group consisting of QGTYDSSGWYWA (SEQ ID NO: 40) corresponding to residues 113-124 of SEQ ID NO: 22, and LGSYSGYIYI (SEQ ID NO: 41) corresponding to residues 113-122 of SEQ ID NOS: 26, 27, 28, and 30.

Related aspects include variants of the monoclonal antibodies or fragments thereof, that contain one or more conservative amino acid substitutions in which the functional activity relating to binding of the antibody or fragment thereof to an epitope of ASPH is retained. Related aspects also include truncated or fusion variants of the monoclonal antibodies comprising one or more insertions or deletions of amino acids in which the in which the functional activity relating to binding of the antibody or fragment thereof to an epitope of ASPH is retained. Related aspects also include variants comprising one or more combinations of conservative amino acid substitutions, insertions, and deletions, particularly where the number of residues that are altered by substitution, insertion, or deletion is small, such as 1, 2, 3, 4, 5, 6, 7, 8, 9, or 10, 11-15, 16-20, and 21-25 residues compared to the parent antibody molecule. Related aspects also include molecules having one or more larger insertions or deletions of amino acid residues or polypeptide domains that do not alter the functional binding activity of the antibody to a desired epitope in a target molecule.

Another aspect relates to a composition comprising any of the antibodies noted above, including compositions comprising at least one antibody that targets ASPH and one or more pharmaceutical excipients.

Another aspect relates to a method of using any of the antibodies noted above, to inhibit the proliferation of isolated tumor cell samples grown in culture.

Another aspect relates to a method of using any of the antibodies noted above, to inhibit the proliferation of tumor cells in tissue samples grown in culture.

Another aspect relates to a method of treating cancer in a mammalian subject, comprising administering to a subject in need thereof an antibody as noted above in an amount sufficient to treat cancer. Related aspects include methods wherein said mammalian subject is a selected from the group consisting of a human, non-human primate, canine, feline, bovine, equine, and a porcine subject. A preferred aspect relates to a method, wherein said mammalian subject is a human subject.

Related aspects also include methods noted above wherein said cancer is selected from the group consisting of cancers of the liver, hepatocellular carcinoma and cholangiocarcinoma, pancreatic cancer, gastric cancer, colon cancer, kidney cancer, non-small cell lung cancer, breast cancer, ovarian cancer, cervical cancer, head-and-neck cancers secondary to human papilloma virus infection, prostate cancer, brain cancer, glioblastoma multiform, neuroblastoma, retinoblastoma, and medulloblastoma, and osteosarcoma.

Another aspect relates to a kit for diagnosis of cancer in a mammalian subject, wherein said kit comprises an antibody, or a fragment thereof, of any of any of the antibodies noted above.

Another aspect relates to a humanized antibody comprising one or more complementarity determining regions (CDRs) derived from a non-human source targeting one or more peptide epitopes located within or adjacent to the catalytic domain of ASPH of any of claims 1-10, and one or more portions of the constant regions of a human antibody, and fragments thereof.

Another aspect relates to a bispecific antibody comprising one or more complementarity determining regions (CDRs) derived from a non-human source targeting one or more peptide epitopes located within or adjacent to the catalytic domain of ASPH of any of claims 1-10, and an antibody targeting other epitopes selected from the group consisting of the T-cell redirector class, comprising an antibody targeting one or more ASPH CDRs and an antibody targeting CD3; the NK-cell redirector class, comprising an antibody targeting one or more ASPH CDRs and an antibody targeting CD16A; the tumor targeting immunomodular class, comprising an antibody targeting one or more ASPH CDRs and an antibody targeting CD40 or 4-1BB; and the dual immunomodular class, comprising an antibody targeting one or more ASPH CDRs and an antibody targeting PD-L1, PD-1, CTLA-4, TGF-β, LAG-3, TIM-3, or OX40.

Therapeutic Uses of Compositions Comprising Compounds of the Invention

Antibodies with direct activity against ASPH antibodies should be useful in the discovery and development of therapeutic drug products intended for use in the treatment of a variety of cancers. These include cancers of the liver, such as hepatocellular carcinoma and cholangiocarcinoma, pancreatic cancer, gastric cancer, colon cancer, kidney cancer, non-small cell lung cancer, breast cancer, ovarian cancer, cervical cancer, head-and-neck cancers secondary to human papilloma virus infection, prostate cancer, brain cancers of various types, including glioblastoma multiform, neuroblastoma, retinoblastoma, and medulloblastoma, and osteosarcoma.

Pharmaceutical Compositions

Related aspects of the invention are directed to compositions, including pharmaceutical compositions, comprising the compounds of the invention, noted above. One aspect of the invention is directed to a pharmaceutical composition comprising at least one pharmaceutically acceptable excipient and a therapeutically effective amount of the compound or salt disclosed above. Still another aspect of the invention relates to a method for pharmaceutical formulation of previously described compounds for use in oral and intravenous applications, and in implantable materials.

Another aspect of the present invention relates to a pharmaceutical composition including a pharmaceutically acceptable carrier and a compound according to the aspects of the present invention. The pharmaceutical composition can contain one or more of the above-identified compounds of the present invention.

Various Modifications and Alternatives, Generally

While specific aspects of the invention have been described in detail, it will be appreciated by those skilled in the art that various modifications and alternatives to those details could be developed in light of the overall teachings of the disclosure. Accordingly, the particular arrangements disclosed are meant to be illustrative only, and not limiting as to the scope of the invention, which is to be given the full breadth of the appended claims, and any equivalent, thereof.

EXAMPLES

The foregoing discussion may be better understood in connection with the following representative examples which are presented for purposes of illustrating the principle methods and compositions of the invention, and not by way of limitation. Various other examples will be apparent to the person skilled in the art after reading the present disclosure without departing from the spirit and scope of the invention. It is intended that all such other examples be included within the scope of the appended claims.

General Materials and Methods

All parts are by weight (e.g., % w/w), and temperatures are in degrees centigrade (° C.), unless otherwise indicated. Table #T1 presents a summary of the nucleotide and amino acid sequences described in this application.

TABLE #T1

Summary of Sequence ID Numbers

| Name | Description | Length | Type | SEQ ID NO: |
|---|---|---|---|---|
| Human ASPH | Polypeptide corresponding to Human ASPH deposited as GenBank Accession No Q12797, starting at the N-terminus with MAQRKNAKSS and ending at the C-terminus with PQQRRSLPAI | 758 | AA | 01 |
| Canine ASPH | Polypeptide corresponding to Canine ASPH deposited as GenBank Accession No XP_022267901, starting at the N-terminus with MAEETKHGGH and ending at the C-terminus with PQQRHSLPAI | 798 | AA | 02 |
| Peptide #H1 | KRRSNEVLR corresponding to residues 391-399 of human ASPH | 9 | AA | 03 |
| Peptide #H2 | DRQQFLGHM corresponding to residues 428-436 of human ASPH | 9 | AA | 04 |
| Peptide #H3 | GYLLIGDNDN corresponding to residues 463-470 of human ASPH | 10 | AA | 05 |
| Peptide #H4 | RSLYNVNG corresponding to residues 562-569 of human ASPH | 8 | AA | 06 |
| Peptide #H5 | PQQRRSLPAI corresponding to residues 749-758 of human ASPH | 10 | AA | 07 |
| Peptide #H6 | FLPEDENLRE corresponding to residues 612-621 of human ASPH | 10 | AA | 08 |
| Peptide #H7 | VWPHTGPTNC corresponding to residues 676-685 of human ASPH | 10 | AA | 09 |
| Peptide #H8 | LWQQGRRNE corresponding to residues 630-638 of human ASPH | 9 | AA | 10 |

TABLE #T1-continued

Summary of Sequence ID Numbers

| Name | Description | Length | Type | SEQ ID NO: |
|---|---|---|---|---|
| Peptide #C1 | KRRSNEVLR corresponding to residues 427-435 of canine ASPH | 9 | AA | 11 |
| Peptide #C2 | DRQQFLGHM corresponding to residues 464-472 of canine ASPH | 9 | AA | 12 |
| Peptide #C3 | GYLLIGDNNN corresponding to residues 499-508 of canine ASPH | 10 | AA | 13 |
| Peptide #C4 | RSLYNVHG corresponding to residues 598-605 of canine ASPH | 8 | AA | 14 |
| Peptide #C5 | PQQRHSLPAI corresponding to residues 785-794 of canine ASPH | 10 | AA | 15 |
| Peptide #C6 | FLPEDENLRE corresponding to residues 648-657 of canine ASPH | 10 | AA | 16 |
| Peptide #C7 | VWPHTGPTNC corresponding to residues 712-721 of canine ASPH | 10 | AA | 17 |
| Peptide #C8 | LWQQGRKINE corresponding to residues 666-674 of canine ASPH | 9 | AA | 18 |
| Peptide #1 (CASSF-PO3H2) | Synthetic peptide comprising 29 amino acids with Cysteine at its amino terminus, plus 28 amino acids corresponding to positions 731-758 at the C-terminal end of human ASPH, with the Threonine at 19 (corresponding to 748 of ASPH) phosphorylated. CASSFRLIFIVDVWHPEL-T(PO3H2)-PQQRRSLPAI | 29 | AA | 19 |
| Peptide #2 | Synthetic peptide comprising 29 amino acids with Cysteine at its amino terminus, plus 28 amino acids corresponding to positions 731-758 at the C-terminal end of human ASPH. CASSFRLIFIVDVWHPELTPQQRRSLPAI | 29 | AA | 20 |
| Clone 1H2 | Translated variable region of Clone ID #1H2 comprising a GQPK sequence at the start of the constant region for a heavy chain sequence. METGLRWLLLVAVLKGVQCQSLEESGGDLVKPGASLTLTCTASGLSFSDNFMCWVRQAPGKGLEWIACIYFDSSGITYYASWAKGRFTISKTSSPTVTLQMTSLTAADTATYFCARDGPGSISWDLWGQGTLVTVSSG*QPK*APSVFPLAP | 150 | AA | 21 |
| Clone 1K6 | Translated variable region of Clone ID #1K6 comprising a GDPV sequence at the start of the constant region for a kappa sequence. MDTRAPTQLLGLLLLWLPGATFAQVLTQTPSPVSAAVGGTVTISCQSSKSVYSKNRLAWYQQKPGQPPKLLIYEASKLASGVPSRFKGSGSGTQFTLTISGVQCDDAATYYCQGTYDSSGWYWAFGGGTEVVVK*GDPV*APTVLIFPPA | 148 | AA | 22 |
| Clone 5H1 | Translated variable region of Clone ID #5H1. METGLRWLLLVAVLKGVQCQSLEESGGDLVKPGASLTLTCKASGFDFSSNAMCWVRQAPGKGPEWIACIDNGDGSTDYATWAKGRFTISKTSSTTVTLQMTSLTAADTATYFCTRNFNLWGPGHPGHRLERTAESPVGVSTG | 142 | AA | 23 |
| Clone 5H3 | Translated variable region of Clone ID #5H3 comprising a GQPK sequence at the start of the constant region for a heavy chain sequence. METGLRWLLLVAVLKGVQCQSLEESGGDLVKPGASLTLTCKASGFDFSSNAMCWVRQAPGKGPEWIACIDNGDGSTDYATWAKGRFTISKTSSTTVTLQMTSLTAADTATYFCTRNFNLWGQGTLVTVSS*GQPK*APSVFPLAP | 143 | AA | 24 |

TABLE #T1-continued

Summary of Sequence ID Numbers

| Name | Description | Length | Type | SEQ ID NO: |
|---|---|---|---|---|
| Clone 5H4 | Translated variable region of Clone ID #5H4 comprising a GQPK sequence at the start of the constant region for a heavy chain sequence.<br>METGLRWLLLVAVLKGVQCQSLEESGGDLVKPGASLTLT<br>CKASGFDFSSNAMCWVRQAPGKGPEWIACIDNGDGSTDY<br>ATWAKGRFTISKTSSTTVTLQMTSLTAADTATYFCTRNF<br>NLWGQGTLVTVSSGQPKAPSVFPLAP | 143 | AA | 25 |
| Clone 5K1 | Translated variable region of Clone ID #5K1 comprising a GDPV sequence at the start of the constant region for a kappa sequence.<br>MDTRAPTQLLGLLLLWLPGATFAQVLTQTASSVSAAVGG<br>TVTISCQSSQSVYDNNRLAWFQQKPGQPPKLLIYETSKL<br>ASGVPLRFKGSGSGTQFTLTISDLECDDAATYYCLGSYS<br>GYIYTFGGGTEVVVKGDPVAPTVLIFPPA | 146 | AA | 26 |
| Clone 5K3 | Translated variable region of Clone ID #5K3 comprising a GDPV sequence at the start of the constant region for a kappa sequence.<br>MDTRAPTQLLGLLLLWLPGATFAQVLTQTASSVSAAVGG<br>TVTISCQSSQSVYDNNRLAWFQQKPGQPPKLLIYETSKL<br>ASGVPLRFKGSGSGTQFTLTISDLECDDAATYYCLGSYS<br>GYIYTFGGGTEVVVKGDPVAPTVLIFPPA | 146 | AA | 27 |
| Clone 5K6 | Translated variable region of Clone ID #5K6 comprising a GDPV sequence at the start of the constant region for a kappa sequence.<br>MDTRAPTQLLGLLLLWLPGATFAQVLTQTASSVSAAVGG<br>TVTISCQSSQSVYDNNRLAWFQQKPGQPPKLLIYETSKL<br>ASGVPLRFKGSGSGTQFTLTISDLECDDAATYYCLGSYS<br>GYIYTFGGGTEVVVKGDPVAPTVLIFPPA | 146 | AA | 28 |
| Clone 9H2 | Translated variable region of Clone ID #9H2 comprising a GQPK sequence at the start of the constant region for a heavy chain sequence.<br>METGLRWLLLVAVMKGVQCQSLEESGGDLVKPGASLTLT<br>CKASGFDFISNAMCWVRQAPGKGPEWIACIDNGDGSTDY<br>ATWAKGRFTISKTSSTTVTLQMTSLTAADTATYFCTRNF<br>NLWGQGTL?TVSSGQPKAPSVFPLAP | 142 | AA | 29 |
| Clone 9K1 | Translated variable region of Clone ID #9K1 comprising a GDPV sequence at the start of the constant region for a kappa sequence.<br>MDTRAPTQLLGLLLLWLPGATFAQVLTQTASSVSAAVGG<br>TVTISCQSSQSVYDNNRLAWFQQKSGQPPKLLIYETSKL<br>ASGVPLRFKGSGSGTQFTLTISDLECDDAATYYCLGSYS<br>GYIYTFGGGTEVVVKGDPVAPTVLIFPPA | 146 | AA | 30 |
| Clone 1H2 CDR1 | CDR1 region of clone 1H2 corresponding to corresponding to residues 50-53 of SEQ ID NO: 21.<br>NFMC | 4 | AA | 31 |
| Clones 5H1, 9H2, 5H3, 5H4 CDR1 | CDR1 region of Clones 5H1, 9H2, 5H3, 5H4, corresponding to residues 50-53 of SEQ ID NOS: 23, 29, 24, and 25.<br>NAMC | 4 | AA | 32 |
| Clone 1H2 CDR2 | The CDR2 regions from the heavy chain clone 1H2 corresponding to residues 68-71 of SEQ ID NO: 21.<br>CIYF | 4 | AA | 33 |
| Clones 5H1, 9H2, 5H3, 5H4 CDR2 | The CDR2 regions from the heavy chain clones 5H1, 9H2, 5H3, 5H4 corresponding to residues 68-71 of SEQ ID NO: 23, 29, 24, and 25.<br>CIDN | 4 | AA | 34 |

TABLE #T1-continued

Summary of Sequence ID Numbers

| Name | Description | Length | Type | SEQ ID NO: |
|---|---|---|---|---|
| Clone 1H2 CDR3 | CDR3 regions from the heavy chain clone 1H2 corresponding to residues 117-126 of SEQ ID NO: 21.<br>DGPGSISWDI | 10 | AA | 35 |
| Clones 5H1, 9H2, 5H3, 5H4 CDR3 | CDR3 regions from the heavy chain clones 5H1, 9H2, 5H3, 5H4 corresponding to residues 116-119 of SEQ ID NOS: 23, 29, 24, and 25.<br>NFNI | 4 | AA | 36 |
| Clone 1K6 CDR1 | The CDR1 regions from the kappa chain clone 1K6, corresponding to residues 50-56 of SEQ ID NO: 22.<br>SVYSKNR | 7 | AA | 37 |
| Clones 5K1, 5K3, 5K6, and 9K1 CDR1 | The CDR1 regions from the kappa chain clones 5K1, 5K3, 5K6, and 9K1 corresponding to residues 50-56 of SEQ ID NOS: 26, 27, 28, and 30.<br>SVYDNNR | 7 | AA | 38 |
| Clones 1K6, 5K1, 5K3, 5K6, and 9K1 CDR2 | The CDR2 regions from the kappa chain clones 1K6, 5K1, 5K3, 5K6, and 9K1 corresponding to residues 78-80 of SEQ ID NOS: 22, 26, 27, 28, and 30.<br>LAS | 3 | AA | 39 |
| Clone 1K6 CDR3 | The CDR3 regions from the kappa chain clone 1K6 corresponding to residues 113-124 of SEQ ID NO: 22.<br>QGTYDSSGWYWA | 12 | AA | 40 |
| Clones 5K1, 5K3, 5K6, and 9K1 CDR3 | The CDR3 regions from the kappa chain clones 5K1, 5K3, 5K6, and 9K1 corresponding to residues 113-122 of SEQ ID NOS: 26, 27, 28, and 30.<br>LGSYSGYIYI | 10 | AA | 41 |
| Peptide PELT | Four aa peptide corresponding to aa 745-748 near the carboxy terminus of human ASPH.<br>PELT | 4 | AA | 42 |
| Peptide ELTP | Four aa peptide corresponding to aa 746-749 near the carboxy terminus of human ASPH.<br>ELTP | 4 | AA | 43 |
| Peptide LTPQ | Four aa peptide corresponding to aa 747-750 near the carboxy terminus of human ASPH.<br>LTPQ | 4 | AA | 44 |
| Peptide TPQQ | Four aa peptide corresponding to aa 748-751 near the carboxy terminus of human ASPH.<br>TPQQ | 4 | AA | 45 |
| Peptide PQRR | Four aa peptide corresponding to aa 749-752 near the carboxy terminus of human ASPH.<br>PQQR | 4 | AA | 46 |
| Peptide QQRR | Four aa peptide corresponding to aa 750-753 near the carboxy terminus of human ASPH.<br>QQRR | 4 | AA | 47 |
| Peptide QRSS | Four aa peptide corresponding to aa 751-754 near the carboxy terminus of human ASPH.<br>QRRS | 4 | AA | 48 |

TABLE #T1-continued

Summary of Sequence ID Numbers

| Name | Description | Length | Type | SEQ ID NO: |
|---|---|---|---|---|
| Peptide RSSL | Four aa peptide corresponding to aa 752-755 near the carboxy terminus of human ASPH. RRSL | 4 | AA | 49 |
| Peptide RSLP | Four aa peptide corresponding to aa 753-756 near the carboxy terminus of human ASPH. RSLP | 4 | AA | 50 |
| Peptide SLPA | Four aa peptide corresponding to aa 754-757 near the carboxy terminus of human ASPH. SLPA | 4 | AA | 51 |
| Peptide LPAI | Four aa peptide corresponding to aa 746-758 near the carboxy terminus of human ASPH. LPAI | 4 | AA | 52 |

Sequence #SQ1: Locations of Peptides #H1-#H8 Along Human ASPH (758 aa)

```
ID      ASPH_HUMAN              Reviewed;         758 AA.
AC      Q12797; A0A0A0MSK8; A6NDF4; A6NHI2; B4DIC9; B4E2K4; B7ZM95; E5RGP5;
AC      F5H667; Q6NXR7; Q8TB28; Q9H291; Q9H2C4; Q9NRI0; Q9NRI1; Q9Y4J0;
DT      01-NOV-1997, integrated into UniProtKB/Swiss-Prot.
DT      17-APR-2007, sequence version 3.
DT      25-APR-2018, entry version 181.

[. . . Text omitted . . .]

SQ      SEQUENCE   758 AA;  85863 MW;  4AE56D1D8DF0AF0C CRC64;
        MAQRKNAKSS GNSSSSGSGS GSTSAGSSSP GARRETKHGG HKNGRKGGLS GTSFFTWFMV  60
        IALLGVWTSV AVVWFDLVDY EEVLGKLGIY DADGDGDFDV DDAKVLLGLK ERSTSEPAVP 120
        PEEAEPHTEP EEQVPVEAEP QNIEDEAKEQ IQSLLHEMVH AEHVEGEDLQ QEDGPTGEPQ 180
        QEDDEFLMAT DVDDRFETLE PEVSHEETEH SYHVEETVSQ DCNQDMEEMM SEQENPDSSE 240
        PVVEDERLHH DTDDVTYQVY EEQAVYEPLE NEGIEITEVT APPEDNPVED SQVIVEEVSI 300
        FPVEEQQEVP PETNRKTDDP EQKAKVKKKK PKLLNKFDKT IKAELDAAEK LRKRGKIEEA 360
                                     Peptide #H1<391 . . . 399>
        VNAFKELVRK YPQSPRARYG KAQCEDDLAE KRRSNEVLRG AIETYQEVAS LPDVPADLLK 420
Peptide #H2<428 . . . 436>                  Peptide #H3<463 . . . 470>
        LSLKRRSDRQ QFLGHMRGSL LTLQRLVQLF PNDTSLKNDL GVGYLLIGDN DNAKKVYEEV 480
        LSVTPNDGFA KVHYGFILKA QNKIAESIPY LKEGIESGDP GTDDGRFYFH LGDAMQRVGN 540
                      Peptide #H4<562569>
        KEAYKWYELG HKRGHFASVW QRSLYNVNGL KAQPWWTPKE TGYTELVKSL ERNWKLIRDE 600
          Peptide #H6<612 . . . 621> #H8<630 . . . 638>
        GLAVMDKAKG LFLPEDENLR EKGDWSQFTL WQQGRRNENA CKGAPKTCTL LEKFPETTGC 660
              Peptide #H7<676 . . . 685>
        RRGQIKYSIM HPGTHVWPHT GPTNCRLRMH LGLVIPKEGC KIRCANETKT WEEGKVLIFD 720
                        Peptide #H5<749 . . . 758>
        DSFEHEVWQD ASSFRLIFIV DVWHPELTPQ QRRSLPAI                        758
//
```

Sequence #SQ2: Locations of Peptides #C1-#C8 Along Canine ASPH, isoform X1 (794 aa)

```
LOCUS       XP_022267901 794 aa linear MAM 05 Sep. 2017
DEFINITION  aspartyl/asparaginyl beta-hydroxylase isoform X1 [Canis lupus
            familiaris].
ACCESSION   XP_022267901
VERSION     XP_022267901.1

[. . . Text omitted . . .]
ORIGIN
        1 MAEETKHGGH KNGRKGGLSG SSFFTWFMVI ALLGVWTSVA VVWFDLVDYE EVLAKAKDFR
       61 YNLSEVLQGK LGVYDADGDG DFDVDDAKVL LGLTKDGSNE NIDSLEEVLN ILAEESSDWF
      121 YGFLSFLYDI MTPFEMLEEE EESETADGV DGLKERSASK PTVPPEEAEP YPWLEEQVIE
      181 DSGPQNTEDE VQEVQIESLL HEAVYTEHGD DVQQEEDGQV REPQPEDDFL VGSDTDDRYE
      241 PLETGTFHEE TEDSYHIEET ASQAYNQDME EMMYEQDNPD SMEPIVGDDA RTYHEADDLT
      301 YQDYDEPVYE PPENEGLESS DNAGEDSNII LEEVYMPPAE EQQEVPPETN RKTDDPEIKE
      361 KVKKKKPKLL NKFDKTIKAE LDAAEKLRKR GKIEEALSAF QELVRKYPQS PRARYGKAQC
                Peptide #C1<427 . . . 435>                    Peptide #C2<464 . . . 472>
```

```
            421 EDDLAEKRRS NEVLRGAIET YQEVASLPNV PTDLLKLTLK RRSDRQQFLG HMRGSLITLQ
                           Peptide #C3<499 . . . 508>
            481 KLVQLFPDDM SLKNDLGVGY LLIGDNNNAQ KVYEEVLNVT PNDGFAKVHY GFILKAQNKI
                                                                        Peptide #C4<598
            541 AESIPYLKEG IESGDPGTDD GRFYFHLGDA MQRVGNKEAY KWYELGHKRG HFASVWQRSL
              .605>                                            Peptide #C6<648 . . . 657>
            601 YNVHGLKAQP WWTPKETGYT ELVKSLERNW KLIRDEGLAV MDKAKGLFLP EDENLREKGD
     Peptide #C8<666 . . . 674>                                     Peptide #C7<712 . . .
            661 WSQFTLWQQG RKNENACKGA PKTCSLLDKF PETTGCRRGQ IKYSIMHPGT HVWPHTGPTN
              .721>
            721 CRLRMHLGLV IPKEGCKIRC ANETKTWEEG KVLIFDDSFE HEVWQDATSF RLIFIVDVWH
     Peptide #C5<785 . . . 794>
            781 PELTPQQRHS LPAI
//
```

```
              Sequence #SQ3: Aligned Human ASPH (758 aa) and Canine ASPH,
                              Isoform X1 (794 aa) Sequences
```

```
Query       IDXP_022267901.1
Description aspartyl/asparaginyl beta-hydroxylase isoform X1 [Canis lupus
            familiaris]
Molecule type amino acid
Query Length 794

Subject     IDQ12797.3
Description RecName: Full= Aspartyl/asparaginyl beta-hydroxylase; AltName:
            Full = Aspartate beta-hydroxylase; Short = ASP beta-hydroxylase;
            AltName: Full = Peptide-aspartate beta-dioxygenase
Molecule type amino acid
Subject Length 758

Query           1  MAE-----------------------------ETKHGGHKNGRKGGLSGSSFFTWFMV    29
                   MA+                          ETKHGGHKNGRKGGLSG+SFFTWFMV
Sbjct           1  MAQRKNAKSSGNSSSSGSGSGSTSAGSSSPGARRETKHGGHKNGRKGGLSGTSFFTWFMV   60

Query          30  IALLGVWTSVAVVWFDLVDYEEVLAKAKDFRYNLSEVLQGKLGVYDADGDGDFDVDDAKV   89
                   IALLGVWTSVAVVWFDLVDYEEVL               GKLG+YDADGDGDFDVDDAKV
Sbjct          61  IALLGVWTSVAVVWFDLVDYEEVL---------------GKLGIYDADGDGDFDVDDAKV  105

Query          90  LLGLTKDGSNENIDSLEEVLNILAEESSDWFYGFLSFLYDIMTPFEMLEEEEEESETADG  149
                   LLGL
Sbjct         106  LLGL--------------------------------------------------------  109

Query         150  VDGLKERSASKPTVPPEEAEPYPWLEEQVIEDSGPQNTEDEVQEVQIESLLHEAVYTEH-  208
                       KERS S+P VPPEEAEP+   EEQV  ++ PQN EDE +E QI+SLLHE V+ EH
Sbjct         110  ----KERSTSEPAVPPEEAEPHTEPEEQVPVEAEPQNIEDEAKE-QIQSLLHEMVHAEHV  164

Query         209  -GDDVQQEEDGQVREPQPEDD-FLVGSDTDDRYEPLETGTFHEEETEDSYHIEETASQAYN  266
                    G+D+QQE DG    EPQ EDD FL+ +D DDR+E LE    HEETE SYH+EET SQ  N
Sbjct         165  EGEDLQQE-DGPTGEPQQEDDEFLMATDVDDRFETLEPEVSHEETEHSYHVEETVSQDCN  223

Query         267  QDMEEMMYEQDNPDSMEPIVGDDARTYHEADDLTYQDYDEP-VYEPPENEGLESS-----  320
                   QDMEEMM EQ+NPDS EP+V +D R +H+ DD+TYQ Y+E  VYEP ENEG E +
Sbjct              QDMEEMMSEQENPDSSEPVV-EDERLHHDTDDVTYQVYEEQAVYEPLENEGIEITEVTAP Query         321  --DNAGEDSNIILEEVYMPPAEEQQEVPPETNRKTDDPEIKEKVKKKKPKLLNKFDKTIK  378
                     DN   EDS +I+EEV + P EEQQEVPPETNRKTDDPE K KVKKKKPKLLNKFDKTIK
Sbjct         283  PEDNPVEDSQVIVEEVSIFPVEEQQEVPPETNRKTDDPEQKAKVKKKKPKLLNKFDKTIK  342

Peptide #C1<427 . . . 435>
Query         379  AELDAAEKLRKRGKIEEALSAFQELVRKYPQSPRARYGKAQCEDDLAEKRRSNEVLRGAI  438
                   AELDAAEKLRKRGKIEEA++AF+ELVRKYPQSPRARYGKAQCEDDLAEKRRSNEVLRGAI
Sbjct         343  AELDAAEKLRKRGKIEEAVNAFKELVRKYPQSPRARYGKAQCEDDLAEKRRSNEVLRGAI  402
                                                             Peptide #H1<391 . . . 399>

Peptide #C2<464 . . . 472>
Query         439  ETYQEVASLPNVPTDLLKLTLKRRSDRQQFLGHMRGSLITLQKLVQLFPDDMSLKNDLGV  498
                   ETYQEVASLP+VP DLLKL+LKRRSDRQQFLGHMRGSL TLQ+LVQLFP+D SLKNDLGV
Sbjct         403  ETYQEVASLPDVPADLLKLSLKRRSDRQQFLGHMRGSLLTLQRLVQLFPNDTSLKNDLGV  462
                           Peptide #H2<428 . . . 436>
```

```
Peptide #C3<499 . . . 508>
Query      499 GYLLIGDNNNAQKVYEEVLNVTPNDGFAKVHYGFILKAQNKIAESIPYLKEGIESGDPGT 558
               GYLLIGDN+NA+KVYEEVL+VTPNDGFAKVHYGFILKAQNKIAESIPYLKEGIESGDPGT
                       *
Sbjct      463 GYLLIGDNDNAKKVYEEVLSVTPNDGFAKVHYGFILKAQNKIAESIPYLKEGIESGDPGT 552
    Peptide #H3<463 . . . 470>

Peptide #C4<598605>
Query      559 DDGRFYFHLGDAMQRVGNKEAYKWYELGHKRGHFASVWQRSLYNVHGLKAQPWWTPKETG 618
               DDGRFYFHLGDAMQRVGNKEAYKWYELGHKRGHFASVWQRSLYNV+GLKAQPWWTPKETG
Sbjct                                                     *
           523 DDGRFYFHLGDAMQRVGNKEAYKWYELGHKRGHFASVWQRSLYNVNGLKAQPWWTPKETG 582
                                    Peptide #H4<562569>

Peptide #C6<648 . . .    657> #C8<666 . . . 674>
Query      619 YTELVKSLERNWKLIRDEGLAVMDKAKGLFLPEDENLREKGDWSQFTLWQQGRKNENACK 678
               YTELVKSLERNWKLIRDEGALVMDKAKGLFLPEDENLREKGDWSQFTLWQQGR+NENACK
Sbjct                                                              *
           583 YTELVKSLERNWKLIRDEGLAVMDKAKGLFLPEDENLREKGDWSQFTLWQQGRRNENACK 642
                             Peptide #H6<612 . . .   621> #H8<630 . . . 638>

Peptide #C7<712 . . . 721>
Query      679 GAPKTCSLLDKFPETTGCRRGQIKYSIMHPGTHVWPHTGPTNCRLRMHLGLVIPEKGCKI 738
               GAPKTC+LL+KFPETTGCRRGQIKYSIMHPGTHVWPHTGPTNCRLRMHLVLVIPKEGCKI
Sbjct      643 GAPKTCTLLEKFPETTGCRRGQIKYSIMHPGHTVWPHTGPTNCRLRMHLGLVIPKEGCKI 702
                                   Peptide #H7<676 . . . 685>

Peptide #C5<785 . . . 794>
Query      739 RCANETKTWEEGKVLIFDDSFEHEVWQDATSFRLIFIVDVWHPELTPQQRHSLPAI 794
               RCANETKTWEEGKVLIFDDSFEHEVWQDA+SFRLIFIVDVWHPELTPQQR_SLPAI
Sbjct                                                       *
           703 RCANETKTWEEGKVLIFDDSFEHEVWQDASSFRLIFIVDVWHPELTPQQRRSLPAI 758
                                           Peptide #H5<749 . . . 758>
```

Example 1—Design and Synthesis of Synthetic Peptides Corresponding to Epitopes of ASPH

Synthesis of Exemplary Compounds

Synthetic peptides derived from human and/or canine ASPH were designed that correspond to eight domain regions (#1-#8, as #H1-#H8 and #C1-#C8), as penultimate domain epitopes of the full length polypeptide, as illustrated in FIG. 2A, and shown in FIG. 2B and below in Table #T2. These peptides were rationally selected based upon the spatial distance from the substrate, as found in crystal structure 5JZZ deposited at the RCSB Protein Databank. Peptide epitope domain regions #1-#3 are from the non-catalytic domain, while peptide epitope domain regions #4 & #5 are from the C-terminal catalytic domain, but outside of residues 650-700. Peptide epitope domain regions #6, #7, and #8 are within or near the C-terminal catalytic domain of ASPH.

TABLE #T2

Peptide Sequences Corresponding to Penultimate Domain Epitopes of Human and Canine ASPH

| Epitope Domain | Organism | Sequence | Short Name | Positions in Human ASPH | Positions in Canine ASPH | SEQ ID NOS |
|---|---|---|---|---|---|---|
| #1 | HUMAN/CANINE | KRRSNEVLR | #H1/#C1 | 391-399 | 427-435 | 03/11 |
| #2 | HUMAN/CANINE | DRQQFLGHM | #H2/C2 | 428-536 | 464-472 | 04/12 |
| #3 | HUMAN | GYLLIGDNDN | #H3 | 463-470 |  | 05 |
|  | CANINE | GYLLIGDNNN | #C3 |  | 499-508 | 13 |
| #4 | HUMAN | RSLYNVNG | #H4 | 562-569 |  | 06 |
|  | CANINE | RSLYNVHG | #C4 |  | 598-605 | 14 |
| #5 | HUMAN | PQQRRSLPAI | #H5 | 749-758 |  | 07 |
|  | CANINE | PQQRHSLPAI | #C5 |  | 785-794 | 15 |
| #6 | HUMAN/CANINE | FLPEDENLRE | #H6/C6 | 612-621 | 648-657 | 08/16 |
| #7 | HUMAN/CANINE | VWPHTGPTNC | #H7/C7 | 676-685 | 712-721 | 10 |
| #8 | HUMAN | LWQQGRRNE | #H8 | 630-638 |  | 10 |

TABLE #T2-continued

Peptide Sequences Corresponding to Penultimate Domain Epitopes of Human and Canine ASPH

| Epitope Domain | Organism | Sequence | Short Name | Positions in Human ASPH | Positions in Canine ASPH | SEQ ID NOS |
|---|---|---|---|---|---|---|
| | CANINE | LWQQGRKNE | #C8 | | 666-674 | 18 |

Example 2—Immunization of Peptide Candidates into Rabbits and Test Bleed

ImmunoPrecise Antibodies Ltd. (Victoria, British Columbia, Canada) carried out immunization of peptide candidates into rabbits, the testing of antibodies from rabbit B cells, cloning of variable regions into expression vectors, and DNA sequencing of selected rabbit MAbs (Examples 2-8) using standard procedures, under contract with principal investigators at Midwestern University (Glendale, Ariz.).

antibody titer by ELISA. Each rabbit was given a final boost, if required, and whole blood was used to obtain B cells to generate Monoclonal Antibodies (MAbs) by the methods noted below.

Example 3—In Vitro Culture of Rabbit B Cells

Whole rabbit blood was collected after the final boost, and B cells were isolated, purified, and cultured by ImmunoPrecise Antibodies Ltd.

TABLE #T3

Synthetic Peptide Sequences Used as Immunogens Directed against ASPH

| Short Name | Description/Sequence | Positions in Human ASPH | Epitope Domain | SEQ ID NOS |
|---|---|---|---|---|
| Peptide #1 (CASSF-PO3H2) | Synthetic peptide comprising 29 amino acids with Cystein at its amino terminus, plus 28 amino acids corresponding to positions 731-758 at the C-terminal end of human ASPH, with the Threonine at 19 (corresponding to 748 of ASPH) phosphorylated.<br>C-ASSFRLIFIV DVWHPEL-T(PO3H2)-PQ QRRSLPAI | 731-758 | #5 | 19 |
| Peptide #2 | Synthetic peptide comprising 29 amino acids with Cysteineat its amino terminus, plus 28 amino acids corresponding to positions 731-758 at the C-terminal end of human ASPH.<br>C-ASSFRLIFIV DVWHPELTPQ QRRSLPAI | 731-758 | #5 | 20 |

Synthetic peptides #1 and #2 (1 mg each) were prepared at a purity of >95%. The N-terminal Cysteine residue on each peptide is used to facilitate conjugation of each peptide to other molecules. BSA and KLH (2 mg each) were synthesized or obtained from commercial sources.

```
Peptide #1
                                    (SEQ ID NO: 19)
CASSFRLIFIVDVWHPEL-T(PO3H2)-PQQRRSLPAI Peptide #2
                                    (SEQ ID NO: 20)
CASSFRLIFIVDVWHPELTPQQRRSLPAI
```

Briefly, 3-6 mg of immunizing/screening antigen were prepared and stored in a neutral pH, sterile, buffered solution, at a minimum concentration of 0.5 mg/L. Antigen (hapten) was conjugated to an appropriate carrier and emulsified in Freund's Complete adjuvant, and used to immunize two New Zealand White (NZW) rabbits by subcutaneous injections. Booster injections of antigen in Freund's Incomplete adjuvant were carried at 3 week intervals. Blood samples (test bleeds) were collected 7-10 days after the second boost and immune sera were tested for specific

Example 4—Screening and Analysis of Antibodies from Rabbit B Cells

Screening was performed on the immunizing antigen by an indirect ELISA performed by ImmunoPrecise Antibodies Ltd.

ELISA plates were obtained from Costar Corning (Catalog #0720039). Blocking solutions included BSA (Bovine serum albumin) and Skim milk powder (MP). Phosphate buffered saline (PBS) at pH 7.4, PBS with 0.05% Tween-20 at pH 7.4, and Carbonate coating buffer (CCB) at pH 9.6 were used in the ELISA tests. Primary antibodies being tested included the immune sera, B cell supernatants, and transfected supernatants (recombinant rabbit MAbs). Secondary antibodies included Goat Anti-Rabbit IgG-Fc-HRP, Subisotype IgG1, obtained from Jackson ImmunoResearch (Catalog #111-035-046), and AffiniPure goat anti-rabbit IgG (H+L), Subisotype IgG1, obtained from Jackson ImmunoResearch (Catalog #111-035-144). Substrate reagents included TMB (3,3',5,5'-tetramethyl-benzidine buffer), TMB One Component HRP Microwell Substrate, and BioFx cat #TMBW-1000-01.

Briefly, B cell culture supernatants from 96-well plates were transferred to ELISA plates coated with antigen. An indirect ELISA was performed by probing each well with a secondary antibody that binds to rabbit IgG antibodies. Wells with cells that tested positive were retested with the immunizing antigen to confirm specificity and binding.

Samples corresponding to the top responding wells were preserved in lysis buffer.

Cell culture supernatants from positive wells (in a volume of <50 µL) were also preserved.

Example 5—Cloning Antibody Heavy and Light Chain Variable Regions in Mammalian Expression Vectors Cells from selected wells of B cells were amplified and samples of mRNA prepared from those cells by Immuno-Precise Antibodies Ltd. Complementary DNAs corresponding to rabbit IgG heavy and kappa light chain variable regions were prepared and cloned separately into mammalian expression vectors comprising rabbit heavy and light chain constant regions, respectively.

Example 6—Expression of Antibody Heavy and Light Chain Variable Regions into HEK293 Cells Two plasmids, one comprising a heavy chain variable and a constant region and one comprising a light chain variable and constant region, were co-transfected into HEK293 cells, and allowed to express both chains of the rabbit antibodies.

Example 7—Analysis of Cell Culture Supernatants

The cell culture supernatants were assayed for activity by indirect ELISA against the immunizing peptide (Peptide #1, SEQ ID NO: 13). Ten clones (#1-#10) having positive activity against immunizing peptide were identified. One clone produced an antibody that reacted with the phosphorylated Peptide #1, and four clones produced antibodies that reacted against both the phosphorylated Peptide #1 (SEQ ID NO: 19) and the non-phosphorylated Peptide #2 (SEQ ID NO: 20).

Example 8—DNA Sequencing of Heavy and Light Chain Regions from Selected Positive Rabbit MAbs Ten clones were selected, five comprising heavy chains (1H2, 5H1, 5H3, 5H4 and 9H2), and five comprising kappa chains (1K6, 5K1, 5K3, 5K6 and 9K1). Purified plasmid DNA samples were prepared and sent to Macrogen USA for sequencing and analyzed by SnapGene Version 4.0.4.

The rabbit IgG heavy chain sequence is about 1200 bp in length, and can be sequenced from its 5' end to obtain a reliable full-length variable sequence. The rabbit kappa light chain is about 700 bp in length, and full-length variable sequence can be reliably obtained from sequencing in the 5' direction.

Analysis of Translation of Consensus Amino Acid Sequences

The nucleotide sequences of the variable regions of five heavy chains and five kappa chains were analyzed. Table #T4 discloses the translated variable regions encoded by the nucleotide sequences of the top 10 clones. Sequences highlighted in bold with a single underline (as GQPK) show the start of the constant region for heavy chains, and sequences highlighted in italic and double underline (as *GDPV*) show the start of the constant region of kappa chains.

TABLE #T4

Translated variable region sequences of the top clones

| # | Clone ID | Description or Sequence | Length | Type | SEQ ID NO |
|---|---|---|---|---|---|
| 1 | 1H2 | METGLRWLLLVAVLKGVQCQSLEESGGDLVKPGASLTLTCTAS GLSFSDNFMCWVRQAPGKGLEWIACIYFDSSGITYYASWAKGR FTISKTSSPTVTLQMTSLTAADTATYFCARDGPGSISWDLWGQ GTLVTVSSGQPKAPSVFPLAP | 150 | AA | 21 |
| 2 | 1K6 | MDTRAPTQLLGLLLLWLPGATFAQVLTQTPSPVSAAVGGTVTI SCQSSKSVYSKNRLAWYQQKPGQPPKLLIYEASKLASGVPSRF KGSGSGTQFTLTISGVQCDDAATYYCQGTYDSSGWYWAFGGGT EVVVK*GDPV*APTVLIFPPA | 148 | AA | 22 |
| 3 | 5H1 | METGLRWLLLVAVLKGVQCQSLEESGGDLVKPGASLTLTCKAS GFDFSSNAMCWVRQAPGKGPEWIACIDNGDGSTDYATWAKGRF TISKTSSTTVTLQMTSLTAADTATYFCTRNFNLWGPGHPGHRL ERTAESPVGVSTG | 142 | AA | 23 |
| 4 | 5H3 | METGLRWLLLVAVLKGVQCQSLEESGGDLVKPGASLTLTCKAS GFDFSSNAMCWVRQAPGKGPEWIACIDNGDGSTDYATWAKGRF TISKTSSTTVTLQMTSLTAADTATYFCTRNFNLWGQGTLVTVS SGQPKAPSVFPLAP | 143 | AA | 24 |
| 5 | 5H4 | METGLRWLLLVAVLKGVQCQSLEESGGDLVKPGASLTLTCKAS GFDFSSNAMCWVRQAPGKGPEWIACIDNGDGSTDYATWAKGRF TISKTSSTTVTLQMTSLTAADTATYFCTRNFNLWGQGTLVTVS SGQPKAPSVFPLAP | 143 | AA | 25 |
| 6 | 5K1 | MDTRAPTQLLGLLLLWLPGATFAQVLTQTASSVSAAVGGTVTI SCQSSQSVYDNNRLAWFQQKPGQPPKLLIYETSKLASGVPLRF KGSGSGTQFTLTISDLECDDAATYYCLGSYSGYIYTFGGGTEV VVK*GDPV*APTVLIFPPA | 146 | AA | 26 |
| 7 | 5K3 | MDTRAPTQLLGLLLLWLPGATFAQVLTQTASSVSAAVGGTVTI SCQSSQSVYDNNRLAWFQQKPGQPPKLLIYETSKLASGVPLRF | 146 | AA | 27 |

TABLE #T4-continued

Translated variable region sequences of the top clones

| # | Clone ID | Description or Sequence | Length | Type | SEQ ID NO |
|---|---|---|---|---|---|
| | | KGSGSGTQFTLTISDLECDDAATYYCLGSYSGYIYTFGGGTEV VVKGDPVAPTVLIFPPA | | | |
| 8 | 5K6 | MDTRAPTQLLGLLLLWLPGATFAQVLTQTASSVSAAVGGTVTI SCQSSQSVYDNNRLAWFQQKPGQPPKLLIYETSKLASGVPLRF KGSGSGTQFTLTISDLECDDAATYYCLGSYSGYIYTFGGGTEV VVKGDPVAPTVLIFPPA | 146 | AA | 28 |
| 9 | 9H2 | METGLRWLLLLVAVLKGVQCQSLEESGGDLVKPGASLTLTCKAS GFDFISNAMCWVRQAPGKGPEWIACIDNGDGSTDYATWAKGRF TISKTSSTTVTLQMTSLTAADTATYFCTRNFNLWGQGTL?TVS SGQPKAPSVFPLAP | 142 | AA | 29 |
| 10 | 9K1 | MDTRAPTQLLGLLLLWLPGATFAQVLTQTASSVSAAVGGTVTI SCQSSQSVYDNNRLAWFQQKSGQPPKLLIYETSKLASGVPLRF KGSGSGTQFTLTISDLECDDAATYYCLGSYSGYIYTFGGGTEV VVKGDPVAPTVLIFPPA | 146 | AA | 30 |

These results demonstrate that recombinant monoclonal antibodies derived from rabbits, were generated successfully against Peptide #1 (SEQ ID NO: 13). Recombinant Clones 5H1, 5H3, 5H4, and 9H2 have the same heavy chain sequences, and recombinant clones 5K1, 5K3 and 9K1 have the same kappa chain sequence.

residues 50-53 of SEQ ID NO: 21, and NAMC (SEQ ID NO: 32), corresponding to residues 50-53 of SEQ ID NOS: 23, 29, 24, and 25. The CDR2 regions from the heavy chain clones include CIYF (SEQ ID NO: 33) corresponding to residues 68-71 of SEQ ID NO: 21, and CIDN (SEQ ID NO: 34) corresponding to residues 68-71 of SEQ ID NO: 23, 29, Sequence #SQ4: Multiple Sequence Alignment of Heavy Chains for Clones 1H2, 5H1, 9H2, 5H3, and 5H4
A multiple sequence alignment of five clones comprising heavy chains illustrates slight differences in the encoded polypeptide sequences in regions within and just flanking CDR1, CDR2, CDR3, with notable divergence for sequences after CDR3 for clone 5H1.

CLUSTAL O (1.2.4) multiple sequence alignment heavy chains:

```
1H2  METGLRWLLLVAVLKGVQCQSLEESGGDLVKPGASLTLTCTASGLSFSD|NFMC|WVRQAPG 60   SEQ ID NO: 21
5H1  METGLPWLLLVAVLKGVQCQSLEESGGDLVKPGASLTLTCKASGFDFSS|NAMC|WVRQAPG 60   SEQ ID NO: 23
9H2  METGLRWLLLVAVLKGVQCQSLEESGGDLVKPGASLTLTCKASGEDFIS|NAMC|WVRQAPG 60   SEQ ID NO: 29
5H3  METGLRWLLLVAVLKGVQCQSLEESGGDLVKPGASLTLTCKASGEDFSS|NAMC|WVRQAPG 60   SEQ ID NO: 24
5H4  METGLRWLLLVAVLKGVQCQSLEESGGDLVKPGASLTLTCKASGEDFSS|NAMC|WVRQAPG 60   SEQ ID NO: 25
                                                      CDR1

1H2  KGLEWIA|CIYF|DSSGITYYASWAKGRFTISKTSSPTVTLQMTSLTAADTATYFCAR|DGPG| 120
5H1  KGPEWIA|CIDN|-GDGSTDYATWARGRFTISKTSSTTVTLQMTSLTAADTATYFCTR|N---| 116
9H2  KGPEWIA|CIDN|-GDGSTDYATWAKGRFTISKTSSTTVTLQMTSLTAADTATYFCTR|N---| 116
5H3  KGPEWIA|CIDN|-GDGSTDYATWAKGRFTISKTSSTTVTLQMTSLTAADTATYFCTR|N---| 116
5H4  KGPEWIA|CIDN|-GDGSTDYATWARGRFTISKTSSTTVTLQMTSLTAADTATYFCTR|N---| 116
             CDR2                                              CDR3

1H2  |SISWDL|WGQGTLVTVSSGQPKAPSVFPLAP 150
5H1  |---FNL|WGPGHPGHRLERTAESPVGVSTG- 142
9H2  |---FNL|WGQGTLXTVSSGQPKAPSVFPLAP 143
5H3  |---FNL|WGQGTLVTVSSGQPKAPSVFPLA- 142
5H4  |---FNL|WGQGTLVTVSSGQPKAPSVFPLAP 143
     CDR3 cont.
```

The CDR1 regions from the heavy chain clones include the sequences NFMC (SEQ ID NO: 31), corresponding to 24, and 25. The CDR3 regions from the heavy chain clones include DGPGSISWDI (SEQ ID NO: 35) corresponding to residues 117-126 of SEQ ID NO: 21, and NFNI (SEQ ID NO: 36) corresponding to residues 116-119 of SEQ ID NOS: 23, 29, 24, and 25.

binding was blocked using 3% Normal Goat Serum in PBST. Tests for positive reactions were carried out by using Novocastra Bond Refine Polymer Detection reagent, and

---

Sequence #SQ5: Multiple Sequence Alignment of Kappa Light Chains
for Clones 1K6, 5K1, 5K3, 5K6, and 9K1
A multiple sequence alignment of five clones comprising kappa light chains illustrates
slight differences in the encoded polypeptide sequences in regions within and just flanking
CDR1, CDR2, CDR3, with notable divergence for sequences within CDR3 for clone 1K6.

---

CLUSTAL O (1.2.4) multiple sequence alignment kappa chains:

```
1K6  MDTRAPTQLLGLLLLWLPGATFAQVLTQTPSPVSAAVGGTVTISCQSSK|SVYSKNR|LAWY  60  SEQ ID NO: 22

5K1  MDTRAPTQLLGLLLLWLPGATFAQVLTQTASSVSAAVGGTVTISCQSSQ|SVYDNNR|LAWF  60  SEQ ID NO: 26

5K3  MDTRAPTQLLGLLLLWLPGATFAQVLTQTASSVSAAVGGTVTISCQSSQ|SVYDNNR|LAWF  60  SEQ ID NO: 27

5K6  MDTRAPTQLLGLLLLWLPGATFAQVLTQTASSVSAAVGGTVTISCQSSQ|SVYDNNR|LAWF  60  SEQ ID NO: 28

9K1  MDTRAPTQLLGLLLLWLPGATFAQVLTQTASSVSAAVGGTVTISCQSSQ|SVYDNNR|LAWF  60  SEQ ID NO: 30
                                                       CDR1

1K6  QQKPGQPPKLLIYEASK|LAS|GVPSRFKGSGSGTQFTLTISGVQCDDAATYYC|QGTYDSSG| 120

5K1  QQKPGQPPKLLIYETSK|LAS|GVPLRFKGSGSGTQFTLTISDLECDDAATYYC|LGSY--SG| 118

5K3  QQKPGQPPKLLIYETSK|LAS|GVPLRFKGSGSGTQFTLTISDLECDDAATYYC|LGSY--SG| 118

5K6  QQKPGQPPKLLIYETSK|LAS|GVPLRFKGSGSGTQFTLTISDLECDDAATYYC|LGSY--SG| 118

9K1  QQKSGQPPKLLIYETSK|LAS|GVPLRFKGSGSGTQFTLTISDLECDDAATYYC|LGSY--SG| 118
                      CDR2                                  CDR3

1K6  |WYWA|FGGGTEVVVKGDPVAPTVLIFPPA 148

5K1  |YIYT|FGGGTEVVVKGDPVAPTVLIFPPA 146

5K3  |YIYT|FGGGTEVVVKGDPVAPTVLIFPPA 146

5K6  |YIYT|FGGGTEVVVKGDPVAPTVLIFPPA 146

9K1  |YIYT|FGGGTEVVVKGDPVAPTVLIFPPA 146
     CDR3 cont.
```

---

The CDR1 regions from the kappa chain clones 1K6, 5K1, 5K3, 5K6, and 9K1 include SVYSKNR (SEQ ID NO: 37) corresponding to residues 50-56 of SEQ ID NO: 22, and SVYDNNR (SEQ ID NO: 38) corresponding to residues 50-56 of SEQ ID NOS: 26, 27, 28, and 30. The CDR2 regions from the kappa chain clones were all LAS (SEQ ID NO: 39) corresponding to residues 78-80 of SEQ ID NOS: 22, 26, 27, 28, and 30. The CDR3 regions from the kappa chain clones included QGTYDSSGWYWA (SEQ ID NO: 40) corresponding to residues 113-124 of SEQ ID NO: 22, and LGSYSGYIYI (SEQ ID NO: 41) corresponding to residues 113-122 of SEQ ID NOS: 26, 27, 28, and 30.

Example 9—Analysis of MAbs by Immunohistochemistry (IHC)—Phase I—Antibody Triage Antibody triage (Phase I) was performed by Reveal Biosciences (San Diego, Calif.) on a Leica Bond automated immunostainer, testing each antibody at 8 µg/mL, in parallel with a negative control performed in absence of primary antibody. FFPE human hepatocellular carcinoma was used for antibody testing.

Heat induced antigen retrieval was performed using Leica Bond Epitope Retrieval Buffer 1 (Citrate Buffer, pH6.0) and Leica Bond Epitope Retrieval Buffer 2 (EDTA solution, pH9.0) for 20 minutes (ER2(20)). Non-specific antibody binding was blocked using 3% Normal Goat Serum in PBST. Tests for positive reactions were carried out by using Novocastra Bond Refine Polymer Detection reagent, and visualized with 3'3-diaminobenzidine (DAB; brown). A Hematoxylin nuclear counterstain (blue) was also applied.

When Phase I optimization slides were evaluated, only two samples, 5H4/5K3 and 9H2/9K1, showed positive staining in Epitope Retrieval Buffer, ER2(20), as noted below.

TABLE #T5

Results of Antibody Triage

| Groups | Antibody | Dilution | Host Species | Antigen Retrieval |
|---|---|---|---|---|
| 1 | 1H2/1K6 | 8 µg/mL | Rabbit | NONE |
|   | 1H2/1K5 |   |   | NONE |
|   | 1H4/1K6 |   |   | NONE |
|   | 1H4/1K4 |   |   | NONE |
| 2 | 2H4/2K5 |   |   | NONE |
|   | 5H1/5K1 |   |   | NONE |
|   | 5H4/5K3 |   |   | ER2(20) |
|   | 9H2/9K1 |   |   | ER2(20) |

Two antibodies, 5H4/5K3 and 9H2/9K1, that showed positive staining in ER2(20), were selected for further testing in Phase II.

Example 10A—Analysis of MAbs by Immunohistochemistry (IHC)—Phase II—IHC Optimization Immunohistochemistry (IHC) Optimization was performed by Reveal Biosciences (San Diego, Calif.) on a Leica Bond automated immunostainer, by testing each antibody at 2 µg/mL, 4 µg/mL, 8 µg/mL, and 10 µg/mL.

Heat induced antigen retrieval was performed using Leica Bond Epitope Retrieval Buffer 2 (EDTA solution, pH9.0) for 20 minutes (ER2(20)). Non-specific antibody binding was blocked using 3% Normal Goat Serum in PBST. Tests for positive reactions were carried out by using Novocastra Bond Refine Polymer Detection and visualized with 3'3-diaminobenzidine (DAB; brown). A Hematoxylin nuclear counterstain (blue) was applied.

Figure 7:
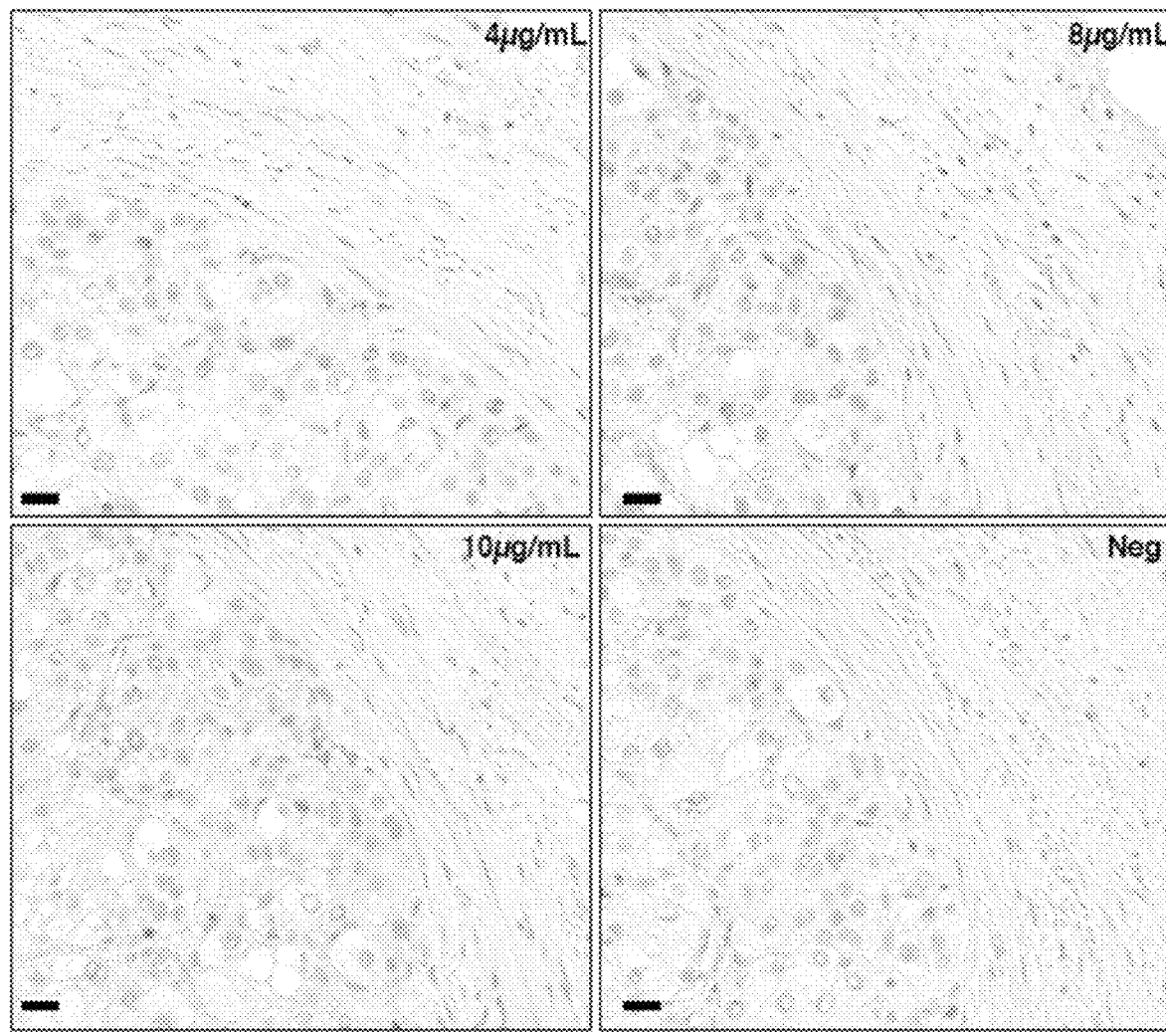
FIG. 7 sets forth an illustration demonstrating positive 9H2/9K1 staining visualized with DAB (brown) on Human Hepatocellular Carcinoma at 4 μg/ml, 8 μg/ml, and 10 μg/ml (3 images). No-primary negative control was performed to identify nonspecific secondary binding (Neg, bottom right image). The scale bar represents 20 μm.

When Phase II optimization samples were evaluated, no staining was observed at 2 µg/mL for 5H4/5K3 and 9H2/9K1. A strong signal was detected at both 8 µg/mL and 10 µg/mL for 5H4/5K3, as illustrated in FIG. 6. A strong signal was detected at both 8 µg/mL, and 10 µg/mL for 9H2/9K1, with a stronger intensity at 10 µg/mL, as illustrated in FIG. 7.

These results demonstrate that 5H4/5K3 and 9H2/9K1 are notable as leads for the development of diagnostic agents, and also as therapeutic drug products suitable for use in mammals, such as humans, by grafting the CDRs onto a suitable antibody framework that will facilitate the targeting of one or more drug products to cancerous tissues in a human subject.

Example 10B—Analysis of MAbs by Immunohistochemistry (IHC)—Phase III—IHC on Tissue Micro Arrays Immunohistochemistry (IHC) was performed on a Leica Bond automated immunostainer using 5H4/5K3 at 8 µg/mL on TMAs (Table #T5).

Heat induced antigen retrieval was performed using Leica Bond Epitope Retrieval Buffer 2 (EDTA solution, pH9.0) for 20 minutes (ER2(20)). Non-specific antibody binding was blocked using 3% Normal Goat Serum in PBST.

Positivity was detected using Novocastra Bond Refine Polymer Detection and visualized with 3'3-diaminobenzidine (DAB; brown). A Hematoxylin nuclear counterstain (blue) was applied.

Isotype controls were performed on Human Hepatocellular carcinoma slide and each TMA type alongside their respective positive (with primary) slide using Rabbit IgG (Abcam ab172730, lot #GR3179509-3).

A human hepatocellular carcinoma FFPE block was sectioned at 4 um thickness and mounted onto positively charged slides for assay development.

TABLE #T6

Tissue Micro Arrays used for IHC staining in Phase III

| Array Name | Tissue Type |
|---|---|
| LV12 | Liver cancer tissue array with progressive changes |
| NT01 | Normal Human Tissue |
| PC02 | Pancreatic cancer tissue array |
| OV01 | Ovary cancer tissue array |
| OV03 | Ovary cancer tissue array with progressive changes |

FIG. 8 sets forth an illustration demonstrating 5H4/5K3 Phase III on TMAs for samples labeled as LV12 Core F4 (top panel), and LV12 Core F4-Isotype (bottom panel). Positive 5H4/5K3 staining was visualized with DAB (brown). Isotype negative control was performed with Rabbit IgG (right images). The scale bar represents 20 µm.

FIG. 9 sets forth an illustration demonstrating 5H4/5K3 Phase III on TMAs for samples labeled as PCO2 Core A6 (top panel), and PCO2 Core A6-Isotype (bottom panel).

FIG. 10 sets forth an illustration demonstrating 5H4/5K3 Phase III on TMAs for samples labeled as OV03 Core C5 (top panel), and OV03 Core C5-Isotype (bottom panel).

FIG. 11 sets forth an illustration demonstrating 5H4/5K3 Phase III on TMAs for samples labeled as OV01 Core D2 (top panel), and OV01 Core D2-Isotype (bottom panel).

These results demonstrate that antibody 5H4/5K3 stains a broad range of ovarian cancer samples, from granuloma to serous to endometrioid cancers. Malignant cancers stain intensely, while benign and normal ovarian tissue samples do not stain under these conditions.

These and similar antibodies, plus fragments or derivatives thereof, should be useful as a key reagent in a kit to diagnose the presence of cancer cells in wide variety of research and clinical samples.

These and similar antibodies, plus fragments or derivatives thereof, may also be useful in the development of pharmaceutical compositions comprising a therapeutic agent when the CDRs are grafted onto an appropriate framework suitable to produce a drug product suitable for mammals, particularly non-human primate and human subjects, and livestock, and domestic pets, including dogs and cats.

Figure 12:
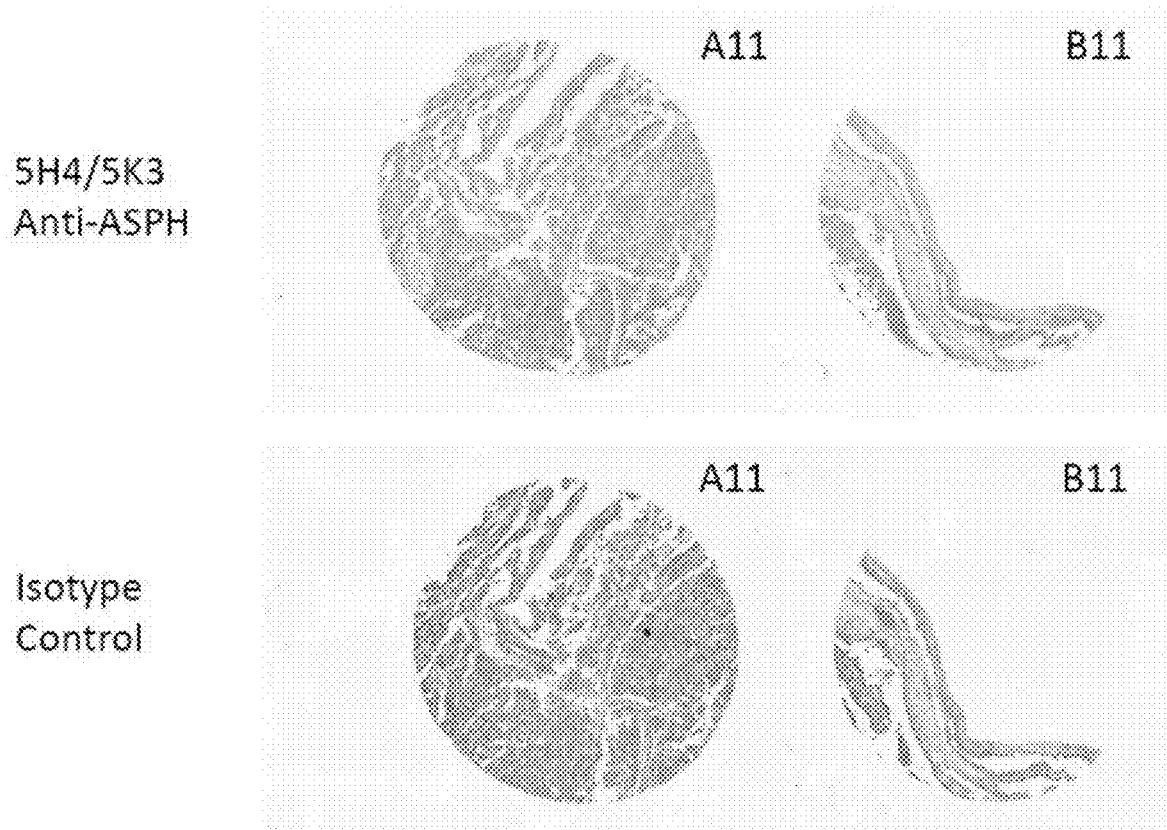
FIG. 12 sets forth an illustration demonstrating activity of 5H4/5K3 Against Granulosa Cell Tumor Samples (A11 and B11). Positive 5H4/5K3 staining was visualized with DAB (brown) Against Granulosa Cell Tumor (top images, A11 and B11) Isotype negative control was performed with Rabbit IgG (bottom images, A11 and B11).

Example 10C—Analysis of MAbs by Immunohistochemistry (IHC)—Phase III—IHC on Tissue Micro Arrays FIG. 12 sets forth an illustration demonstrating activity of 5H4/5K3 Against Granulosa Cell Tumor Samples (A11 and B11). Positive 5H4/5K3 staining was visualized with DAB (brown) against Granulosa Cell Tumor (top images, A11 and B11). Isotype negative control was performed with Rabbit IgG (bottom images, A11 and B11).

Figure 13:
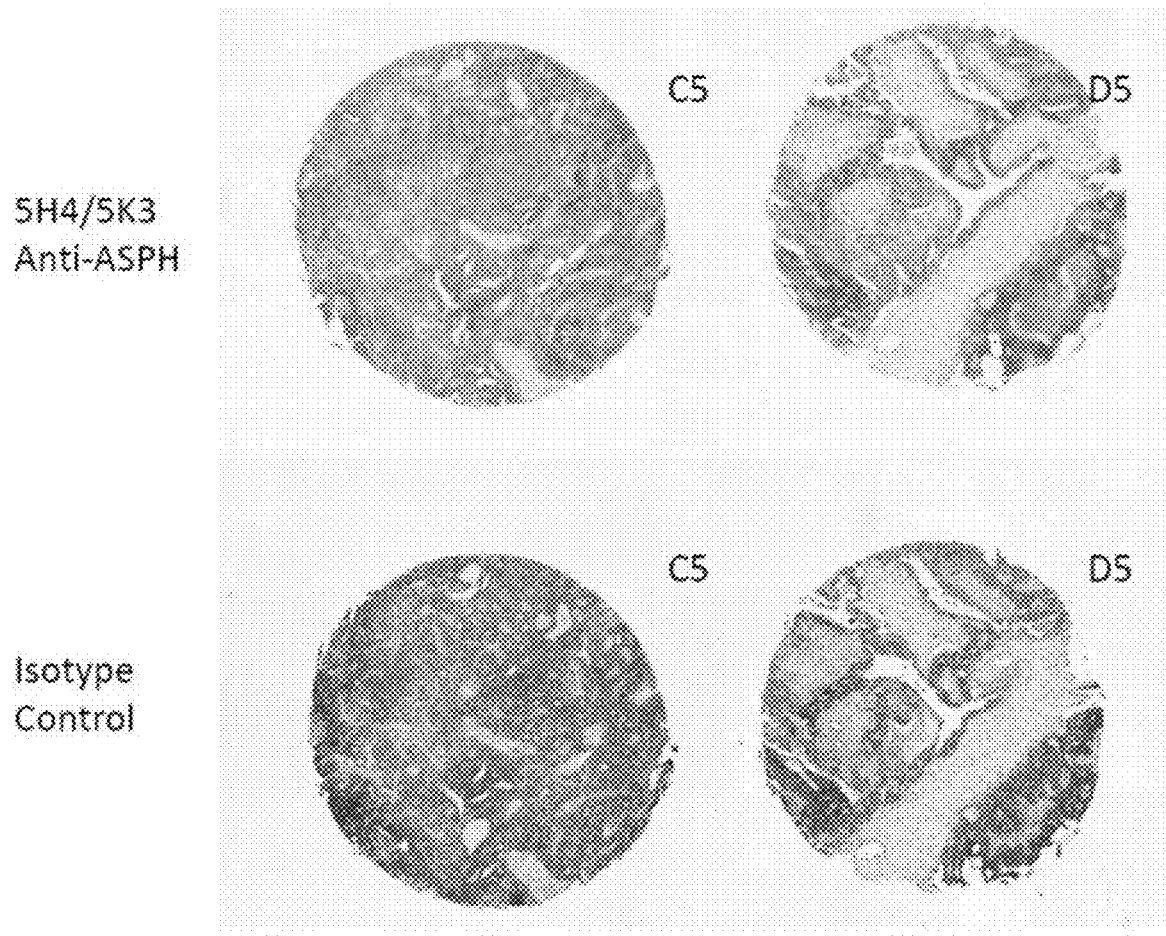
FIG. 13 sets forth an illustration demonstrating activity of 5H4/5K3 Against Serrous Cystadenocarcinoma Stage III Samples (C5 and D5). Positive 5H4/5K3 staining was visualized with DAB (brown) against Serrous Cystadenocarcinoma Stage III (top images, C5 and D5). Isotype negative control was performed with Rabbit IgG (bottom images, C5 and D5).

FIG. 13 sets forth an illustration demonstrating activity of 5H4/5K3 Against Serrous Cystadenocarcinoma Stage III Samples (C5 and D5).

Figure 14:
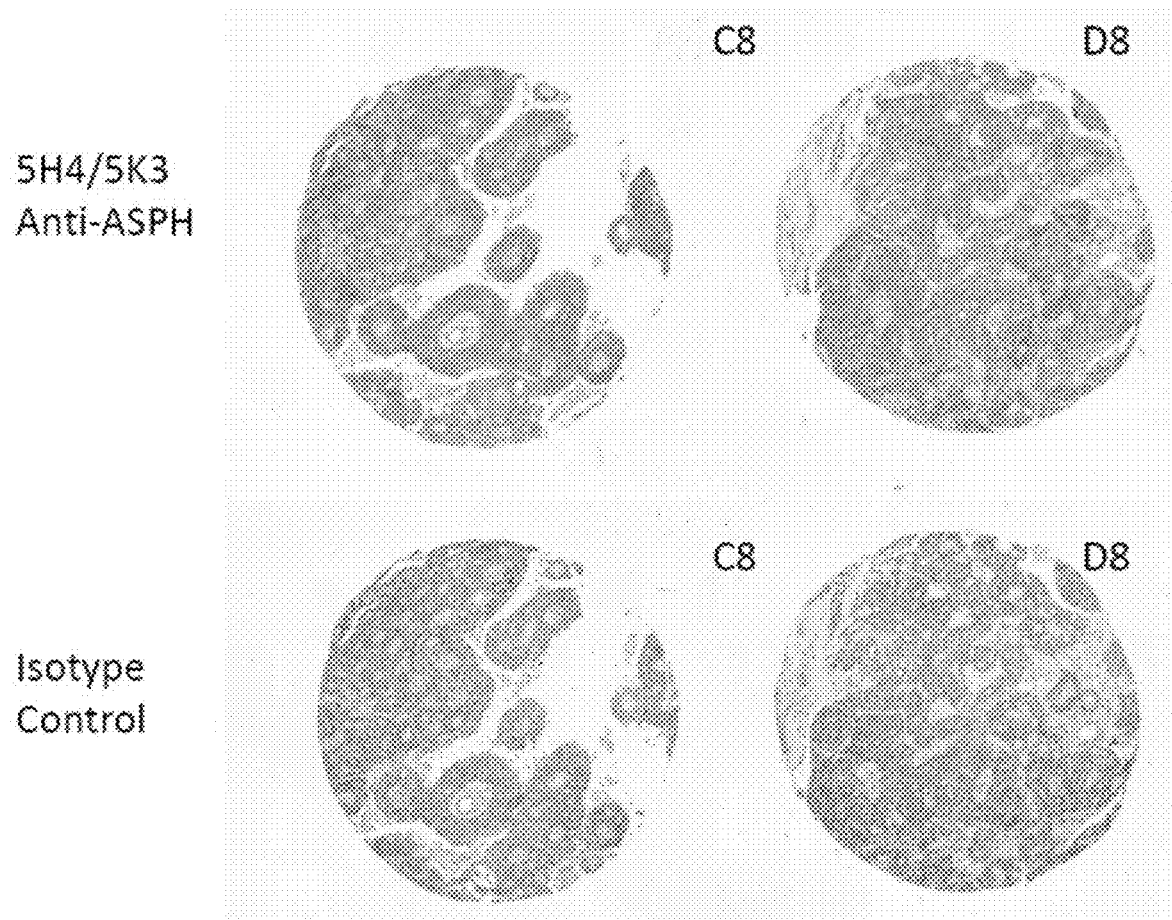
FIG. 14 sets forth an illustration demonstrating activity of 5H4/5K3 Against Serrous Cystadenocarcinoma Stage III Samples (C8 and D8). Positive 5H4/5K3 staining was visualized with DAB (brown) against Serrous Cystadenocarcinoma Stage III (top images, C8 and D8). Isotype negative control was performed with Rabbit IgG (bottom images, C8 and D8).

FIG. 14 sets forth an illustration demonstrating activity of 5H4/5K3 Against Serrous Cystadenocarcinoma Stage III Samples (C8 and D8).

Figure 15:
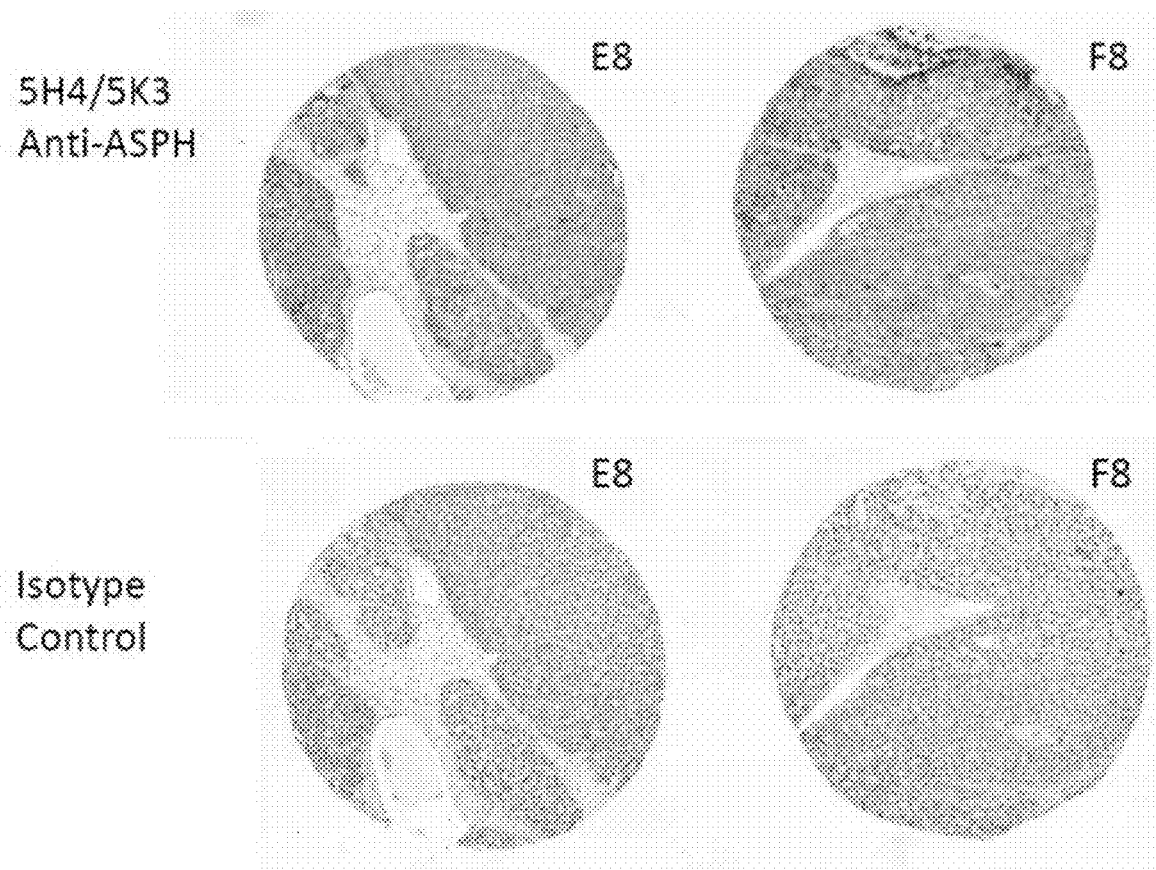
FIG. 15 sets forth an illustration demonstrating activity of 5H4/5K3 Against Endometrioid Adenocarcinoma Stage III Samples (E8 and F8). Positive 5H4/5K3 staining was visualized with DAB (brown) against Endometrioid Adenocarcinoma Stage III (top images, E8 and F8). Isotype negative control was performed with Rabbit IgG (bottom images, E8 and F8).

FIG. 15 sets forth an illustration demonstrating activity of 5H4/5K3 Against Endometrioid Adenocarcinoma Stage III Samples (E8 and F8).

Figure 16:
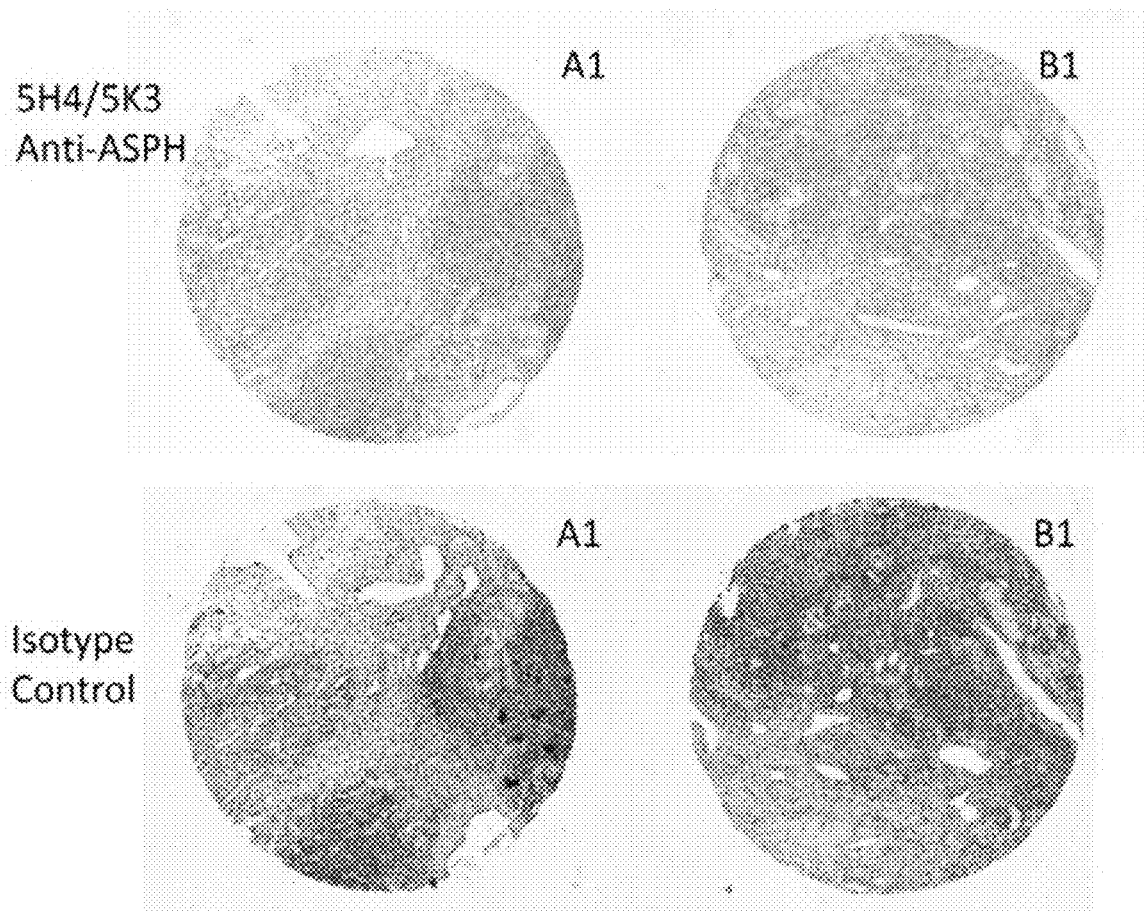
FIG. 16 sets forth an illustration demonstrating reaction of 5H4/5K3 Against Normal Ovarian Tissue Samples (A1 and B1). Lack of 5H4/5K3 staining by DAB against Normal Ovarian Tissue is shown in top images, A1 and B1. Isotype negative control was performed with Rabbit IgG (bottom images, A1 and B1).

FIG. 16 sets forth an illustration demonstrating reaction of 5H4/5K3 Against Normal Ovarian Tissue Samples (A1 and B1).

Figure 17:
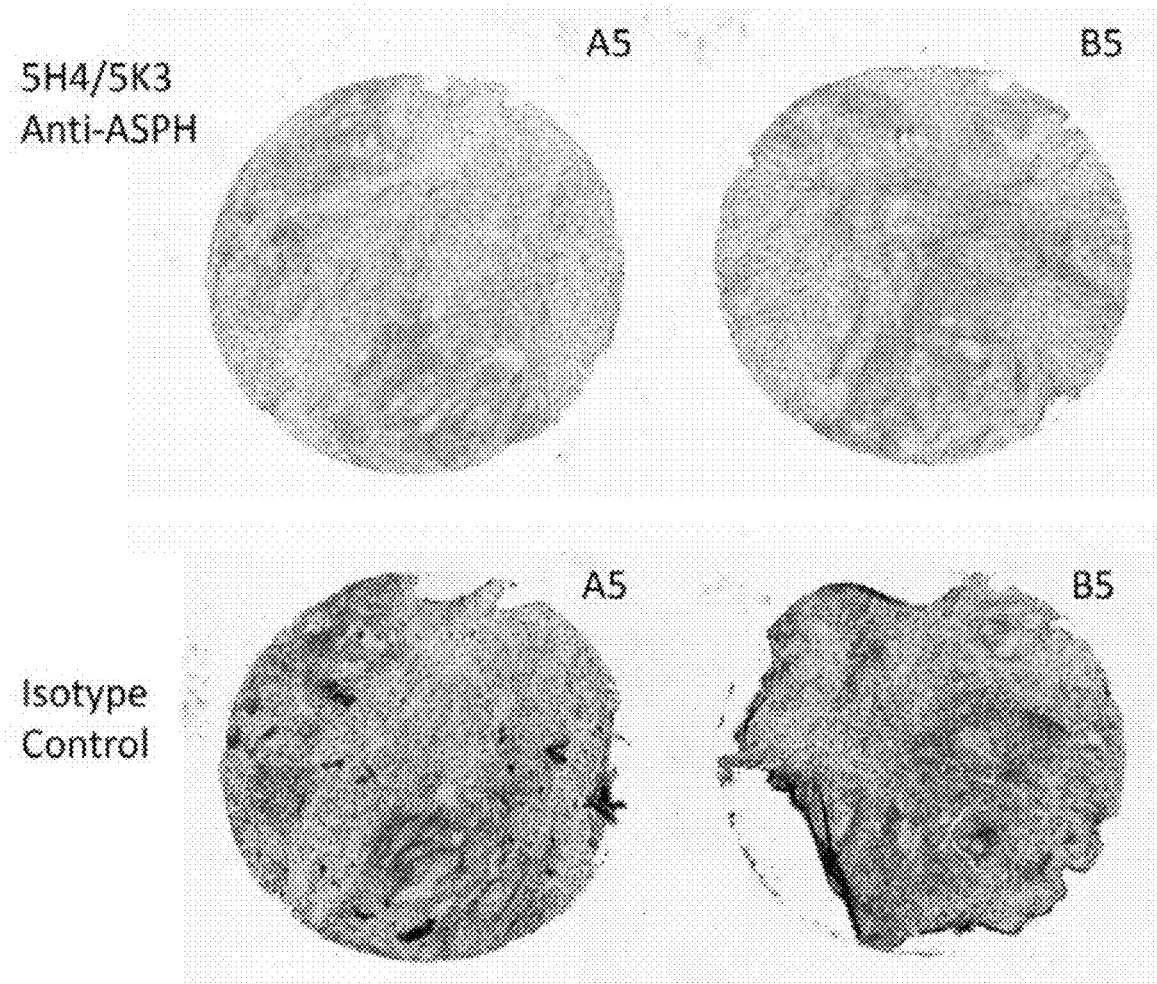
FIG. 17 sets forth an illustration demonstrating reaction of 5H4/5K3 against Thecoma (Theca Cell) Tumor Tissue (A5 and B5). 5H4/5K3 staining was visualized with DAB (brown, top images) against Thecoma (Theca Cell) Tumor Tissue (A5 and B5). Isotype negative control was performed with Rabbit IgG (bottom images, A5 and B5).

FIG. 17 sets forth an illustration demonstrating reaction of 5H4/5K3 Against Thecoma (Theca Cell) Tumor Tissue (A5 and B5).

These results confirm activity of the 5H4/5K3 antibody against a variety of cancerous tissue samples, and a lack of activity against cells in normal tissue samples.

Example 11—Interactions Between ASPH and Selected MAbs Captured Via Protein G The interaction between ASPH and a set of 6 antibodies were characterized by Essai Sciences LLC (Stillwater, Okla.) on a SensiQ Pioneer SPR Platform. The COOH2 sensor chip, which contains a planar dextran surface, was used for target immobilization. The buffer system was 10 mM HEPES, pH 7.4, 150 mM NaCl, and 0.01% Tween-20.

Figure 18:
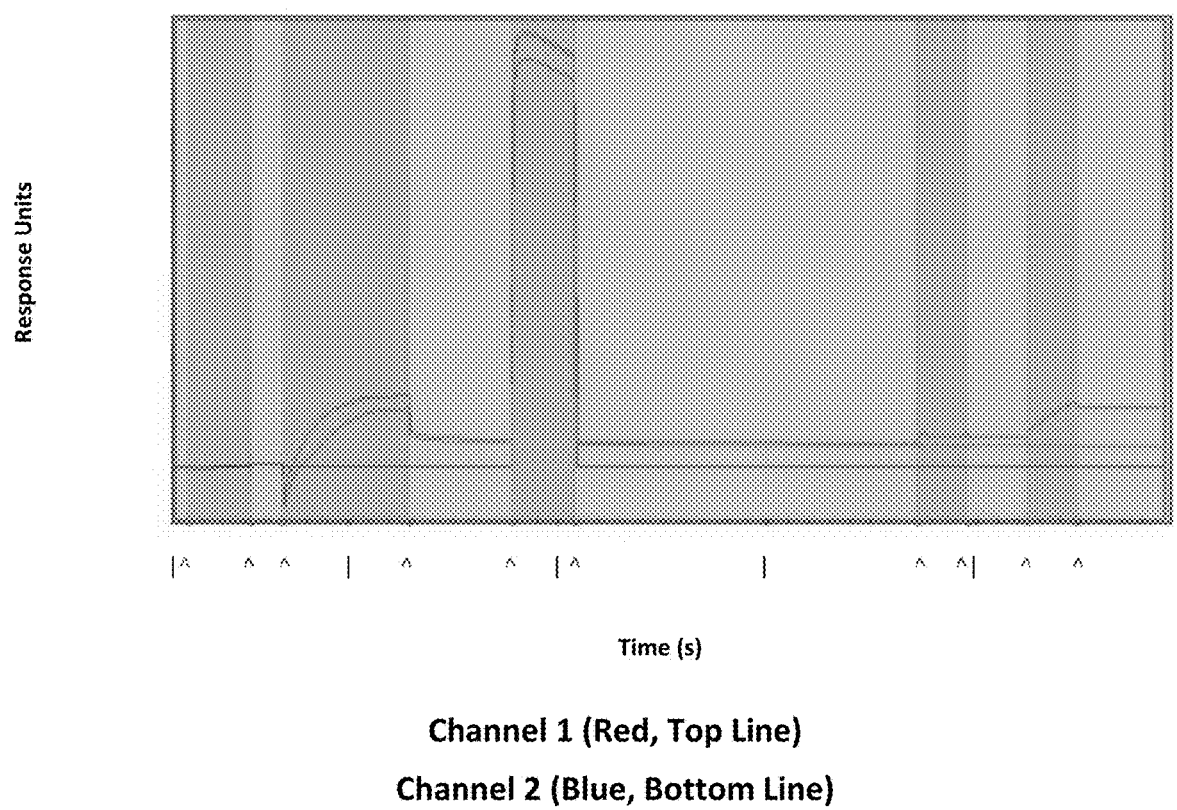
FIG. 18 sets forth an illustration demonstrating Immobilization of Protein G on Channels 1 (Red, top line) and 2 (Blue, bottom line) followed by Capture of Antibody on Channel 1.

All channels of a COOH2 sensor chip were activated with a five-minute injection of 40 mM EDC and 10 mM NHS. Protein G was then injected across channels 1 and 2. 1 M ethanolamine, pH 8.0 was then injected across all three channels. Approximately 1000 response units of Protein G were captured on both channels 1 and 2 (FIG. 18). For each antibody-ASPH interaction, the antibody was injected on channel 1, leaving channels 2 and 3 as a Protein G reference and empty channel reference, respectively. After antibody capture, ASPH was injected at a single concentration. Following injection of ASPH, all three channels were injected with 10 mM NaOH for one minute to regenerate the Protein G surface. This was done twice for each antibody, at each tested concentration of ASPH.

All experimental results shown are from fixed-concentration analyses of the interactions. Given material constraints, as well as the nature of the interacting molecules, immobilization of the antibodies, and fixed-concentration injection of ASPH was the most feasible experimental setup for this study.

Figure 19:
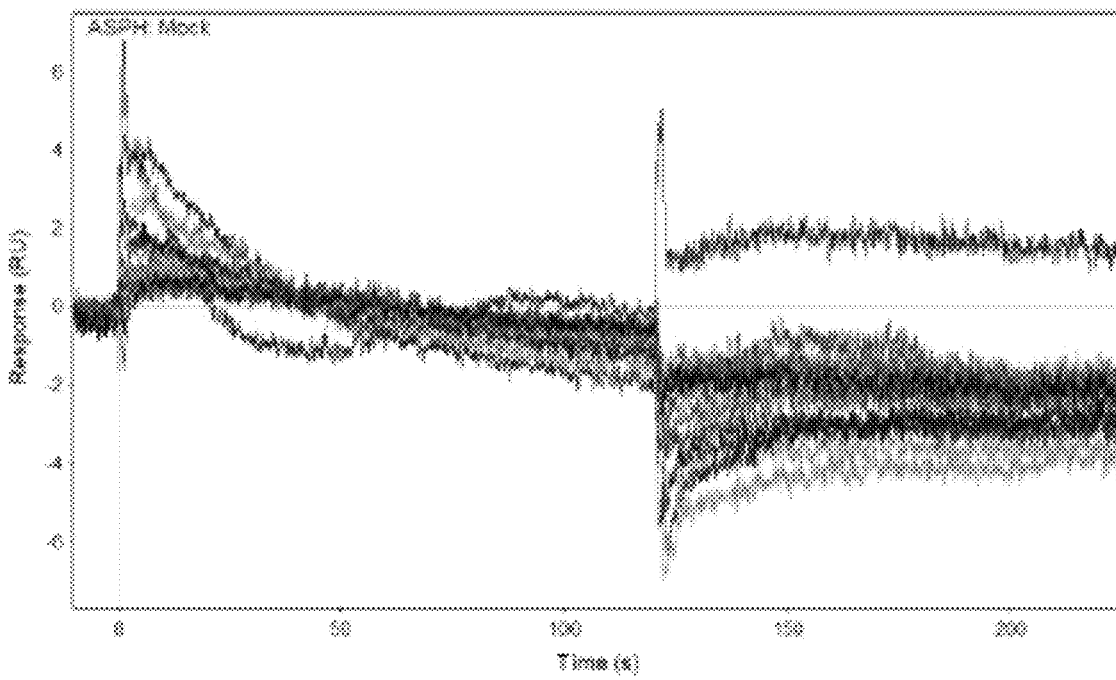
FIG. 19 sets forth an illustration demonstrating Interaction of ASPH with Mock sample. Concentrations are 500 nM (dark red, top line on right portion of the graph), 250 nM (light green), 125 nM (blue), 62.5 nM (dark green) 31.2 nM (orange), 15.6 nM (red).
Figure 20:
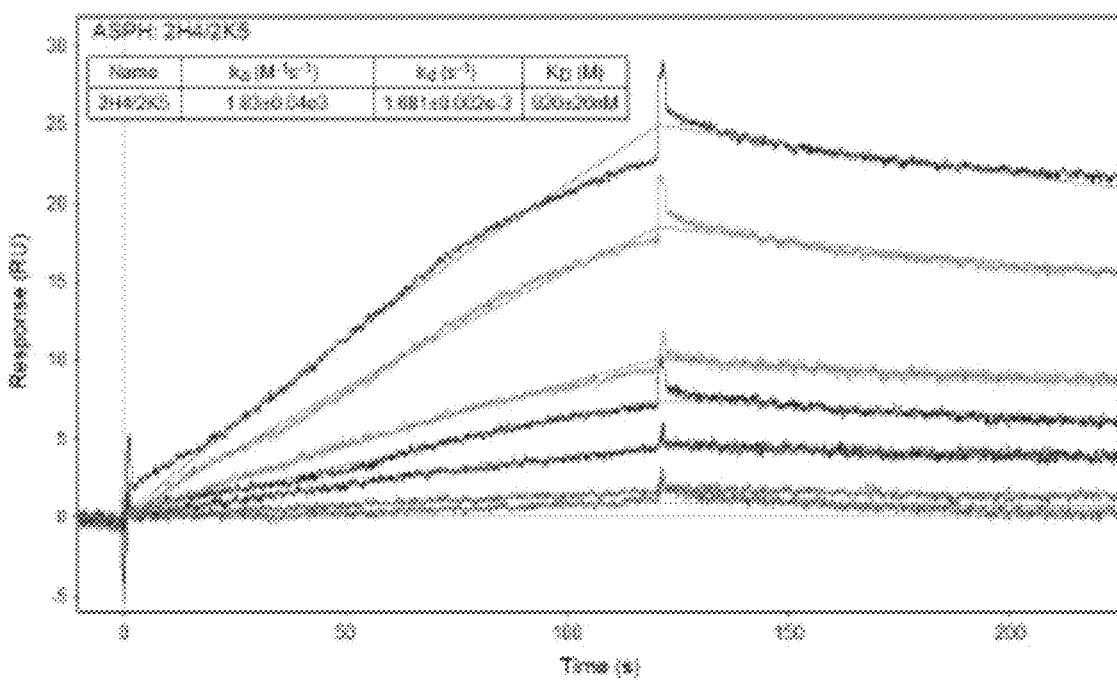
FIG. 20 sets forth an illustration demonstrating Interaction of ASPH with 2H4/2K5. Concentrations are 500 nM (dark red, 1$^{st}$ line from top), 250 nM (light green, 2$^{nd}$ and 3$^{rd}$ lines from top), 125 nM (blue, 4$^{th}$ and 5$^{th}$ lines from top), and 62.5 nM (dark green, 6$^{th}$ and 7$^{th}$ lines from top).
Figure 21:
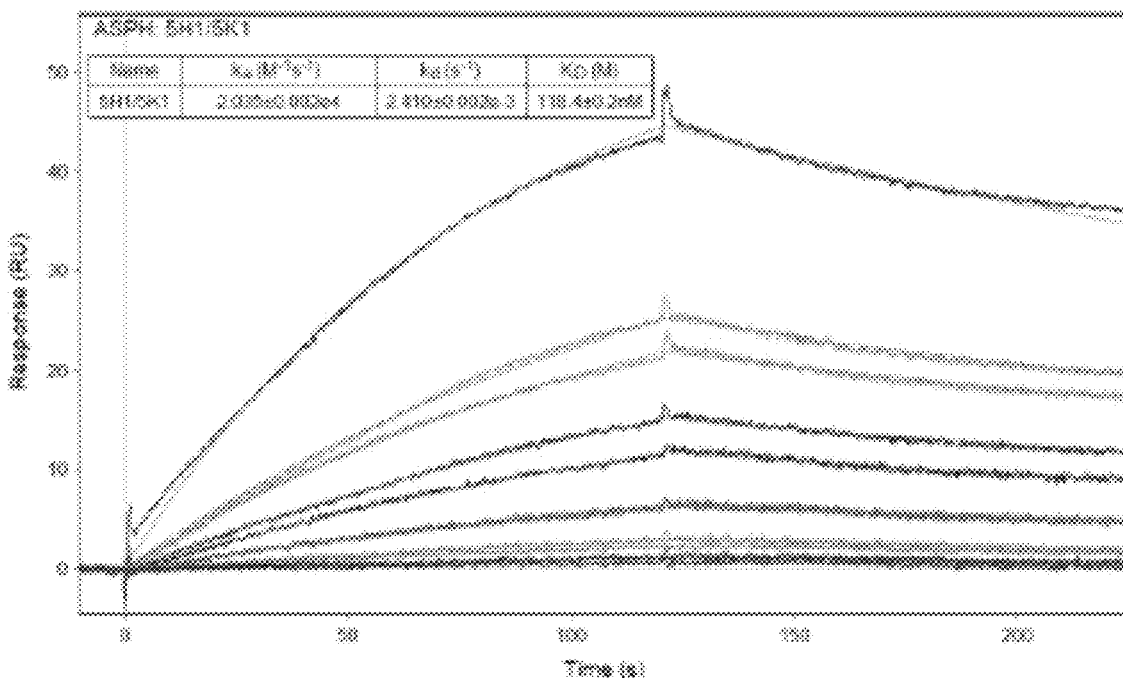
FIG. 21 Interaction of ASPH with 5H1/5K1. Concentrations are 500 nM (dark red, 1$^{st}$ line from top), 250 nM (light green, 2$^{nd}$ and 3$^{rd}$ lines from top), 125 nM (blue, 4$^{th}$ and 5$^{th}$ lines from top), 62.5 nM (dark green, 6$^{th}$ and 7$^{th}$ lines from top), 31.2 nM (orange, 8$^{th}$ and 9$^{th}$ lines from top), and 15.6 nM (red, 10$^{th}$ and 11$^{th}$ lines from top).
Figure 22:
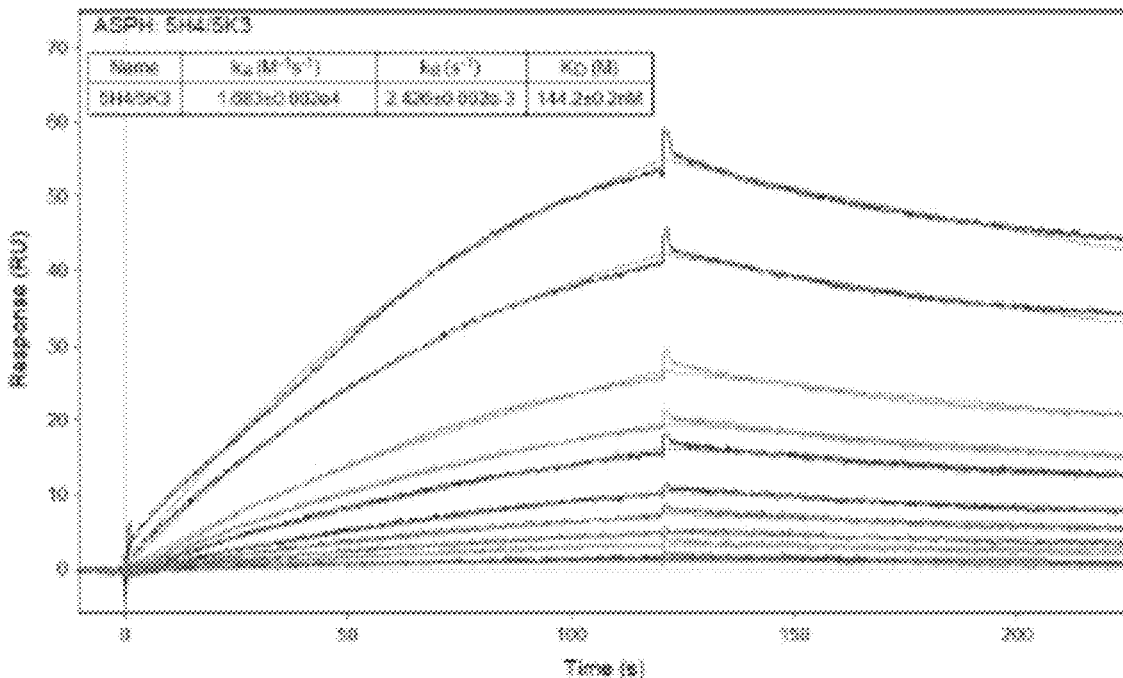
FIG. 22 sets forth an illustration demonstrating Interaction of ASPH with 5H4/5K3. Concentrations are 500 nM (dark red, 1$^{st}$ and 2$^{nd}$ lines from top), 250 nM (light green, 3$^{rd}$ and 4$^{th}$ lines from top), 125 nM (blue, 5$^{th}$ and 6$^{th}$ lines from top), 62.5 nM (dark green, 7$^{th}$ and 8$^{th}$ lines from top), 31.2 nM (orange, 9$^{th}$ and 10$^{th}$ lines from top), and 15.6 nM (red, 11$^{th}$ and 12$^{th}$ lines from top).
Figure 23:
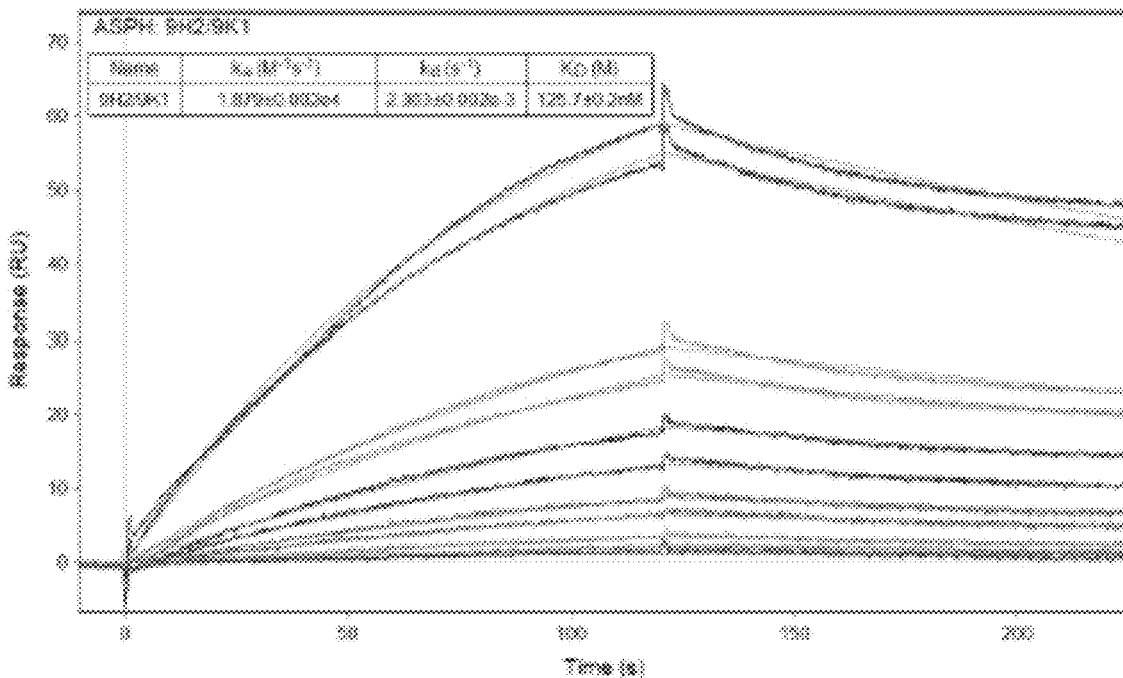
FIG. 23 sets forth an illustration demonstrating Interaction of ASPH with 9H2/9K1. Concentrations are 500 nM (dark red, 1$^{st}$ and 2$^{nd}$ lines from top), 250 nM (light green, 3$^{rd}$ and 4$^{th}$ lines from top), 125 nM (blue, 5$^{th}$ and 6$^{th}$ lines from top), 62.5 nM (dark green, 7$^{th}$ and 8$^{th}$ lines from top), 31.2 nM (orange, 9$^{th}$ and 10$^{th}$ lines from top), and 15.6 nM (red, 11$^{th}$ and 12$^{th}$ lines from top).
Figure 24:
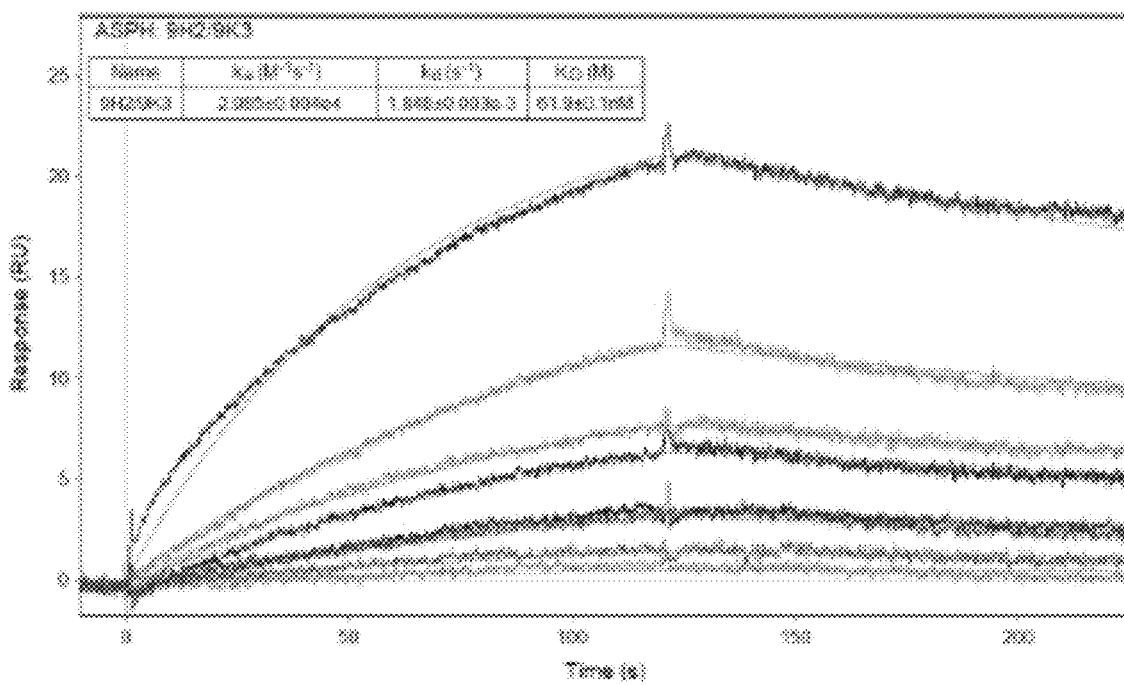
FIG. 24 sets forth an illustration demonstrating Interaction of ASPH with 9H2/9K3. Concentrations are 500 nM (dark red, 1$^{st}$ line from top), 250 nM (light green, 2$^{nd}$ and 3$^{rd}$ lines from top), 125 nM (blue, 4$^{th}$ and 5$^{th}$ lines from top), 62.5 nM (dark green, 6$^{th}$ line from top), and 31.2 nM (orange, 7$^{th}$ line from top).
Figure 25:
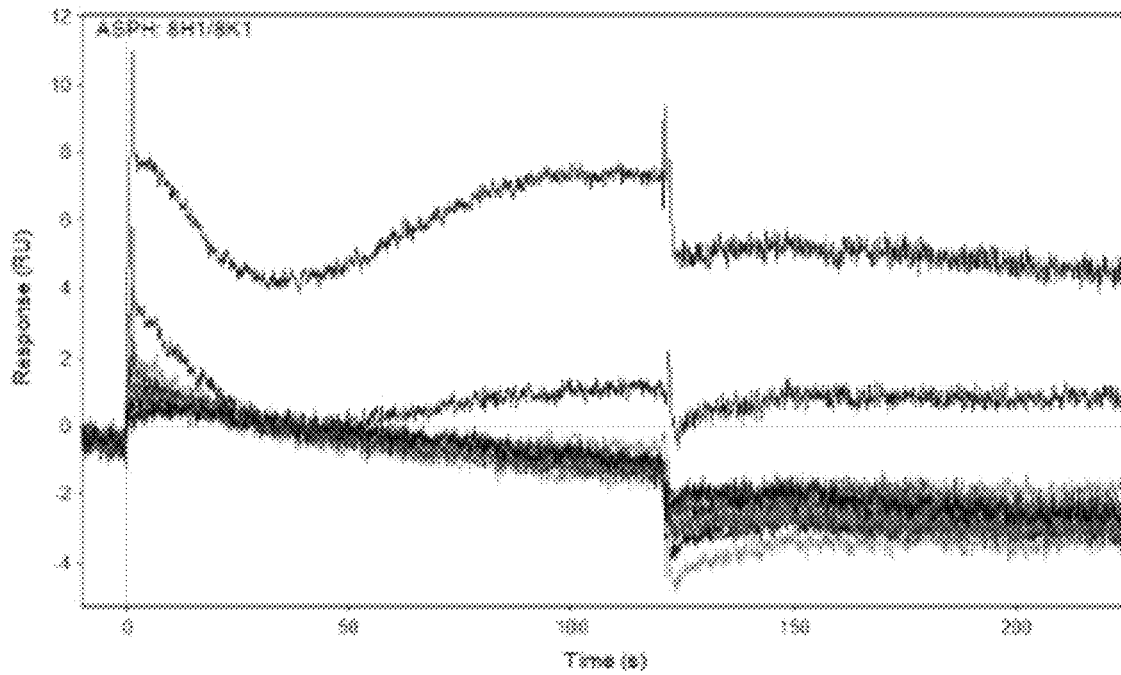
FIG. 25 sets forth an illustration demonstrating Interaction of ASPH with 8H1/8K1. Concentrations are 500 nM (dark red, first and second lines from the top), 250 nM (light green), 125 nM (blue), 62.5 nM (dark green) 31.2 nM (orange), 15.6 nM (red).

The response curves for each tested concentration of ASPH against each captured antibody are displayed below. FIG. 19 is the mock sample, which demonstrates no visible binding. The remaining antibodies (FIGS. 20-25) display affinity for ASPH that range from ~60 nM (9H2/9K3, FIG. 24) to 920 nM (2H4/2K5, FIG. 22). We tested the phospho-selective antibody, 8H1/8K1 (FIG. 25), and observed no binding, even at the highest tested analyte concentration. The kinetics values for each interaction are listed in Table #T7.

TABLE #T7

Kinetics values for interaction of ASPH with antibodies.

| Antibody | ka (M$^{-1}$s$^{-1}$) | kd (s$^{-1}$) | K$_D$ (M) |
|---|---|---|---|
| Mock | — | — | — |
| 2H4/2K5 | 1.83 ± 0.04e3 | 1.681 ± 0.002e-3 | 920 ± 20 nM |
| 5H1/5K1 | 2.035 ± 0.002e4 | 2.410 ± 0.002e-3 | 118.4 ± 0.2 nM |
| 5H4/5K3 | 1.683 ± 0.002e4 | 2.426 ± 0.002e-3 | 144.2 ± 0.2 nM |
| 9H2/9K1 | 1.879 ± 0.002e4 | 2.363 ± 0.002e-3 | 125.7 ± 0.2 nM |
| 9H2/9K3 | 2.985 ± 0.004e4 | 1.848 ± 0.003e-3 | 61.9 ± 0.1 nM |
| 8H1/8K1 | — | — | — |

The interaction of the ASPH protein with a set of antibodies captured via Protein G was studied. A range of affinities from ~60 nM to ~920 nM for the binding antibodies was observed. A mock sample, and a phospho-selective antibody were also tested. No observable binding to the protein for the mock sample or the phospho-selective antibody was noted.

Example 12—In Vitro Cell Proliferation Assay with Antibodies Against Epitopes of ASPH in Three Tumor Cell Lines Experiments to determine the half maximal inhibitory concentration (IC$_{50}$) of the potency of samples comprising selected antibodies in different types of cultured tumor cells were carried out by Translational Drug Development LLC.

Figure 26:
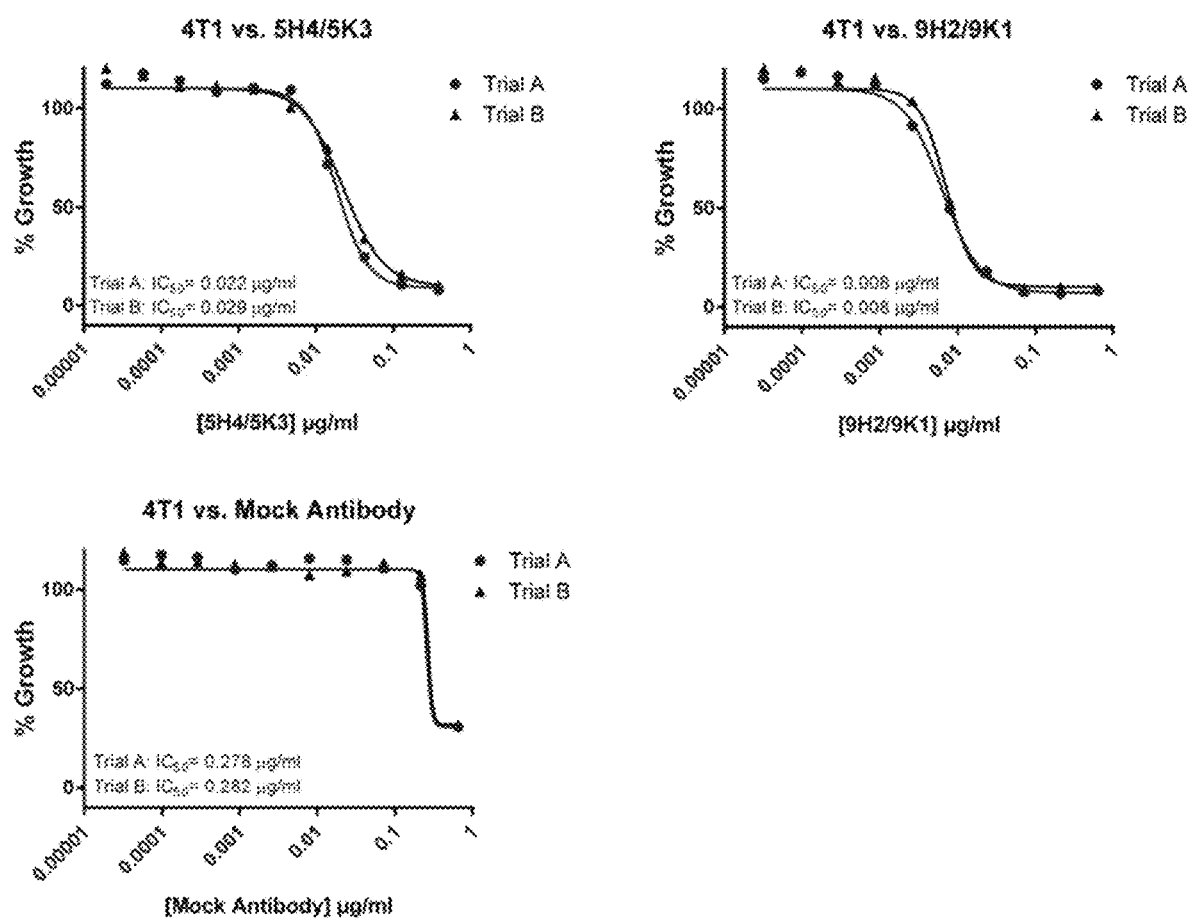
FIG. 26 sets forth an illustration demonstrating IC50 Curves for 5H4/5K3, 9H2/9K1 and Mock Antibody Samples Carried Out in 4T1 Cells.

FIG. 26 shows graphs illustrating IC$_{50}$ curves for three samples tested in 4T1 Murine Breast Tumor cells (Panel A, 5H4/5K3; Panel B, 9H2/9K1; and Panel C, Mock Antibody).

Figure 27:
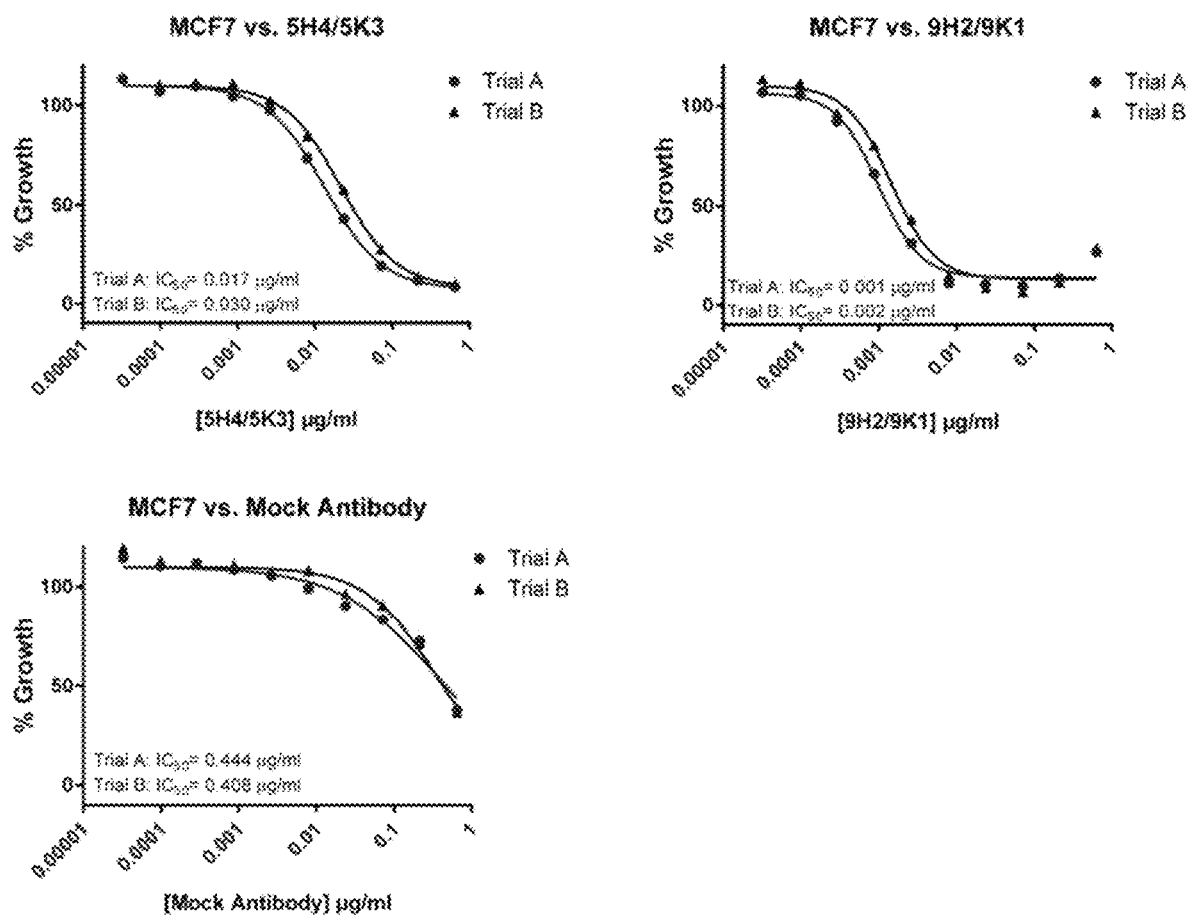
FIG. 27 sets forth an illustration demonstrating IC50 Curves for 5H4/5K3, 9H2/9K1 and Mock Antibody Samples Carried Out in MCF7 Cells.

FIG. 27 shows graphs illustrating IC$_{50}$ curves for three samples tested in MCF-7 Human ER+ Breast Tumor cells (Panel A, 5H4/5K3; Panel B, 9H2/9K1; and Panel C, Mock Antibody).

Figure 28:
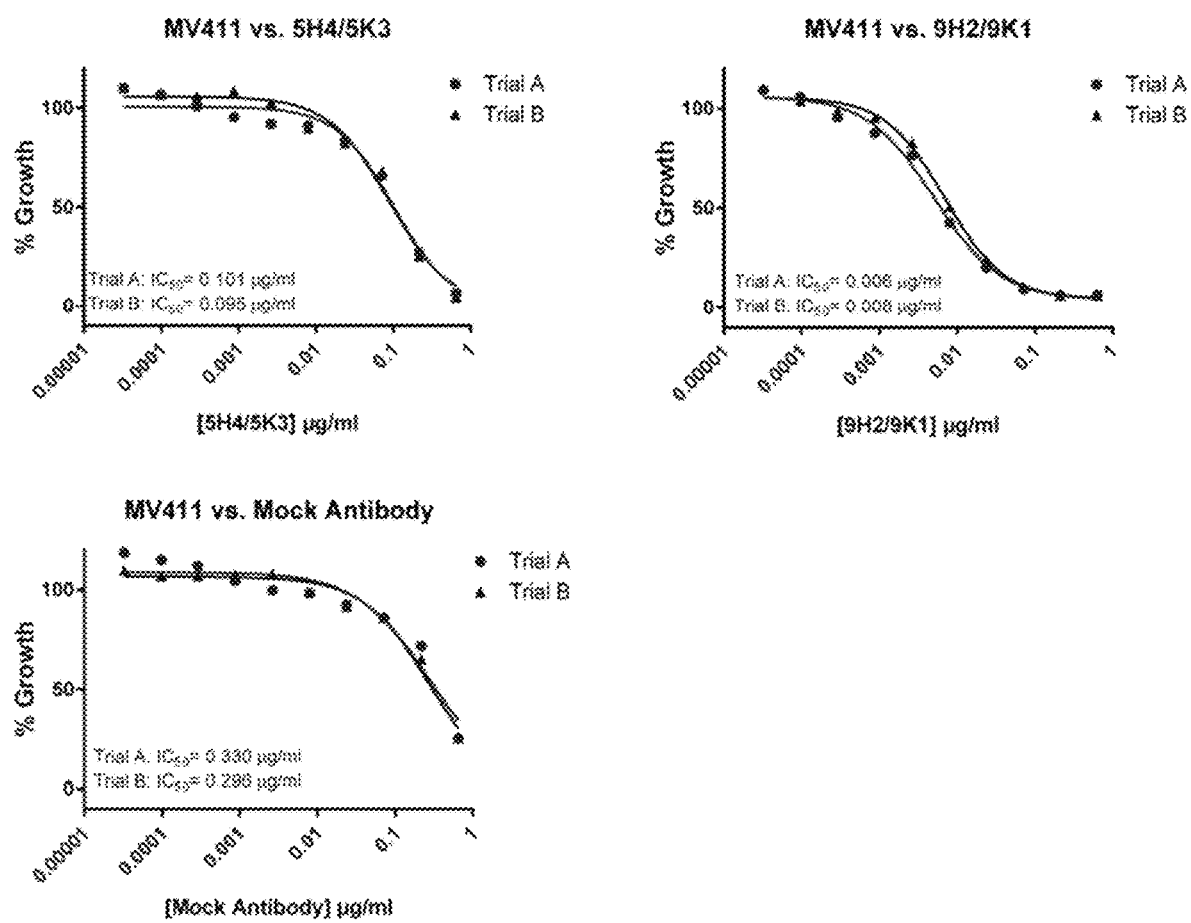
FIG. 28 sets forth an illustration demonstrating IC50 Curves for 5H4/5K3, 9H2/9K1 and Mock Antibody Samples Carried Out in MV411 Cells.

FIG. 28 shows graphs illustrating IC$_{50}$ curves for three samples tested in MV411 Human Mantle Cell Leukemia cells (Panel A, 5H4/5K3; Panel B, 9H2/9K1; and Panel C, Mock Antibody).

TABLE #T8

Summary of IC$_{50}$ Results*

| Cell Line | Tissue Type | Mean IC$_{50}$ (µg/mL) 5H4/5K3 | Mean IC$_{50}$ (µg/mL) 9H2/9K1 | Mean IC$_{50}$ (µg/mL) Mock Antibody |
|---|---|---|---|---|
| 4T1 | Murine Breast Tumor | 0.026 | 0.008 | 0.280 |
| MCF-7 | Human ER+ Breast Tumor | 0.024 | 0.002 | 0.426 |
| MV411 | Human Mantle Cell Leukemia | 0.098 | 0.007 | 0.313 |

*Mean IC values are calculated as the average of IC$_{50}$ values obtained from two trials, A and B, for each of 3 antibody experiments in 3 cell lines, as noted in Panels A-C of FIGS. 26 through 28.

These results demonstrate that the antibodies designated as 5H4/5K3 and 9H2/9K1 both affect the viability of three tumor cell lines being tested, with the Mab designated 9H2/9K1 being more potent than the Mab designated 5H4/5K3.

The antibody designated as 5H4/5K3 appears to be more selective for breast tumors 4T1 and MCF-7.

Example 13—Generation of Humanized Chimeric Monoclonal Antibodies Targeting at Least One Epitope in the Catalytic Domain of ASPH Humanized versions of non-human antibodies are chimeric antibodies that a minimal amount of polypeptide domains comprising amino acid sequences derived from the non-human antibody. Typically, residues from the hypervariable region of a human antibody are replaced with hypervariable residues from the non-human antibody, that have the desired specificity, affinity, and/or capacity. Humanized versions can also be prepared from non-human species, such as mouse, rat, rabbit, non-human primates, and other vertebrate species. Other regions, comprising amino acid residues that may contribute to structural integrity of the human antibody (framework region) may also be replaced by amino acid residues from the corresponding non-human residues. The humanized chimeric monoclonal antibodies may also comprise amino acid residues that are not found in the recipient human antibody or the non-human donor antibody. Generally, the humanized antibody comprises at least one, and preferably all of the variable domains of the donor antibody, and substantially all of the framework regions of the human antibody.

Variants may also comprise one or more portions of the constant region of an antibody, typically, a human antibody. Other types of variants, include fragments, and variants comprising one or more conservative substitutions, insertions, or deletions, that do not substantially alter the specificity, affinity, and/or capacity of the variant molecule compared to its parent molecule, but may offer additional advantages in terms of ease of production or purification, ability to be conjugated to other chemical moieties, which may facilitate covalent or non-covalent binding to other molecules comprising polypeptide domains or other reactive or non-reactive moieties, capable of providing a secondary reporter function, such as emission of fluorescent light, or conversion of a colorless substrate to an easily detectable, colored product, which may be useful as components in diagnostic kits for use in research and in clinical settings. Aspects of the invention also include variants that are >80%, >85%, >90%, >91%, >92%, >93%, >94%, >95%, >96%, >98%, >99%, or >99.5% identical to at least one of the variable regions of the donor antibody.

In the examples noted above, recombinant monoclonal antibodies were generated against Peptide #1 (SEQ ID NO: 13). Recombinant Clones 5H1, 5H3, 5H4, and 9H2 have the same heavy chain sequences, and recombinant clones 5K1, 5K3 and 9K1 have the same kappa chain sequence. The CDR1 regions from the heavy chain clones include the sequences NFMC (SEQ ID NO: 31) and NAMC (SEQ ID NO: 32). The CDR2 regions from the heavy chain clones include CIYF (SEQ ID NO: 33) and CIDN (SEQ ID NO: 34). The CDR3 regions from the heavy chain clones include DGPGSISWDI (SEQ ID NO: 35) and NFNI (SEQ ID NO: 36). The CDR1 regions from the kappa chain clones include SVYSKNR (SEQ ID NO: 37) and SVYDNNR (SEQ ID NO: 38). The CDR2 regions from the kappa chain clones were all LAS (SEQ ID NO: 39). The CDR3 regions from the kappa chain clones included QGTYDSSGWYWA (SEQ ID NO: 40) and LGSYSGYIYI (SEQ ID NO: 41).

Plasmids comprising cDNAs encoding rabbit antibodies targeting epitopes of ASPH described in Examples 5-8 are used as a source of nucleic acids comprising variable regions to generate humanized monoclonal antibodies that target at least one epitope in the catalytic domain of ASPH. One or more codons within the rabbit cDNAs may be altered to represent codons that are optimally used in the host cell expression system, to enhance expression of the encoded chimeric polypeptide under the control of operably-linked promoters and other genetic elements. Random and targeted mutagenesis of specific residues within the variable regions may result in antibodies that have increased affinity to its intended target, and/or reduced affinity to other targets.

Example 14—Generation of Bispecific Antibodies Targeting at Least One Epitope in the Catalytic Domain of ASPH Bispecific antibodies combine the structural domains of two distinct molecules into one molecule with the goal of preserving and perhaps enhancing functional properties of the chimeric molecule compared to its parent mono-specific molecules (Dahlen E. et al, Bispecific antibodies in cancer immunotherapy. Therapeutic Advances in Vaccines and Immunotherapy, 2018, 6:(1)3-17). In some cases, bispecific antibodies have superior therapeutic properties compared to compositions comprising mixtures of monospecific compounds.

Several classes of immunotherapeutic bispecific antibodies have been recognized, including T-cell redirectors, which act on malignant cells by targeting a tumor antigen and CD3; NK-cell redirectors, which act on malignant cells targeting a tumor antigen and CD16A; Tumor-targeted immunomodulators, which direct co-stimulation of tumor-infiltrating immune cells by targeting a tumor antigen and co-stimulatory molecules, such as CD40 or 4-1BB; and Dual immunomodulators, which simultaneously act on two immunomodulatory targets, resulting in blockade of inhibitory targets, depletion of suppressive cells, or activation of effector cells (See Table 1 of Dahlen et al).

A non-limiting list of exemplary tumor antigens includes CD19, EpCAM, CD20, CD23, BCMA, B7H3, and PSMA.

A non-limiting list of T-cell specific epitopes includes CD3, CD3e, OX40, CD27, ICOS and GITR.

A non-limiting list of co-stimulatory molecules includes CD40 and 4-1BB.

A non-limiting list of immunomodulating targets includes PD-L1, CTLA-4, TGF-β, LAG-2, TIM-3, and OX40.

Bispecific antibodies comprising at least one complementarity-determining region (CDR) targeting one or more epitopes of ASPH selected from the group consisting of CDR1, CDR2, and CDR3 from the heavy chain or the light chain clones of Example 13 are prepared by fusing rabbit, other non-human, human, or humanized antibodies comprising these regions with an antibody targeting one or more tumor antigens, T-cell specific epitopes, co-stimulatory molecules, or immunomodulating targets, as noted above.

Exemplary bi-specific antibodies include a molecule comprising the CDRs of the 5H4/5K3 antibody disclosed herein, where the 5H4 CDR1=NAMC (SEQ ID NO: 31), CDR2=CIDN (SEQ ID NO: 34), and CDR3=NFNI (SEQ ID NO: 36), and where the 5K3 CDR1=SVYDNNR (SEQ ID NO: 38)), CDR2=LAS (SEQ ID NO: 39), CDR3=LGSYSGYIYI (SEQ ID NO: 41) or 9H2/9K1 antibody, where the 9H2 CDR1=NAMC (SEQ ID NO: 32), CDR2=CIDN (SEQ ID NO: 34), and CDR3=NFNI (SEQ ID NO: 36), and the 9K1 CDR1=SVYDNNR (SEQ ID NO: 38), CDR2=LAS (SEQ ID NO: 39), and CDR3=LGSYSGYIYI (SEQ ID NO: 41), combined with an antibody molecule comprising one or more tumor antigens, T-cell specific epitopes, co-stimulatory molecules, or immunomodulating targets, as noted above.

An exemplary bispecific antibody of the T-cell redirector class includes an antibody targeting one or more ASPH CDRs with an antibody targeting CD3.

An exemplary bispecific antibody of the NK-cell redirector class includes an antibody targeting one or more ASPH CDRs with an antibody targeting CD16A.

An exemplary bispecific antibody of the tumor targeting immunomodular class includes an antibody targeting one or more ASPH CDRs with an antibody targeting CD40 or 4-1BB.

An exemplary bispecific antibody of the dual immunomodular class includes an antibody targeting one or more ASPH CDRs with an antibody targeting PD-L1, PD-1, CTLA-4, TGF-β, LAG-3, TIM-3, or OX40.

Statement Regarding Preferred Aspects are Meant to be Illustrative and not Limiting as to the Scope of the Invention While the preferred aspects of the invention have been illustrated and described in detail, it will be appreciated by those skilled in the art that that various changes can be made therein without departing from the spirit and scope of the invention. Accordingly, the particular arrangements disclosed are meant to be illustrative only and not limiting as to the scope of the invention, which is to be given the full breadth of the appended claims and any equivalent thereof.

BIBLIOGRAPHY

Statement Regarding Incorporation by Reference of Journal Articles and Patent Documents All references, patents, or applications cited herein are incorporated by reference in their entirety, as if written herein.

Journal Articles

Aihara, A., C. K. Huang, M. J. Olsen, Q. Lin, W. Chung, Q. Tang, X. Dong and J. R. Wands (2014). "A cell-surface beta-hydroxylase is a biomarker and therapeutic target for hepatocellular carcinoma." Hepatology 60(4): 1302-1313.

Borgas, D. L., J. S. Gao, M. Tong and S. M. de la Monte (2015). "Potential Role of Phosphorylation as a Regulator of Aspartyl-(asparaginyl)-beta-hydroxylase: Relevance to Infiltrative Spread of Human Hepatocellular Carcinoma." Liver Cancer 4(3): 139-153.

Borgas, D. L., J. S. Gao, M. Tong, N. Roper and S. M. de la Monte (2015). "Regulation of Aspartyl-(Asparaginyl)-beta-Hydroxylase Protein Expression and Function by Phosphorylation in Hepatocellular Carcinoma Cells." J Nat Sci 1(4).

Cantarini, M. C., S. M. de la Monte, M. Pang, M. Tong, A. D'Errico, F. Trevisani and J. R. Wands (2006). "Aspartyl-asparagyl beta hydroxylase over-expression in human hepatoma is linked to activation of insulin-like growth factor and notch signaling mechanisms." Hepatology 44(2): 446-457.

Dinchuk, J. E., R. J. Focht, J. A. Kelley, N. L. Henderson, N. I. Zolotarjova, R. Wynn, N. T. Neff, J. Link, R. M. Huber, T. C. Burn, M. J. Rupar, M. R. Cunningham, B. H. Selling, J. Ma, A. A. Stern, G. F. Hollis, R. B. Stein and P. A. Friedman (2002). "Absence of post-translational aspartyl beta-hydroxylation of epidermal growth factor domains in mice leads to developmental defects and an increased incidence of intestinal neoplasia." J Biol Chem 277(15): 12970-12977.

Drakenberg, T., P. Fernlund, P. Roepstorff and J. Stenflo (1983). "beta-Hydroxyaspartic acid in vitamin K-dependent protein C." Proc Natl Acad Sci USA 80(7): 1802-1806.

El Asmar, Z., J. Terrand, M. Jenty, L. Host, M. Mlih, A. Zerr, H. Justiniano, R. L. Matz, C. Boudier, E. Scholler, J. M. Garnier, D. Bertaccini, D. Thierse, C. Schaeffer, A. Van Dorsselaer, J. Herz, V. Bruban and P. Boucher (2016). "Convergent Signaling Pathways Controlled by LRP1 (Receptor-related Protein 1) Cytoplasmic and Extracellular Domains Limit Cellular Cholesterol Accumulation." J Biol Chem 291(10): 5116-5127.

Furler, R. L., D. F. Nixon, C. A. Brantner, A. Popratiloff and C. H. Uittenbogaart (2018). "TGF-beta Sustains Tumor Progression through Biochemical and Mechanical Signal Transduction." Cancers (Basel) 10(6). Gundogan, F., G. Elwood, D. Greco, L. P. Rubin, H. Pinar, R. I. Carlson, J. R. Wands and S. M. de la Monte (2007). "Role of aspartyl-(asparaginyl) beta-hydroxylase in placental implantation: Relevance to early pregnancy loss." Hum Pathol 38(1): 50-59.

Iwagami, Y., S. Casulli, K. Nagaoka, M. Kim, R. I. Carlson, K. Ogawa, M. S. Lebowitz, S. Fuller, B. Biswas, S. Stewart, X. Dong, H. Ghanbari and J. R. Wands (2017). "Lambda phage-based vaccine induces antitumor immunity in hepatocellular carcinoma." Heliyon 3(9): e00407.

Lavaissiere, L., S. Jia, M. Nishiyama, S. de la Monte, A. M. Stern, J. R. Wands and P. A. Friedman (1996). "Overexpression of human aspartyl(asparaginyl)beta-hydroxylase in hepatocellular carcinoma and cholangiocarcinoma." J Clin Invest 98(6): 1313-1323.

Noda, T., M. Shimoda, V. Ortiz, A. E. Sirica and J. R. Wands (2012). "Immunization with aspartate-beta-hydroxylase-loaded dendritic cells produces antitumor effects in a rat model of intrahepatic cholangiocarcinoma." Hepatology 55(1): 86-97.

Revskaya, E., Z. Jiang, A. Morgenstern, F. Bruchertseifer, M. Sesay, S. Walker, S. Fuller, M. S. Lebowitz, C. Gravekamp, H. A. Ghanbari and E. Dadachova (2017). "A Radiolabeled Fully Human Antibody to Human Aspartyl (Asparaginyl) beta-Hydroxylase Is a Promising Agent for Imaging and Therapy of Metastatic Breast Cancer." Cancer Biother Radiopharm 32(2): 57-65.

Tong, M., J. S. Gao, D. Borgas and S. M. de la Monte (2013). "Phosphorylation Modulates Aspartyl-(Asparaginyl)-beta Hydroxylase Protein Expression, Catalytic Activity and Migration in Human Immature Neuronal Cerebellar Cells." Cell Biol (Henderson, Nev.) 6(2).

Wu, G., Z. Ma, Y. Cheng, W. Hu, C. Deng, S. Jiang, T. Li, F. Chen and Y. Yang (2018). "Targeting Gas6/TAM in cancer cells and tumor microenvironment." Mol Cancer 17(1): 20.

Yang, H., K. Song, T. Xue, X. P. Xue, T. Huyan, W. Wang and H. Wang (2010). "The distribution and expression profiles of human Aspartyl/Asparaginyl beta-hydroxylase in tumor cell lines and human tissues." Oncol Rep 24(5): 1257-1264.

Yeung, Y. A., A. H. Finney, I. A. Koyrakh, M. S. Lebowitz, H. A. Ghanbari, J. R. Wands and K. D. Wittrup (2007). "Isolation and characterization of human antibodies targeting human aspartyl (asparaginyl) beta-hydroxylase." Hum Antibodies 16(3-4): 163-176.

PDB ID 5JZZ: McDonough, M. A., Pfeffer, I., Munzel, M. (2016) Aspartyl/Asparaginyl beta-hydroxylase (AspH)oxygenase and TPR domains in complex with manganese, N-oxalylglycine and cyclic peptide substrate mimic of factor X. DOI: 10.2210/pdb5JZZ/pdb. Deposited as PDB ID 5JZZ on 2016 May 16, Released on 2017 Jun. 6; Replaced by PDB ID 6RK9 on 2019 May 7.

Dahlen E., Veltonmaki, and Norten, P. (2018) Bispecific antibodies in cancer immunotherapy. *Therapeutic Advances in Vaccines and Immunotherapy* 6(1): 3-17.

What is claimed is:

1. A method of treating cancer in a mammalian subject, comprising administering to a subject in need thereof a composition comprising an antibody or fragment or variant thereof, which binds to one or more peptide epitopes of human aspartyl (asparaginyl) β-hydroxylase (ASPH) in an amount sufficient to treat cancer, wherein said antibody comprises:

a recombinant heavy chain and a recombinant light chain, each heavy and each light chain comprising 3 complementarity-determining regions (CDRs), or fragment or variant thereof, which binds to one or more peptide epitopes of human aspartyl (asparaginyl) β-hydroxylase (ASPH), wherein at least one of said peptide epitopes comprises at least 4 consecutive amino acid residues located within or adjacent to a position in the catalytic domain of ASPH that is within 30 amino acids of the C-terminus of human ASPH, corresponding to the sequence QDASSFRLIFIVDVWHPELTPQQRRSLPAI represented by positions 729-758 of SEQ ID NO: 1;

wherein said antibody or fragment or variant thereof contains one or more conservative amino acid substitutions in which the functional activity relating to binding of the antibody or fragment thereof to an epitope of ASPH is retained;

wherein said antibody comprises a recombinant heavy chain comprising a CDR1 comprising a sequence selected from the group consisting of NFMC represented by SEQ ID NO: 31, and
NAMC represented by SEQ ID NO: 32;
a CDR2 comprising a sequence selected from the group consisting of
CIYF represented by SEQ ID NO: 33, and
CIDN represented by SEQ ID NO: 34; and
a CDR3 comprising a sequence selected from the group consisting of
DGPGSISWKI represented by SEQ ID NO: 35, and
NFNI represented by SEQ ID NO: 36;
wherein said antibody comprises a recombinant light chain comprising
a CDR1 comprising a sequence selected from the group consisting of
SVYSKNR represented by SEQ ID NO: 37, and
SVYDNNR represented by SEQ ID NO: 38;
a CDR2 comprising the sequence
LAS represented by SEQ ID NO: 39; and
a CDR3 comprising a sequence selected from the group consisting of
QGTYDSSGWYWA represented by SEQ ID NO: 40, and
LGSYSGYIYI represented by SEQ ID NO: 41.

2. The method of claim 1, wherein said antibody or fragment or variant binds to one or more peptides selected from the group consisting of
(a) a peptide comprising 29 amino acids with Cysteine at its amino terminus, plus 28 amino acids corresponding to positions 731-758 at the C-terminal end of human ASPH represented by SEQ ID NO: 1, with the Threonine at relative position 19, corresponding to position 748 of human ASPH, phosphorylated, as
CASSFRLIFIVDVWHPEL-T($PO_3H_2$)-PQQRRSLPAI represented by SEQ ID NO: 19; and
(b) a peptide comprising 29 amino acids with Cysteine at its amino terminus, plus 28 amino acids corresponding to positions 731-758 at the C-terminal end of human ASPH represented by SEQ ID NO: 1, as
CASSFRLIFIVDVWHPELTPQQRRSLPAI, represented by SEQ ID NO: 20.

3. The method of claim 1, wherein said antibody comprising a recombinant heavy chain and a recombinant light chain, or a fragment thereof, which binds to one or more peptide epitopes of human aspartyl (asparaginyl) β-hydroxylase (ASPH), wherein at least one of said peptide epitopes is located within or adjacent to a position in the catalytic domain of ASPH that is within 30 amino acids of the C-terminus of human ASPH, corresponding to the sequence
QDASSFRLIFIVDVWHPELTPQQRRSLPAI represented by positions 729-758 of SEQ ID NO: 1;
wherein said antibody binds to an epitope comprising at least 4 consecutive amino acid residues located within 30 amino acids from the C-terminal end of human ASPH represented by SEQ ID NO: 1;
wherein said epitope comprising at least 4 consecutive amino acid residues located within 30 amino acids from the C-terminal end of human ASPH comprises the consecutive amino acid residues selected from the group consisting of
PELT represented by SEQ ID NO: 42,
ELTP represented by SEQ ID NO: 43,
LTPQ represented by SEQ ID NO: 44,
TPQQ represented by SEQ ID NO: 45,
PQQR represented by SEQ ID NO: 46,
QQRR represented by SEQ ID NO: 47,
QRRS represented by SEQ ID NO: 48,
RRSL represented by SEQ ID NO: 49,
RSLP represented by SEQ ID NO: 50,
SLPA represented by SEQ ID NO: 51, and
LPAI represented by SEQ ID NO: 52.

4. The method of claim 3, wherein said peptide epitope comprises a phosphorylated threonine, $T(PO_3H_2)$
at relative amino acid position 4 of PELT represented by SEQ ID NO: 42;
at relative amino acid position 3 of ELTP represented by SEQ ID NO: 43;
at relative amino acid position 2 of LTPQ represented by SEQ ID NO: 44; and
at relative amino acid position 1 of TPQQ represented by SEQ ID NO: 45.

5. A method of treating cancer in a mammalian subject comprising administering to a subject in need thereof a composition comprising a monoclonal antibody comprising a recombinant heavy chain and a recombinant light chain, or a fragment thereof, which binds to one or more peptide epitopes of human aspartyl (asparaginyl) β-hydroxylase (ASPH), wherein at least one of said peptide epitopes is located within or adjacent to a position in the catalytic domain of ASPH that is within 30 amino acids of the C-terminus of human ASPH, corresponding to the sequence
QDASSFRLIFIVDVWHPELTPQQRRSLPAI represented by positions 729-758 of SEQ ID NO: 1;
wherein said antibody binds to an epitope comprising at least 4 consecutive amino acid residues located within 30 amino acids from the C-terminal end of human ASPH represented by SEQ ID NO: 1;
wherein said antibody comprises a recombinant heavy chain and a recombinant light chain,
wherein said recombinant heavy chain comprises
a polypeptide sequence selected from the group consisting of SEQ ID NOS 21-25; and
wherein said recombinant light chain comprises
a polypeptide sequence selected from the group consisting of SEQ ID NOS 26-30.

6. The method of claim 5, wherein said antibody is selected from the group consisting of 5H4/5K3 and 9H2/9K1,
wherein antibody 5H4/5K3 comprises
a heavy chain designated 5H4, represented by the sequence SEQ ID NO: 25, and
a light chain 5K3, represented by the sequence SEQ ID NO: 27; and
wherein antibody 9H2/9K1 comprises
a heavy chain designated 9H2, represented by the sequence SEQ ID NO: 29, and
a light chain 9K1 represented by the sequence SEQ ID NO: 30.

7. The method of claim 1, wherein said mammalian subject is a selected from the group consisting of a human, non-human primate, canine, feline, bovine, equine, and a porcine subject.

8. The method of claim 2, wherein said mammalian subject is a human subject.

9. The method of claim 1, wherein said cancer is selected from the group consisting of cancers of the liver, hepatocellular carcinoma and cholangiocarcinoma, pancreatic cancer, gastric cancer, colon cancer, kidney cancer, non-small cell lung cancer, breast cancer, ovarian cancer, cervical cancer, head-and-neck cancers secondary to human papilloma virus infection, prostate cancer, brain cancer, glioblastoma multiform, neuroblastoma, retinoblastoma, and medulloblastoma, and osteosarcoma.

10. The method of claim 1, wherein said antibody or fragment or variant thereof is humanized and comprises one or more complementarity determining regions (CDRs) derived from a non-human source, and one or more portions of the constant regions of a human antibody.

11. The method of claim 1, wherein said antibody or fragment or variant thereof is bispecific and comprises one or more complementarity determining regions (CDRs) derived from a non-human source targeting one or more peptide epitopes located within or adjacent to the catalytic domain of ASPH, and an antibody targeting other epitopes selected from the group consisting of
- the T-cell redirector class, comprising an antibody targeting one or more ASPH CDRs and an antibody targeting CD3;
- the NK-cell redirector class, comprising an antibody targeting one or more ASPH CDRs and an antibody targeting CD16A;
- the tumor targeting immunomodular class, comprising an antibody targeting one or more ASPH CDRs and an antibody targeting CD40 or 4-1BB; and
- the dual immunomodular class, comprising an antibody targeting one or more ASPH CDRs and an antibody targeting PD-L1, PD-1, CTLA-4, TGF-β, LAG-3, TIM-3, or OX40.

12. A method of inhibiting the proliferation of tumor cell or tissue samples grown in culture, comprising administering to the locus of the tumor cells a composition comprising an antibody or fragment or variant thereof which binds to one or more peptide epitopes of human aspartyl (asparaginyl) β-hydroxylase (ASPH) in an amount sufficient to inhibit proliferation, wherein said antibody comprises
- a recombinant heavy chain and a recombinant light chain, each heavy and each light chain comprising 3 complementarity-determining regions (CDRs), or fragment or variant thereof, which binds to one or more peptide epitopes of human aspartyl (asparaginyl) β-hydroxylase (ASPH), wherein at least one of said peptide epitopes comprises at least 4 consecutive amino acid residues located within or adjacent to a position in the catalytic domain of ASPH that is within 30 amino acids of the C-terminus of human ASPH, corresponding to the sequence
  QDASSFRLIFIVDVWHPELTPQQRRSLPAI represented by positions 729-758 of SEQ ID NO: 1;
wherein said antibody or fragment or variant thereof contains one or more conservative amino acid substitutions in which the functional activity relating to binding of the antibody or fragment thereof to an epitope of ASPH is retained;
wherein said antibody comprises a recombinant heavy chain comprising
- a CDR1 comprising a sequence selected from the group consisting of
  NFMC represented by SEQ ID NO: 31, and
  NAMC represented by SEQ ID NO: 32;
- a CDR2 comprising a sequence selected from the group consisting of
  CIYF represented by SEQ ID NO: 33, and
  CIDN represented by SEQ ID NO: 34; and
- a CDR3 comprising a sequence selected from the group consisting of
  DGPGSISWKI represented by SEQ ID NO: 35, and
  NFNI represented by SEQ ID NO: 36;
wherein said antibody comprises a recombinant light chain comprising
- a CDR1 comprising a sequence selected from the group consisting of
  SVYSKNR represented by SEQ ID NO: 37, and
  SVYDNNR represented by SEQ ID NO: 38;
- a CDR2 comprising the sequence
  LAS represented by SEQ ID NO: 39; and
- a CDR3 comprising a sequence selected from the group consisting of
  QGTYDSSGWYWA represented by SEQ ID NO: 40, and
  LGSYSGYIYI represented by SEQ ID NO: 41.

13. The method of claim 12, comprising inhibiting the proliferation of isolated tumor cells in tissue samples grown in culture.

* * * * *

SEQUENCE LISTING

```
<160> NUMBER OF SEQ ID NOS: 52

<210> SEQ ID NO 1
<211> LENGTH: 758
<212> TYPE: PRT
<213> ORGANISM: Homo sapiens
```

```
<220> FEATURE:
<221> NAME/KEY: PEPTIDE
<222> LOCATION: (1)..(758)
<223> OTHER INFORMATION: Polypeptide corresponding to Human ASPH
      deposited as Accession No Q12797, starting at the N-terminus with
      MAQRKNAKSS and ending at the C-terminus with PQQRRSLPAI.

<400> SEQUENCE: 1

Met Ala Gln Arg Lys Asn Ala Lys Ser Ser Gly Asn Ser Ser Ser Ser
1               5                   10                  15

Gly Ser Gly Ser Gly Ser Thr Ser Ala Gly Ser Ser Pro Gly Ala
            20                  25                  30

Arg Arg Glu Thr Lys His Gly His Lys Asn Gly Arg Lys Gly Gly
            35                  40                  45

Leu Ser Gly Thr Ser Phe Phe Thr Trp Phe Met Val Ile Ala Leu Leu
        50                  55                  60

Gly Val Trp Thr Ser Val Ala Val Val Trp Phe Asp Leu Val Asp Tyr
65                  70                  75                  80

Glu Glu Val Leu Gly Lys Leu Gly Ile Tyr Asp Ala Asp Gly Asp Gly
                85                  90                  95

Asp Phe Asp Val Asp Asp Ala Lys Val Leu Leu Gly Leu Lys Glu Arg
            100                 105                 110

Ser Thr Ser Glu Pro Ala Val Pro Glu Glu Ala Glu Pro His Thr
            115                 120                 125

Glu Pro Glu Glu Gln Val Pro Val Glu Ala Glu Pro Gln Asn Ile Glu
            130                 135                 140

Asp Glu Ala Lys Glu Gln Ile Gln Ser Leu Leu His Glu Met Val His
145                 150                 155                 160

Ala Glu His Val Glu Gly Glu Asp Leu Gln Gln Glu Asp Gly Pro Thr
                165                 170                 175

Gly Glu Pro Gln Gln Glu Asp Asp Glu Phe Leu Met Ala Thr Asp Val
            180                 185                 190

Asp Asp Arg Phe Glu Thr Leu Glu Pro Glu Val Ser His Glu Glu Thr
            195                 200                 205

Glu His Ser Tyr His Val Glu Glu Thr Val Ser Gln Asp Cys Asn Gln
        210                 215                 220

Asp Met Glu Glu Met Met Ser Glu Gln Glu Asn Pro Asp Ser Ser Glu
225                 230                 235                 240

Pro Val Val Glu Asp Glu Arg Leu His His Asp Thr Asp Asp Val Thr
                245                 250                 255

Tyr Gln Val Tyr Glu Glu Gln Ala Val Tyr Glu Pro Leu Glu Asn Glu
            260                 265                 270

Gly Ile Glu Ile Thr Glu Val Thr Ala Pro Pro Glu Asp Asn Pro Val
            275                 280                 285

Glu Asp Ser Gln Val Ile Val Glu Glu Val Ser Ile Phe Pro Val Glu
            290                 295                 300

Glu Gln Gln Glu Val Pro Pro Asp Thr Asn Arg Lys Thr Asp Asp Pro
305                 310                 315                 320

Glu Gln Lys Ala Lys Val Lys Lys Lys Pro Lys Leu Leu Asn Lys
                325                 330                 335

Phe Asp Lys Thr Ile Lys Ala Glu Leu Asp Ala Ala Glu Lys Leu Arg
            340                 345                 350

Lys Arg Gly Lys Ile Glu Glu Ala Val Asn Ala Phe Lys Glu Leu Val
            355                 360                 365

Arg Lys Tyr Pro Gln Ser Pro Arg Ala Arg Tyr Gly Lys Ala Gln Cys
```

```
            370                 375                 380
Glu Asp Asp Leu Ala Glu Lys Arg Arg Ser Asn Glu Val Leu Arg Gly
385                 390                 395                 400

Ala Ile Glu Thr Tyr Gln Glu Val Ala Ser Leu Pro Asp Val Pro Ala
                405                 410                 415

Asp Leu Leu Lys Leu Ser Leu Lys Arg Ser Asp Arg Gln Gln Phe
            420                 425                 430

Leu Gly His Met Arg Gly Ser Leu Leu Thr Leu Gln Arg Leu Val Gln
                435                 440                 445

Leu Phe Pro Asn Asp Thr Ser Leu Lys Asn Asp Leu Gly Val Gly Tyr
450                 455                 460

Leu Leu Ile Gly Asp Asn Asp Asn Ala Lys Lys Val Tyr Glu Glu Val
465                 470                 475                 480

Leu Ser Val Thr Pro Asn Asp Gly Phe Ala Lys Val His Tyr Gly Phe
                485                 490                 495

Ile Leu Lys Ala Gln Asn Lys Ile Ala Glu Ser Ile Pro Tyr Leu Lys
                500                 505                 510

Glu Gly Ile Glu Ser Gly Asp Pro Gly Thr Asp Asp Gly Arg Phe Tyr
                515                 520                 525

Phe His Leu Gly Asp Ala Met Gln Arg Val Gly Asn Lys Glu Ala Tyr
530                 535                 540

Lys Trp Tyr Glu Leu Gly His Lys Arg Gly His Phe Ala Ser Val Trp
545                 550                 555                 560

Gln Arg Ser Leu Tyr Asn Val Asn Gly Leu Lys Ala Gln Pro Trp Trp
                565                 570                 575

Thr Pro Lys Glu Thr Gly Tyr Thr Glu Leu Val Lys Ser Leu Glu Arg
                580                 585                 590

Asn Trp Lys Leu Ile Arg Asp Glu Gly Leu Ala Val Met Asp Lys Ala
                595                 600                 605

Lys Gly Leu Phe Leu Pro Glu Asp Glu Asn Leu Arg Glu Lys Gly Asp
610                 615                 620

Trp Ser Gln Phe Thr Leu Trp Gln Gln Gly Arg Arg Asn Glu Asn Ala
625                 630                 635                 640

Cys Lys Gly Ala Pro Lys Thr Cys Thr Leu Leu Glu Lys Phe Pro Glu
                645                 650                 655

Thr Thr Gly Cys Arg Arg Gly Gln Ile Lys Tyr Ser Ile Met His Pro
                660                 665                 670

Gly Thr His Val Trp Pro His Thr Gly Pro Thr Asn Cys Arg Leu Arg
                675                 680                 685

Met His Leu Gly Leu Val Ile Pro Lys Glu Gly Cys Lys Ile Arg Cys
690                 695                 700

Ala Asn Glu Thr Lys Thr Trp Glu Glu Gly Lys Val Leu Ile Phe Asp
705                 710                 715                 720

Asp Ser Phe Glu His Glu Val Trp Gln Asp Ala Ser Ser Phe Arg Leu
                725                 730                 735

Ile Phe Ile Val Asp Val Trp His Pro Glu Leu Thr Pro Gln Gln Arg
                740                 745                 750

Arg Ser Leu Pro Ala Ile
            755

<210> SEQ ID NO 2
<211> LENGTH: 794
<212> TYPE: PRT
<213> ORGANISM: Canis lupus
```

```
<220> FEATURE:
<221> NAME/KEY: PEPTIDE
<222> LOCATION: (1)..(794)
<223> OTHER INFORMATION: Canine ASPH corresponding to GenBank ACCESSION
      XP_022267901 - aspartyl/asparaginyl beta-hydroxylase isoform X1
      [Canis lupus familiaris]

<400> SEQUENCE: 2
```

Met Ala Glu Glu Thr Lys His Gly Gly His Lys Asn Gly Arg Lys Gly
1               5                   10                  15

Gly Leu Ser Gly Ser Ser Phe Phe Thr Trp Phe Met Val Ile Ala Leu
            20                  25                  30

Leu Gly Val Trp Thr Ser Val Ala Val Val Trp Phe Asp Leu Val Asp
        35                  40                  45

Tyr Glu Glu Val Leu Ala Lys Ala Lys Asp Phe Arg Tyr Asn Leu Ser
50                  55                  60

Glu Val Leu Gln Gly Lys Leu Gly Val Tyr Asp Ala Asp Gly Asp Gly
65                  70                  75                  80

Asp Phe Asp Val Asp Ala Lys Val Leu Leu Gly Leu Thr Lys Asp
            85                  90                  95

Gly Ser Asn Glu Asn Ile Asp Ser Leu Glu Glu Val Leu Asn Ile Leu
            100                 105                 110

Ala Glu Glu Ser Ser Asp Trp Phe Tyr Gly Phe Leu Ser Phe Leu Tyr
            115                 120                 125

Asp Ile Met Thr Pro Phe Glu Met Leu Glu Glu Glu Glu Glu Ser
            130                 135                 140

Glu Thr Ala Asp Gly Val Asp Gly Leu Lys Glu Arg Ser Ala Ser Lys
145                 150                 155                 160

Pro Thr Val Pro Pro Glu Glu Ala Glu Pro Tyr Pro Trp Leu Glu Glu
            165                 170                 175

Gln Val Ile Glu Asp Ser Gly Pro Gln Asn Thr Glu Asp Glu Val Gln
            180                 185                 190

Glu Val Gln Ile Glu Ser Leu Leu His Glu Ala Val Tyr Thr Glu His
            195                 200                 205

Gly Asp Asp Val Gln Gln Glu Glu Asp Gly Gln Val Arg Glu Pro Gln
            210                 215                 220

Pro Glu Asp Asp Phe Leu Val Gly Ser Asp Thr Asp Asp Arg Tyr Glu
225                 230                 235                 240

Pro Leu Glu Thr Gly Thr Phe His Glu Glu Thr Glu Asp Ser Tyr His
            245                 250                 255

Ile Glu Glu Thr Ala Ser Gln Ala Tyr Asn Gln Asp Met Glu Glu Met
            260                 265                 270

Met Tyr Glu Gln Asp Asn Pro Asp Ser Met Glu Pro Ile Val Gly Asp
            275                 280                 285

Asp Ala Arg Thr Tyr His Glu Ala Asp Leu Thr Tyr Gln Asp Tyr
            290                 295                 300

Asp Glu Pro Val Tyr Glu Pro Pro Glu Asn Glu Gly Leu Glu Ser Ser
305                 310                 315                 320

Asp Asn Ala Gly Glu Asp Ser Asn Ile Ile Leu Glu Glu Val Tyr Met
            325                 330                 335

Pro Pro Ala Glu Glu Gln Glu Val Pro Pro Glu Thr Asn Arg Lys
            340                 345                 350

Thr Asp Asp Pro Glu Ile Lys Glu Lys Val Lys Lys Lys Pro Lys
            355                 360                 365

Leu Leu Asn Lys Phe Asp Lys Thr Ile Lys Ala Glu Leu Asp Ala Ala

```
            370                 375                 380
Glu Lys Leu Arg Lys Arg Gly Lys Ile Glu Glu Ala Leu Ser Ala Phe
385                 390                 395                 400

Gln Glu Leu Val Arg Lys Tyr Pro Gln Ser Pro Arg Ala Arg Tyr Gly
                405                 410                 415

Lys Ala Gln Cys Glu Asp Asp Leu Ala Glu Lys Arg Arg Ser Asn Glu
                420                 425                 430

Val Leu Arg Gly Ala Ile Glu Thr Tyr Gln Glu Val Ala Ser Leu Pro
            435                 440                 445

Asn Val Pro Thr Asp Leu Leu Lys Leu Thr Leu Lys Arg Arg Ser Asp
450                 455                 460

Arg Gln Gln Phe Leu Gly His Met Arg Gly Ser Leu Ile Thr Leu Gln
465                 470                 475                 480

Lys Leu Val Gln Leu Phe Pro Asp Asp Met Ser Leu Lys Asn Asp Leu
                485                 490                 495

Gly Val Gly Tyr Leu Leu Ile Gly Asp Asn Asn Ala Gln Lys Val
                500                 505                 510

Tyr Glu Glu Val Leu Asn Val Thr Pro Asn Asp Gly Phe Ala Lys Val
            515                 520                 525

His Tyr Gly Phe Ile Leu Lys Ala Gln Asn Lys Ile Ala Glu Ser Ile
            530                 535                 540

Pro Tyr Leu Lys Glu Gly Ile Glu Ser Gly Asp Pro Gly Thr Asp Asp
545                 550                 555                 560

Gly Arg Phe Tyr Phe His Leu Gly Asp Ala Met Gln Arg Val Gly Asn
                565                 570                 575

Lys Glu Ala Tyr Lys Trp Tyr Glu Leu Gly His Lys Arg Gly His Phe
                580                 585                 590

Ala Ser Val Trp Gln Arg Ser Leu Tyr Asn Val His Gly Leu Lys Ala
            595                 600                 605

Gln Pro Trp Trp Thr Pro Lys Glu Thr Gly Tyr Thr Glu Leu Val Lys
610                 615                 620

Ser Leu Glu Arg Asn Trp Lys Leu Ile Arg Asp Glu Gly Leu Ala Val
625                 630                 635                 640

Met Asp Lys Ala Lys Gly Leu Phe Leu Pro Glu Asp Glu Asn Leu Arg
                645                 650                 655

Glu Lys Gly Asp Trp Ser Gln Phe Thr Leu Trp Gln Gln Gly Arg Lys
                660                 665                 670

Asn Glu Asn Ala Cys Lys Gly Ala Pro Lys Thr Cys Ser Leu Leu Asp
            675                 680                 685

Lys Phe Pro Glu Thr Thr Gly Cys Arg Arg Gly Gln Ile Lys Tyr Ser
690                 695                 700

Ile Met His Pro Gly Thr His Val Trp Pro Thr Gly Pro Thr Asn
705                 710                 715                 720

Cys Arg Leu Arg Met His Leu Gly Leu Val Ile Pro Lys Glu Gly Cys
                725                 730                 735

Lys Ile Arg Cys Ala Asn Glu Thr Lys Thr Trp Glu Gly Lys Val
                740                 745                 750

Leu Ile Phe Asp Asp Ser Phe Glu His Glu Val Trp Gln Asp Ala Thr
            755                 760                 765

Ser Phe Arg Leu Ile Phe Ile Val Asp Val Trp His Pro Glu Leu Thr
            770                 775                 780

Pro Gln Gln Arg His Ser Leu Pro Ala Ile
785                 790
```

<210> SEQ ID NO 3
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: KRRSNEVLR corresponding to residues 391-399 of ASPH

<400> SEQUENCE: 3

Lys Arg Arg Ser Asn Glu Val Leu Arg
1               5

<210> SEQ ID NO 4
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: DRQQFLGHM corresponding to residues 428-436 of ASPH

<400> SEQUENCE: 4

Asp Arg Gln Gln Phe Leu Gly His Met
1               5

<210> SEQ ID NO 5
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: GYLLIGDNDN corresponding to residues 463-470 of ASPH

<400> SEQUENCE: 5

Gly Tyr Leu Leu Ile Gly Asp Asn Asp Asn
1               5                   10

<210> SEQ ID NO 6
<211> LENGTH: 8
<212> TYPE: PRT
<213> ORGANISM: Homo sapiens
<220> FEATURE:
<221> NAME/KEY: PEPTIDE
<222> LOCATION: (1)..(8)
<223> OTHER INFORMATION: RSLYNVNG corresponding to residues 562-569 of ASPH

<400> SEQUENCE: 6

Arg Ser Leu Tyr Asn Val Asn Gly
1               5

<210> SEQ ID NO 7
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: PQQRRSLPAI corresponding to residues 749-758 of ASPH

<400> SEQUENCE: 7

Pro Gln Gln Arg Arg Ser Leu Pro Ala Ile

<210> SEQ ID NO 8
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: FLPEDENLRE corresponding to residues 612-621 of
      human ASPH

<400> SEQUENCE: 8

Phe Leu Pro Glu Asp Glu Asn Leu Arg Glu
1               5                   10

<210> SEQ ID NO 9
<211> LENGTH: 10
<212> TYPE: PRT
<213> ORGANISM: Homo sapiens
<220> FEATURE:
<221> NAME/KEY: PEPTIDE
<222> LOCATION: (1)..(10)
<223> OTHER INFORMATION: VWPHTGPTNC corresponding to residues 676-685 of
      human ASPH

<400> SEQUENCE: 9

Val Trp Pro His Thr Gly Pro Thr Asn Cys
1               5                   10

<210> SEQ ID NO 10
<211> LENGTH: 9
<212> TYPE: PRT
<213> ORGANISM: Homo sapiens
<220> FEATURE:
<221> NAME/KEY: PEPTIDE
<222> LOCATION: (1)..(9)
<223> OTHER INFORMATION: LWQQGRRNE corresponding to residues 630-638 of
      human ASPH

<400> SEQUENCE: 10

Leu Trp Gln Gln Gly Arg Arg Asn Glu
1               5

<210> SEQ ID NO 11
<211> LENGTH: 9
<212> TYPE: PRT
<213> ORGANISM: Canis lupus
<220> FEATURE:
<221> NAME/KEY: PEPTIDE
<222> LOCATION: (1)..(9)
<223> OTHER INFORMATION: Peptide #C1, KRRSNEVLR, corresponding to
      residues 427-435 of canine ASPH

<400> SEQUENCE: 11

Lys Arg Arg Ser Asn Glu Val Leu Arg
1               5

<210> SEQ ID NO 12
<211> LENGTH: 9
<212> TYPE: PRT
<213> ORGANISM: Canis lupus
<220> FEATURE:
<221> NAME/KEY: PEPTIDE
<222> LOCATION: (1)..(9)
<223> OTHER INFORMATION: Peptide #C2, DRQQFLGHM, corresponding to
      residues 464-472 of canine ASPH

<400> SEQUENCE: 12

```
Asp Arg Gln Gln Phe Leu Gly His Met
1               5

<210> SEQ ID NO 13
<211> LENGTH: 10
<212> TYPE: PRT
<213> ORGANISM: Canis lupus
<220> FEATURE:
<221> NAME/KEY: PEPTIDE
<222> LOCATION: (1)..(10)
<223> OTHER INFORMATION: Peptide #C3, GYLLIGDNNN, corresponding to
      residues 499-508 of canine ASPH

<400> SEQUENCE: 13

Gly Tyr Leu Leu Ile Gly Asp Asn Asn Asn
1               5                   10

<210> SEQ ID NO 14
<211> LENGTH: 8
<212> TYPE: PRT
<213> ORGANISM: Canis lupus
<220> FEATURE:
<221> NAME/KEY: PEPTIDE
<222> LOCATION: (1)..(8)
<223> OTHER INFORMATION: Peptide #C4, RSLYNVHG, corresponding to
      residues 598-605 of canine ASPH

<400> SEQUENCE: 14

Arg Ser Leu Tyr Asn Val His Gly
1               5

<210> SEQ ID NO 15
<211> LENGTH: 10
<212> TYPE: PRT
<213> ORGANISM: Canis lupus
<220> FEATURE:
<221> NAME/KEY: PEPTIDE
<222> LOCATION: (1)..(10)
<223> OTHER INFORMATION: Peptide #C5, PQQRHSLPA,I corresponding to
      residues 785-794 of canine ASPH

<400> SEQUENCE: 15

Pro Gln Gln Arg His Ser Leu Pro Ala Ile
1               5                   10

<210> SEQ ID NO 16
<211> LENGTH: 10
<212> TYPE: PRT
<213> ORGANISM: Canis lupus
<220> FEATURE:
<221> NAME/KEY: PEPTIDE
<222> LOCATION: (1)..(10)
<223> OTHER INFORMATION: FLPEDENLRE corresponding to residues 648-657 of
      canine ASPH

<400> SEQUENCE: 16

Phe Leu Pro Glu Asp Glu Asn Leu Arg Glu
1               5                   10

<210> SEQ ID NO 17
<211> LENGTH: 10
<212> TYPE: PRT
<213> ORGANISM: Canis lupus
<220> FEATURE:
<221> NAME/KEY: PEPTIDE
<222> LOCATION: (1)..(10)
<223> OTHER INFORMATION: VWPHTGPTNC corresponding to residues 712-721 of
      canine ASPH

<400> SEQUENCE: 17
```

```
Val Trp Pro His Thr Gly Pro Thr Asn Cys
1               5                   10

<210> SEQ ID NO 18
<211> LENGTH: 9
<212> TYPE: PRT
<213> ORGANISM: Canis lupus
<220> FEATURE:
<221> NAME/KEY: PEPTIDE
<222> LOCATION: (1)..(9)
<223> OTHER INFORMATION: LWQQGRKNE corresponding to residues 666-674 of
      canine ASPH

<400> SEQUENCE: 18

Leu Trp Gln Gln Gly Arg Lys Asn Glu
1               5

<210> SEQ ID NO 19
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(29)
<223> OTHER INFORMATION: Synthetic peptide comprising 29 amino acids
      with Cysteine at its amino terminus, plus 28 amino acids
      corresponding to positions 731-758 at the C-terminal end of human
      ASPH, with the Threonine at 19 (corresponding to 748 of ASPH)
      phosphorylated.
<220> FEATURE:
<221> NAME/KEY: PHOSPHORYLATION
<222> LOCATION: (19)..(19)
<223> OTHER INFORMATION: Synthetic peptide comprising 29 amino acids
      with Cysteine at its amino terminus, plus 28 amino acids
      corresponding to positions 731-758 at the C-terminal end of human
      ASPH, with the Threonine at 19 (corresponding to 748 of ASPH)
      phosphorylated.

<400> SEQUENCE: 19

Cys Ala Ser Ser Phe Arg Leu Ile Phe Ile Val Asp Val Trp His Pro
1               5                   10                  15

Glu Leu Thr Pro Gln Gln Arg Arg Ser Leu Pro Ala Ile
            20                  25

<210> SEQ ID NO 20
<211> LENGTH: 29
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(29)
<223> OTHER INFORMATION: Synthetic peptide comprising 29 amino acids
      with Cysteine at its amino terminus, plus 28 amino acids
      corresponding to positions 731-758 at the C-terminal end of human
      ASPH.

<400> SEQUENCE: 20

Cys Ala Ser Ser Phe Arg Leu Ile Phe Ile Val Asp Val Trp His Pro
1               5                   10                  15

Glu Leu Thr Pro Gln Gln Arg Arg Ser Leu Pro Ala Ile
            20                  25

<210> SEQ ID NO 21
<211> LENGTH: 150
<212> TYPE: PRT
```

```
<213> ORGANISM: Oryctolagus cuniculus
<220> FEATURE:
<221> NAME/KEY: PEPTIDE
<222> LOCATION: (1)..(150)
<223> OTHER INFORMATION: Translated variable region of Clone ID #1H2
      comprising a GQPK sequence at the start of the constant region for
      a heavy chain sequence

<400> SEQUENCE: 21

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Asp Leu Val Lys Pro
            20                  25                  30

Gly Ala Ser Leu Thr Leu Thr Cys Thr Ala Ser Gly Leu Ser Phe Ser
        35                  40                  45

Asp Asn Phe Met Cys Trp Val Arg Gln Ala Pro Gly Lys Gly Leu Glu
    50                  55                  60

Trp Ile Ala Cys Ile Tyr Phe Asp Ser Gly Ile Thr Tyr Tyr Ala
65                  70                  75                  80

Ser Trp Ala Lys Gly Arg Phe Thr Ile Ser Lys Thr Ser Ser Pro Thr
                85                  90                  95

Val Thr Leu Gln Met Thr Ser Leu Thr Ala Ala Asp Thr Ala Thr Tyr
            100                 105                 110

Phe Cys Ala Arg Asp Gly Pro Gly Ser Ile Ser Trp Asp Leu Trp Gly
        115                 120                 125

Gln Gly Thr Leu Val Thr Val Ser Ser Gly Gln Pro Lys Ala Pro Ser
    130                 135                 140

Val Phe Pro Leu Ala Pro
145                 150

<210> SEQ ID NO 22
<211> LENGTH: 148
<212> TYPE: PRT
<213> ORGANISM: Oryctolagus cuniculus
<220> FEATURE:
<221> NAME/KEY: PEPTIDE
<222> LOCATION: (1)..(148)
<223> OTHER INFORMATION: Translated variable region of Clone ID #1K6
      comprising a GDPV sequence at the start of the constant region for
      a kappa sequence

<400> SEQUENCE: 22

Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Pro Ser Pro
            20                  25                  30

Val Ser Ala Ala Val Gly Gly Thr Val Thr Ile Ser Cys Gln Ser Ser
        35                  40                  45

Lys Ser Val Tyr Ser Lys Asn Arg Leu Ala Trp Tyr Gln Gln Lys Pro
    50                  55                  60

Gly Gln Pro Pro Lys Leu Leu Ile Tyr Glu Ala Ser Lys Leu Ala Ser
65                  70                  75                  80

Gly Val Pro Ser Arg Phe Lys Gly Ser Gly Ser Gly Thr Gln Phe Thr
                85                  90                  95

Leu Thr Ile Ser Gly Val Gln Cys Asp Asp Ala Ala Thr Tyr Tyr Cys
            100                 105                 110

Gln Gly Thr Tyr Asp Ser Ser Gly Trp Tyr Trp Ala Phe Gly Gly Gly
        115                 120                 125

Thr Glu Val Val Val Lys Gly Asp Pro Val Ala Pro Thr Val Leu Ile
```

Phe Pro Pro Ala
145

<210> SEQ ID NO 23
<211> LENGTH: 142
<212> TYPE: PRT
<213> ORGANISM: Oryctolagus cuniculus
<220> FEATURE:
<221> NAME/KEY: PEPTIDE
<222> LOCATION: (1)..(142)
<223> OTHER INFORMATION: Translated variable region of Clone ID #5H1

<400> SEQUENCE: 23

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Asp Leu Val Lys Pro
                20                  25                  30

Gly Ala Ser Leu Thr Leu Thr Cys Lys Ala Ser Gly Phe Asp Phe Ser
            35                  40                  45

Ser Asn Ala Met Cys Trp Val Arg Gln Ala Pro Gly Lys Gly Pro Glu
        50                  55                  60

Trp Ile Ala Cys Ile Asp Asn Gly Asp Gly Ser Thr Asp Tyr Ala Thr
65                  70                  75                  80

Trp Ala Lys Gly Arg Phe Thr Ile Ser Lys Thr Ser Ser Thr Thr Val
                85                  90                  95

Thr Leu Gln Met Thr Ser Leu Thr Ala Ala Asp Thr Ala Thr Tyr Phe
                100                 105                 110

Cys Thr Arg Asn Phe Asn Leu Trp Gly Pro Gly His Pro Gly His Arg
            115                 120                 125

Leu Glu Arg Thr Ala Glu Ser Pro Val Gly Val Ser Thr Gly
        130                 135                 140

<210> SEQ ID NO 24
<211> LENGTH: 143
<212> TYPE: PRT
<213> ORGANISM: Oryctolagus cuniculus
<220> FEATURE:
<221> NAME/KEY: PEPTIDE
<222> LOCATION: (1)..(143)
<223> OTHER INFORMATION: Translated variable region of Clone ID #5H3
      comprising a GQPK sequence at the start of the constant region for
      a heavy chain sequence

<400> SEQUENCE: 24

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Asp Leu Val Lys Pro
                20                  25                  30

Gly Ala Ser Leu Thr Leu Thr Cys Lys Ala Ser Gly Phe Asp Phe Ser
            35                  40                  45

Ser Asn Ala Met Cys Trp Val Arg Gln Ala Pro Gly Lys Gly Pro Glu
        50                  55                  60

Trp Ile Ala Cys Ile Asp Asn Gly Asp Gly Ser Thr Asp Tyr Ala Thr
65                  70                  75                  80

Trp Ala Lys Gly Arg Phe Thr Ile Ser Lys Thr Ser Ser Thr Thr Val
                85                  90                  95

Thr Leu Gln Met Thr Ser Leu Thr Ala Ala Asp Thr Ala Thr Tyr Phe
                100                 105                 110

```
Cys Thr Arg Asn Phe Asn Leu Trp Gly Gln Gly Thr Leu Val Thr Val
            115                 120                 125

Ser Ser Gly Gln Pro Lys Ala Pro Ser Val Phe Pro Leu Ala Pro
        130                 135                 140
```

<210> SEQ ID NO 25
<211> LENGTH: 143
<212> TYPE: PRT
<213> ORGANISM: Oryctolagus cuniculus
<220> FEATURE:
<221> NAME/KEY: PEPTIDE
<222> LOCATION: (1)..(143)
<223> OTHER INFORMATION: Translated variable region of Clone ID #5H4 comprising a GQPK sequence at the start of the constant region for a heavy chain sequence

<400> SEQUENCE: 25

```
Met Glu Thr Gly Leu Arg Trp Leu Leu Leu Val Ala Val Leu Lys Gly
1               5                   10                  15

Val Gln Cys Gln Ser Leu Glu Glu Ser Gly Gly Asp Leu Val Lys Pro
            20                  25                  30

Gly Ala Ser Leu Thr Leu Thr Cys Lys Ala Ser Gly Phe Asp Phe Ser
        35                  40                  45

Ser Asn Ala Met Cys Trp Val Arg Gln Ala Pro Gly Lys Gly Pro Glu
    50                  55                  60

Trp Ile Ala Cys Ile Asp Asn Gly Asp Gly Ser Thr Asp Tyr Ala Thr
65                  70                  75                  80

Trp Ala Lys Gly Arg Phe Thr Ile Ser Lys Thr Ser Ser Thr Thr Val
                85                  90                  95

Thr Leu Gln Met Thr Ser Leu Thr Ala Ala Asp Thr Ala Thr Tyr Phe
            100                 105                 110

Cys Thr Arg Asn Phe Asn Leu Trp Gly Gln Gly Thr Leu Val Thr Val
        115                 120                 125

Ser Ser Gly Gln Pro Lys Ala Pro Ser Val Phe Pro Leu Ala Pro
    130                 135                 140
```

<210> SEQ ID NO 26
<211> LENGTH: 146
<212> TYPE: PRT
<213> ORGANISM: Oryctolagus cuniculus
<220> FEATURE:
<221> NAME/KEY: PEPTIDE
<222> LOCATION: (1)..(146)
<223> OTHER INFORMATION: Translated variable region of Clone ID #5K1 comprising a GDPV sequence at the start of the constant region for a kappa sequence

<400> SEQUENCE: 26

```
Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Ala Ser Ser
            20                  25                  30

Val Ser Ala Ala Val Gly Gly Thr Val Thr Ile Ser Cys Gln Ser Ser
        35                  40                  45

Gln Ser Val Tyr Asp Asn Asn Arg Leu Ala Trp Phe Gln Gln Lys Pro
    50                  55                  60

Gly Gln Pro Pro Lys Leu Leu Ile Tyr Glu Thr Ser Lys Leu Ala Ser
65                  70                  75                  80

Gly Val Pro Leu Arg Phe Lys Gly Ser Gly Ser Gly Thr Gln Phe Thr
                85                  90                  95
```

```
Leu Thr Ile Ser Asp Leu Glu Cys Asp Asp Ala Ala Thr Tyr Tyr Cys
            100                 105                 110

Leu Gly Ser Tyr Ser Gly Tyr Ile Tyr Thr Phe Gly Gly Gly Thr Glu
        115                 120                 125

Val Val Val Lys Gly Asp Pro Val Ala Pro Thr Val Leu Ile Phe Pro
    130                 135                 140

Pro Ala
145

<210> SEQ ID NO 27
<211> LENGTH: 146
<212> TYPE: PRT
<213> ORGANISM: Oryctolagus cuniculus
<220> FEATURE:
<221> NAME/KEY: PEPTIDE
<222> LOCATION: (1)..(146)
<223> OTHER INFORMATION: Translated variable region of Clone ID #5K3
      comprising a GDPV sequence at the start of the constant region for
      a kappa sequence

<400> SEQUENCE: 27

Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Ala Ser Ser
            20                  25                  30

Val Ser Ala Ala Val Gly Gly Thr Val Thr Ile Ser Cys Gln Ser Ser
        35                  40                  45

Gln Ser Val Tyr Asp Asn Asn Arg Leu Ala Trp Phe Gln Gln Lys Pro
    50                  55                  60

Gly Gln Pro Pro Lys Leu Leu Ile Tyr Glu Thr Ser Lys Leu Ala Ser
65                  70                  75                  80

Gly Val Pro Leu Arg Phe Lys Gly Ser Gly Ser Gly Thr Gln Phe Thr
                85                  90                  95

Leu Thr Ile Ser Asp Leu Glu Cys Asp Asp Ala Ala Thr Tyr Tyr Cys
            100                 105                 110

Leu Gly Ser Tyr Ser Gly Tyr Ile Tyr Thr Phe Gly Gly Gly Thr Glu
        115                 120                 125

Val Val Val Lys Gly Asp Pro Val Ala Pro Thr Val Leu Ile Phe Pro
    130                 135                 140

Pro Ala
145

<210> SEQ ID NO 28
<211> LENGTH: 146
<212> TYPE: PRT
<213> ORGANISM: Oryctolagus cuniculus
<220> FEATURE:
<221> NAME/KEY: PEPTIDE
<222> LOCATION: (1)..(146)
<223> OTHER INFORMATION: Translated variable region of Clone ID #5K6
      comprising a GDPV sequence at the start of the constant region for
      a kappa sequence

<400> SEQUENCE: 28

Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Ala Ser Ser
            20                  25                  30

Val Ser Ala Ala Val Gly Gly Thr Val Thr Ile Ser Cys Gln Ser Ser
        35                  40                  45
```

Gln Ser Val Tyr Asp Asn Asn Arg Leu Ala Trp Phe Gln Gln Lys Pro
            50                  55                  60

Gly Gln Pro Pro Lys Leu Leu Ile Tyr Glu Thr Ser Lys Leu Ala Ser
 65                  70                  75                  80

Gly Val Pro Leu Arg Phe Lys Gly Ser Gly Ser Gly Thr Gln Phe Thr
                    85                  90                  95

Leu Thr Ile Ser Asp Leu Glu Cys Asp Asp Ala Ala Thr Tyr Tyr Cys
                100                 105                 110

Leu Gly Ser Tyr Ser Gly Tyr Ile Tyr Thr Phe Gly Gly Gly Thr Glu
            115                 120                 125

Val Val Val Lys Gly Asp Pro Val Ala Pro Thr Val Leu Ile Phe Pro
130                 135                 140

Pro Ala
145

<210> SEQ ID NO 29
<211> LENGTH: 142
<212> TYPE: PRT
<213> ORGANISM: Oryctolagus cuniculus
<220> FEATURE:
<221> NAME/KEY: PEPTIDE
<222> LOCATION: (1)..(142)
<223> OTHER INFORMATION: Translated variable region of Clone ID #9H2
      comprising a GQPK sequence at the start of the constant region for
      a heavy chain sequence

<400> SEQUENCE: 29

Met Glu Thr Gly Leu Arg Trp Leu Leu Leu Val Ala Val Leu Lys Gly
 1               5                  10                  15

Val Gln Cys Gln Ser Leu Glu Glu Ser Gly Gly Asp Leu Val Lys Pro
                20                  25                  30

Gly Ala Ser Leu Thr Leu Thr Cys Lys Ala Ser Gly Phe Asp Phe Ile
            35                  40                  45

Ser Asn Ala Met Cys Trp Val Arg Gln Ala Pro Gly Lys Gly Pro Glu
 50                  55                  60

Trp Ile Ala Cys Ile Asp Asn Gly Asp Gly Ser Thr Asp Tyr Ala Thr
 65                  70                  75                  80

Trp Ala Lys Gly Arg Phe Thr Ile Ser Lys Thr Ser Ser Thr Thr Val
                    85                  90                  95

Thr Leu Gln Met Thr Ser Leu Thr Ala Ala Asp Thr Ala Thr Tyr Phe
                100                 105                 110

Cys Thr Arg Asn Phe Asn Leu Trp Gly Gln Gly Thr Leu Thr Val Ser
            115                 120                 125

Ser Gly Gln Pro Lys Ala Pro Ser Val Phe Pro Leu Ala Pro
130                 135                 140

<210> SEQ ID NO 30
<211> LENGTH: 146
<212> TYPE: PRT
<213> ORGANISM: Oryctolagus cuniculus
<220> FEATURE:
<221> NAME/KEY: PEPTIDE
<222> LOCATION: (1)..(146)
<223> OTHER INFORMATION: Translated variable region of Clone ID #9K1
      comprising a GDPV sequence at the start of the constant region for
      a kappa sequence

<400> SEQUENCE: 30

Met Asp Thr Arg Ala Pro Thr Gln Leu Leu Gly Leu Leu Leu Leu Trp
 1               5                  10                  15

```
Leu Pro Gly Ala Thr Phe Ala Gln Val Leu Thr Gln Thr Ala Ser Ser
             20                  25                  30

Val Ser Ala Ala Val Gly Gly Thr Val Thr Ile Ser Cys Gln Ser Ser
         35                  40                  45

Gln Ser Val Tyr Asp Asn Asn Arg Leu Ala Trp Phe Gln Gln Lys Ser
     50                  55                  60

Gly Gln Pro Pro Lys Leu Leu Ile Tyr Glu Thr Ser Lys Leu Ala Ser
65                  70                  75                  80

Gly Val Pro Leu Arg Phe Lys Gly Ser Gly Ser Gly Thr Gln Phe Thr
                 85                  90                  95

Leu Thr Ile Ser Asp Leu Glu Cys Asp Asp Ala Ala Thr Tyr Tyr Cys
            100                 105                 110

Leu Gly Ser Tyr Ser Gly Tyr Ile Tyr Thr Phe Gly Gly Gly Thr Glu
        115                 120                 125

Val Val Val Lys Gly Asp Pro Val Ala Pro Thr Val Leu Ile Phe Pro
    130                 135                 140

Pro Ala
145
```

<210> SEQ ID NO 31
<211> LENGTH: 4
<212> TYPE: PRT
<213> ORGANISM: Artificial Sequence
<220> FEATURE:
<223> OTHER INFORMATION: CDR1 region of clone 1H2 corresponding to
      corresponding to residues 50-53 of SEQ ID NO: 21.
<220> FEATURE:
<221> NAME/KEY: MISC_FEATURE
<222> LOCATION: (1)..(4)
<223> OTHER INFORMATION: CDR1 region of clone 1H2 corresponding to
      corresponding to residues 50-53 of SEQ ID NO: 21.

<400> SEQUENCE: 31

Asn Phe Met Cys
1

<210> SEQ ID NO 32
<211> LENGTH: 4
<212> TYPE: PRT
<213> ORGANISM: Artificial Sequence
<220> FEATURE:
<223> OTHER INFORMATION: CDR1 region of Clones 5H1, 9H2, 5H3, 5H4,
      corresponding to residues 50-53 of SEQ ID NOS: 23, 29, 24, and 25.
<220> FEATURE:
<221> NAME/KEY: MISC_FEATURE
<222> LOCATION: (1)..(4)
<223> OTHER INFORMATION: CDR1 region of Clones 5H1, 9H2, 5H3, 5H4,
      corresponding to residues 50-53 of SEQ ID NOS: 23, 29, 24, and 25.

<400> SEQUENCE: 32

Asn Ala Met Cys
1

<210> SEQ ID NO 33
<211> LENGTH: 4
<212> TYPE: PRT
<213> ORGANISM: Artificial Sequence
<220> FEATURE:
<223> OTHER INFORMATION: The CDR2 regions from the heavy chain clone 1H2
      corresponding to residues 68-71 of SEQ ID NO: 21.
<220> FEATURE:
<221> NAME/KEY: MISC_FEATURE
<222> LOCATION: (1)..(4)
<223> OTHER INFORMATION: The CDR2 regions from the heavy chain clone 1H2
      corresponding to residues 68-71 of SEQ ID NO: 21.

```
<400> SEQUENCE: 33

Cys Ile Tyr Phe
1

<210> SEQ ID NO 34
<211> LENGTH: 4
<212> TYPE: PRT
<213> ORGANISM: Artificial Sequence
<220> FEATURE:
<223> OTHER INFORMATION: The CDR2 regions from the heavy chain clones
      5H1, 9H2, 5H3, 5H4 corresponding to residues 68-71 of SEQ ID NO:
      23, 29, 24, and 25.
<220> FEATURE:
<221> NAME/KEY: MISC_FEATURE
<222> LOCATION: (1)..(4)
<223> OTHER INFORMATION: The CDR2 regions from the heavy chain clones
      5H1, 9H2, 5H3, 5H4 corresponding to residues 68-71 of SEQ ID NO:
      23, 29, 24, and 25.

<400> SEQUENCE: 34

Cys Ile Asp Asn
1

<210> SEQ ID NO 35
<211> LENGTH: 10
<212> TYPE: PRT
<213> ORGANISM: Artificial Sequence
<220> FEATURE:
<223> OTHER INFORMATION: CDR3 regions from the heavy chain clone 1H2
      corresponding to residues 117-126 of SEQ ID NO: 21.
<220> FEATURE:
<221> NAME/KEY: MISC_FEATURE
<222> LOCATION: (1)..(10)
<223> OTHER INFORMATION: CDR3 regions from the heavy chain clone 1H2
      corresponding to residues 117-126 of SEQ ID NO: 21.

<400> SEQUENCE: 35

Asp Gly Pro Gly Ser Ile Ser Trp Asp Ile
1               5                   10

<210> SEQ ID NO 36
<211> LENGTH: 4
<212> TYPE: PRT
<213> ORGANISM: Artificial Sequence
<220> FEATURE:
<223> OTHER INFORMATION: CDR3 regions from the heavy chain clones 5H1,
      9H2, 5H3, 5H4 corresponding to residues 116-119 of SEQ ID NOS: 23,
      29, 24, and 25.
<220> FEATURE:
<221> NAME/KEY: MISC_FEATURE
<222> LOCATION: (1)..(4)
<223> OTHER INFORMATION: CDR3 regions from the heavy chain clones 5H1,
      9H2, 5H3, 5H4 corresponding to residues 116-119 of SEQ ID NOS: 23,
      29, 24, and 25.

<400> SEQUENCE: 36

Asn Phe Asn Ile
1

<210> SEQ ID NO 37
<211> LENGTH: 7
<212> TYPE: PRT
<213> ORGANISM: Artificial Sequence
<220> FEATURE:
<223> OTHER INFORMATION: The CDR1 regions from the kappa chain clone
      1K6, corresponding to residues 50-56 of SEQ ID NO: 22.
<220> FEATURE:
<221> NAME/KEY: MISC_FEATURE
<222> LOCATION: (1)..(7)
<223> OTHER INFORMATION: The CDR1 regions from the kappa chain clone
      1K6, corresponding to residues 50-56 of SEQ ID NO: 22.
```

<400> SEQUENCE: 37

Ser Val Tyr Ser Lys Asn Arg
1               5

<210> SEQ ID NO 38
<211> LENGTH: 7
<212> TYPE: PRT
<213> ORGANISM: Artificial Sequence
<220> FEATURE:
<223> OTHER INFORMATION: The CDR1 regions from the kappa chain clones
      5K1, 5K3, 5K6, and 9K1 corresponding to residues 50-56 of SEQ ID
      NOS: 26, 27, 28, and 30.
<220> FEATURE:
<221> NAME/KEY: MISC_FEATURE
<222> LOCATION: (1)..(7)
<223> OTHER INFORMATION: The CDR1 regions from the kappa chain clones
      5K1, 5K3, 5K6, and 9K1 corresponding to residues 50-56 of SEQ ID
      NOS: 26, 27, 28, and 30.

<400> SEQUENCE: 38

Ser Val Tyr Asp Asn Asn Arg
1               5

<210> SEQ ID NO 39
<211> LENGTH: 3
<212> TYPE: PRT
<213> ORGANISM: Artificial Sequence
<220> FEATURE:
<223> OTHER INFORMATION: The CDR2 regions from the kappa chain clones
      1K6, 5K1, 5K3, 5K6, and 9K1 corresponding to residues 78-80 of SEQ
      ID NOS: 22, 26, 27, 28, and 30.
<220> FEATURE:
<221> NAME/KEY: MISC_FEATURE
<222> LOCATION: (1)..(3)
<223> OTHER INFORMATION: The CDR2 regions from the kappa chain clones
      1K6, 5K1, 5K3, 5K6, and 9K1 corresponding to residues 78-80 of SEQ
      ID NOS: 22, 26, 27, 28, and 30.

<400> SEQUENCE: 39

Leu Ala Ser
1

<210> SEQ ID NO 40
<211> LENGTH: 12
<212> TYPE: PRT
<213> ORGANISM: Artificial Sequence
<220> FEATURE:
<223> OTHER INFORMATION: The CDR3 regions from the kappa chain clone 1K6
      corresponding to residues 113-124 of SEQ ID NO: 22.
<220> FEATURE:
<221> NAME/KEY: MISC_FEATURE
<222> LOCATION: (1)..(12)
<223> OTHER INFORMATION: The CDR3 regions from the kappa chain clone 1K6
      corresponding to residues 113-124 of SEQ ID NO: 22.

<400> SEQUENCE: 40

Gln Gly Thr Tyr Asp Ser Ser Gly Trp Tyr Trp Ala
1               5                   10

<210> SEQ ID NO 41
<211> LENGTH: 10
<212> TYPE: PRT
<213> ORGANISM: Artificial Sequence
<220> FEATURE:
<223> OTHER INFORMATION: The CDR3 regions from the kappa chain clones
      5K1, 5K3, 5K6, and 9K1 corresponding to residues 113-122 of SEQ ID
      NOS: 26, 27, 28, and 30.
<220> FEATURE:
<221> NAME/KEY: MISC_FEATURE
<222> LOCATION: (1)..(10)

```
<223> OTHER INFORMATION: The CDR3 regions from the kappa chain clones
      5K1, 5K3, 5K6, and 9K1 corresponding to residues 113-122 of SEQ ID
      NOS: 26, 27, 28, and 30.

<400> SEQUENCE: 41

Leu Gly Ser Tyr Ser Gly Tyr Ile Tyr Ile
1               5                   10

<210> SEQ ID NO 42
<211> LENGTH: 4
<212> TYPE: PRT
<213> ORGANISM: Artificial Sequence
<220> FEATURE:
<223> OTHER INFORMATION: Four aa peptide corresponding to aa 745-748
      near the carboxy terminus of human ASPH.
<220> FEATURE:
<221> NAME/KEY: MISC_FEATURE
<222> LOCATION: (1)..(4)
<223> OTHER INFORMATION: Four aa peptide corresponding to aa 745-748
      near the carboxy terminus of human ASPH.

<400> SEQUENCE: 42

Pro Glu Leu Thr
1

<210> SEQ ID NO 43
<211> LENGTH: 4
<212> TYPE: PRT
<213> ORGANISM: Artificial Sequence
<220> FEATURE:
<223> OTHER INFORMATION: Four aa peptide corresponding to aa 746-749
      near the carboxy terminus of human ASPH.
<220> FEATURE:
<221> NAME/KEY: MISC_FEATURE
<222> LOCATION: (1)..(4)
<223> OTHER INFORMATION: Four aa peptide corresponding to aa 746-749
      near the carboxy terminus of human ASPH.

<400> SEQUENCE: 43

Glu Leu Thr Pro
1

<210> SEQ ID NO 44
<211> LENGTH: 4
<212> TYPE: PRT
<213> ORGANISM: Artificial Sequence
<220> FEATURE:
<223> OTHER INFORMATION: Four aa peptide corresponding to aa 747-750
      near the carboxy terminus of human ASPH.
<220> FEATURE:
<221> NAME/KEY: MISC_FEATURE
<222> LOCATION: (1)..(4)
<223> OTHER INFORMATION: Four aa peptide corresponding to aa 747-750
      near the carboxy terminus of human ASPH.

<400> SEQUENCE: 44

Leu Thr Pro Gln
1

<210> SEQ ID NO 45
<211> LENGTH: 4
<212> TYPE: PRT
<213> ORGANISM: Artificial Sequence
<220> FEATURE:
<223> OTHER INFORMATION: Four aa peptide corresponding to aa 748-751
      near the carboxy terminus of human ASPH.
<220> FEATURE:
<221> NAME/KEY: MISC_FEATURE
<222> LOCATION: (1)..(4)
<223> OTHER INFORMATION: Four aa peptide corresponding to aa 748-751
      near the carboxy terminus of human ASPH.
```

```
<400> SEQUENCE: 45

Thr Pro Gln Gln
1

<210> SEQ ID NO 46
<211> LENGTH: 4
<212> TYPE: PRT
<213> ORGANISM: Artificial Sequence
<220> FEATURE:
<223> OTHER INFORMATION: Four aa peptide corresponding to aa 749-752
      near the carboxy terminus of human ASPH.
<220> FEATURE:
<221> NAME/KEY: MISC_FEATURE
<222> LOCATION: (1)..(4)
<223> OTHER INFORMATION: Four aa peptide corresponding to aa 749-752
      near the carboxy terminus of human ASPH.

<400> SEQUENCE: 46

Pro Gln Gln Arg
1

<210> SEQ ID NO 47
<211> LENGTH: 4
<212> TYPE: PRT
<213> ORGANISM: Artificial Sequence
<220> FEATURE:
<223> OTHER INFORMATION: Four aa peptide corresponding to aa 750-753
      near the carboxy terminus of human ASPH.
<220> FEATURE:
<221> NAME/KEY: MISC_FEATURE
<222> LOCATION: (1)..(4)
<223> OTHER INFORMATION: Four aa peptide corresponding to aa 750-753
      near the carboxy terminus of human ASPH.

<400> SEQUENCE: 47

Gln Gln Arg Arg
1

<210> SEQ ID NO 48
<211> LENGTH: 4
<212> TYPE: PRT
<213> ORGANISM: Artificial Sequence
<220> FEATURE:
<223> OTHER INFORMATION: Four aa peptide corresponding to aa 751-754
      near the carboxy terminus of human ASPH.
<220> FEATURE:
<221> NAME/KEY: MISC_FEATURE
<222> LOCATION: (1)..(4)
<223> OTHER INFORMATION: Four aa peptide corresponding to aa 751-754
      near the carboxy terminus of human ASPH.

<400> SEQUENCE: 48

Gln Arg Arg Ser
1

<210> SEQ ID NO 49
<211> LENGTH: 4
<212> TYPE: PRT
<213> ORGANISM: Artificial Sequence
<220> FEATURE:
<223> OTHER INFORMATION: Four aa peptide corresponding to aa 752-755
      near the carboxy terminus of human ASPH.
<220> FEATURE:
<221> NAME/KEY: MISC_FEATURE
<222> LOCATION: (1)..(4)
<223> OTHER INFORMATION: Four aa peptide corresponding to aa 752-755
      near the carboxy terminus of human ASPH.

<400> SEQUENCE: 49
```

```
Arg Arg Ser Leu
1

<210> SEQ ID NO 50
<211> LENGTH: 4
<212> TYPE: PRT
<213> ORGANISM: Artificial Sequence
<220> FEATURE:
<223> OTHER INFORMATION: Four aa peptide corresponding to aa 753-756
      near the carboxy terminus of human ASPH.
<220> FEATURE:
<221> NAME/KEY: MISC_FEATURE
<222> LOCATION: (1)..(4)
<223> OTHER INFORMATION: Four aa peptide corresponding to aa 753-756
      near the carboxy terminus of human ASPH.

<400> SEQUENCE: 50

Arg Ser Leu Pro
1

<210> SEQ ID NO 51
<211> LENGTH: 4
<212> TYPE: PRT
<213> ORGANISM: Artificial Sequence
<220> FEATURE:
<223> OTHER INFORMATION: Four aa peptide corresponding to aa 754-757
      near the carboxy terminus of human ASPH.
<220> FEATURE:
<221> NAME/KEY: MISC_FEATURE
<222> LOCATION: (1)..(4)
<223> OTHER INFORMATION: Four aa peptide corresponding to aa 754-757
      near the carboxy terminus of human ASPH.

<400> SEQUENCE: 51

Ser Leu Pro Ala
1

<210> SEQ ID NO 52
<211> LENGTH: 4
<212> TYPE: PRT
<213> ORGANISM: Artificial Sequence
<220> FEATURE:
<223> OTHER INFORMATION: Four aa peptide corresponding to aa 746-758
      near the carboxy terminus of human ASPH.
<220> FEATURE:
<221> NAME/KEY: MISC_FEATURE
<222> LOCATION: (1)..(4)
<223> OTHER INFORMATION: Four aa peptide corresponding to aa 746-758
      near the carboxy terminus of human ASPH.

<400> SEQUENCE: 52

Leu Pro Ala Ile
1
```